(12) United States Patent
Whitfield et al.

(10) Patent No.: US 8,382,773 B2
(45) Date of Patent: Feb. 26, 2013

(54) ENDOSCOPIC SURGICAL CLIP APPLIER

(75) Inventors: Kenneth H. Whitfield, New Haven, CT (US); Gregory Sorrentino, Wallingford, CT (US)

(73) Assignee: Covidien LP, Mansfield, MA (US)

(*) Notice: Subject to any disclaimer, the term of this patent is extended or adjusted under 35 U.S.C. 154(b) by 582 days.

(21) Appl. No.: 12/055,446

(22) Filed: Mar. 26, 2008

(65) Prior Publication Data

US 2008/0243145 A1 Oct. 2, 2008

Related U.S. Application Data

(60) Provisional application No. 60/920,114, filed on Mar. 26, 2007.

(51) Int. Cl.
*A61B 17/10* (2006.01)
(52) U.S. Cl. ........................................ 606/143; 606/142
(58) Field of Classification Search .................. 606/142, 606/143, 157, 219, 213; 227/175.1, 176.1
See application file for complete search history.

(56) References Cited

U.S. PATENT DOCUMENTS

| | | | |
|---|---|---|---|
| 3,120,230 A | 2/1964 | Skold | |
| 3,638,847 A | 2/1972 | Noiles et al. | |
| 4,242,902 A | 1/1981 | Green | |
| 4,296,751 A | 10/1981 | Blake, III et al. | |
| 4,372,316 A | 2/1983 | Blake, III et al. | |
| 4,408,603 A | 10/1983 | Blake, III et al. | |
| 4,480,640 A | 11/1984 | Becht | |
| 4,480,641 A | 11/1984 | Failla et al. | |
| 4,487,204 A | 12/1984 | Hrouda | |
| 4,487,205 A | 12/1984 | Di Giovanni et al. | |
| 4,491,133 A | 1/1985 | Menges et al. | |
| 4,492,232 A | 1/1985 | Green | |
| 4,498,476 A | 2/1985 | Cerwin et al. | |
| 4,500,024 A | 2/1985 | DiGiovanni et al. | |
| 4,509,518 A | 4/1985 | McGarry et al. | |
| 4,512,345 A | 4/1985 | Green | |
| 4,522,207 A | 6/1985 | Klieman et al. | |
| 4,532,925 A | 8/1985 | Blake, III | |
| 4,534,351 A | 8/1985 | Rothfuss et al. | |

(Continued)

FOREIGN PATENT DOCUMENTS

| | | |
|---|---|---|
| EP | 0 085 931 A2 | 8/1983 |
| EP | 0 324 166 A2 | 7/1989 |

(Continued)

OTHER PUBLICATIONS

Extended European Search Report from Application No. EP 07 25 3807 mailed Nov. 26, 2008.

(Continued)

*Primary Examiner* — Corrine M McDermott
*Assistant Examiner* — Todd J Scherbel

(57) ABSTRACT

An apparatus for application of surgical clips is provided and includes a lockout system selectively engageable with a pusher bar to prevent the pusher bar from returning to a home position and to prevent a trigger from completing a full stroke when a plurality of clips are substantially exhausted. The apparatus may include a trip mechanism including a trip lever biased into contact with the pusher bar, wherein distal movement of the drive bar moves the trip mechanism until the trip lever engages a lip of the pusher bar and in turn distally moves the pusher bar. The apparatus may include a wedge plate including a distal end placeable between spaced-apart jaw members, wherein the wedge plate is moved proximally to withdraw the distal end thereof from between the jaw members when a drive channel is moved in a distal direction.

22 Claims, 44 Drawing Sheets

U.S. PATENT DOCUMENTS

| | | |
|---|---|---|
| 4,545,377 A | 10/1985 | Cerwin et al. |
| 4,549,544 A | 10/1985 | Favaron |
| 4,556,058 A | 12/1985 | Green |
| 4,557,263 A | 12/1985 | Green |
| 4,562,839 A | 1/1986 | Blake, III et al. |
| 4,572,183 A | 2/1986 | Juska |
| 4,576,165 A | 3/1986 | Green et al. |
| 4,576,166 A | 3/1986 | Montgomery et al. |
| 4,590,937 A | 5/1986 | Deniega |
| 4,598,711 A | 7/1986 | Deniega |
| 4,602,631 A | 7/1986 | Funatsu |
| 4,611,595 A | 9/1986 | Klieman et al. |
| 4,612,932 A | 9/1986 | Caspar et al. |
| 4,616,650 A | 10/1986 | Green et al. |
| 4,616,651 A | 10/1986 | Golden |
| 4,624,254 A | 11/1986 | McGarry et al. |
| 4,637,395 A | 1/1987 | Caspar et al. |
| 4,646,740 A | 3/1987 | Peters et al. |
| 4,647,504 A | 3/1987 | Kimimura et al. |
| 4,658,822 A | 4/1987 | Kees, Jr. |
| 4,660,558 A | 4/1987 | Kees, Jr. |
| 4,662,373 A | 5/1987 | Montgomery et al. |
| 4,662,374 A | 5/1987 | Blake, III |
| 4,671,278 A | 6/1987 | Chin |
| 4,671,282 A | 6/1987 | Tretbar |
| 4,674,504 A | 6/1987 | Klieman et al. |
| 4,681,107 A | 7/1987 | Kees, Jr. |
| 4,696,396 A | 9/1987 | Samuels |
| 4,702,247 A | 10/1987 | Blake, III et al. |
| 4,706,668 A | 11/1987 | Backer |
| 4,712,549 A | 12/1987 | Peters et al. |
| 4,733,664 A | 3/1988 | Kirsch et al. |
| 4,733,666 A | 3/1988 | Mercer, Jr. |
| 4,759,364 A | 7/1988 | Boebel |
| 4,765,335 A | 8/1988 | Schmidt et al. |
| 4,777,949 A | 10/1988 | Perlin |
| 4,777,950 A | 10/1988 | Kees, Jr. |
| 4,796,625 A | 1/1989 | Kees, Jr. |
| 4,799,481 A | 1/1989 | Transue et al. |
| 4,815,466 A | 3/1989 | Perlin |
| 4,817,604 A | 4/1989 | Smith, III |
| 4,821,721 A | 4/1989 | Chin et al. |
| 4,822,348 A | 4/1989 | Casey |
| 4,827,930 A | 5/1989 | Kees, Jr. |
| 4,834,096 A | 5/1989 | Oh et al. |
| 4,850,355 A | 7/1989 | Brooks et al. |
| 4,854,317 A | 8/1989 | Braun |
| 4,856,517 A | 8/1989 | Collins et al. |
| 4,929,239 A | 5/1990 | Braun |
| 4,929,240 A | 5/1990 | Kirsch et al. |
| 4,931,058 A | 6/1990 | Cooper |
| 4,932,955 A | 6/1990 | Merz et al. |
| 4,934,364 A | 6/1990 | Green |
| 4,943,298 A | 7/1990 | Fujita et al. |
| 4,957,500 A | 9/1990 | Liang et al. |
| 4,966,603 A | 10/1990 | Focelle et al. |
| 4,967,949 A | 11/1990 | Sandhaus |
| 4,983,176 A | 1/1991 | Cushman et al. |
| 4,988,355 A | 1/1991 | Leveen et al. |
| 5,002,552 A | 3/1991 | Casey |
| 5,026,379 A | 6/1991 | Yoon |
| 5,030,224 A | 7/1991 | Wright et al. |
| 5,030,226 A | 7/1991 | Green et al. |
| 5,032,127 A | 7/1991 | Frazee et al. |
| 5,035,692 A | 7/1991 | Lyon et al. |
| 5,047,038 A | 9/1991 | Peters et al. |
| 5,049,152 A | 9/1991 | Simon et al. |
| 5,049,153 A | 9/1991 | Nakao et al. |
| 5,053,045 A | 10/1991 | Schmidt et al. |
| 5,059,202 A | 10/1991 | Liang et al. |
| 5,062,846 A | 11/1991 | Oh et al. |
| 5,078,731 A | 1/1992 | Hayhurst |
| 5,084,057 A | 1/1992 | Green et al. |
| 5,100,416 A | 3/1992 | Oh et al. |
| 5,100,420 A | 3/1992 | Green et al. |
| 5,104,394 A | 4/1992 | Knoepfler |
| 5,104,395 A | 4/1992 | Thornton et al. |
| 5,112,343 A | 5/1992 | Thornton |
| 5,122,150 A | 6/1992 | Puig |
| 5,127,915 A | 7/1992 | Mattson |
| 5,129,885 A | 7/1992 | Green et al. |
| 5,156,608 A | 10/1992 | Troidl et al. |
| 5,160,339 A | 11/1992 | Chen et al. |
| 5,163,945 A | 11/1992 | Ortiz et al. |
| 5,171,247 A | 12/1992 | Hughett et al. |
| 5,171,249 A | 12/1992 | Stefanchik et al. |
| 5,171,250 A | 12/1992 | Yoon |
| 5,171,251 A | 12/1992 | Bregen et al. |
| 5,171,252 A | 12/1992 | Friedland |
| 5,171,253 A | 12/1992 | Klieman |
| 5,192,288 A | 3/1993 | Thompson et al. |
| 5,197,970 A | 3/1993 | Green et al. |
| 5,199,566 A | 4/1993 | Ortiz et al. |
| 5,201,746 A | 4/1993 | Shichman |
| 5,201,900 A | 4/1993 | Nardella |
| 5,207,691 A | 5/1993 | Nardella |
| 5,207,692 A | 5/1993 | Kraus et al. |
| 5,217,473 A | 6/1993 | Yoon |
| 5,219,353 A | 6/1993 | Garvey, III et al. |
| 5,246,450 A | 9/1993 | Thornton et al. |
| 5,269,792 A | 12/1993 | Kovac et al. |
| 5,281,228 A | 1/1994 | Wolfson |
| 5,282,807 A | 2/1994 | Knoepfler |
| 5,282,808 A | 2/1994 | Kovac et al. |
| 5,282,832 A | 2/1994 | Toso et al. |
| 5,289,963 A | 3/1994 | McGarry et al. |
| 5,290,299 A | 3/1994 | Fain et al. |
| 5,300,081 A | 4/1994 | Young et al. |
| 5,304,183 A | 4/1994 | Gourlay et al. |
| 5,306,280 A | 4/1994 | Bregen et al. |
| 5,306,283 A | 4/1994 | Conners |
| 5,312,426 A | 5/1994 | Segawa et al. |
| 5,330,442 A | 7/1994 | Green et al. |
| 5,330,487 A | 7/1994 | Thornton et al. |
| 5,340,360 A | 8/1994 | Stefanchik |
| 5,342,373 A | 8/1994 | Stefanchik et al. |
| 5,354,304 A | 10/1994 | Allen et al. |
| 5,354,306 A | 10/1994 | Garvey, III et al. |
| 5,366,458 A | 11/1994 | Korthoff et al. |
| 5,366,459 A | 11/1994 | Yoon |
| 5,368,600 A | 11/1994 | Failla et al. |
| 5,382,253 A | 1/1995 | Hogendijk |
| 5,382,254 A | 1/1995 | McGarry et al. |
| 5,382,255 A | 1/1995 | Castro et al. |
| 5,383,881 A | 1/1995 | Green et al. |
| 5,395,375 A | 3/1995 | Turkel et al. |
| 5,395,381 A | 3/1995 | Green et al. |
| 5,403,327 A | 4/1995 | Thornton et al. |
| 5,409,498 A | 4/1995 | Braddock et al. |
| 5,413,584 A | 5/1995 | Schulze |
| 5,423,835 A | 6/1995 | Green et al. |
| 5,425,740 A | 6/1995 | Hutchinson, Jr. |
| 5,431,667 A | 7/1995 | Thompson et al. |
| 5,431,668 A | 7/1995 | Burbank, III et al. |
| 5,431,669 A | 7/1995 | Thompson et al. |
| 5,439,468 A | 8/1995 | Schulze et al. |
| 5,441,509 A | 8/1995 | Vidal et al. |
| 5,447,513 A | 9/1995 | Davison et al. |
| 5,449,365 A | 9/1995 | Green et al. |
| 5,462,555 A | 10/1995 | Bolanos et al. |
| 5,462,558 A | 10/1995 | Kolesa et al. |
| 5,464,416 A | 11/1995 | Steckel |
| 5,474,566 A | 12/1995 | Alesi et al. |
| 5,474,567 A | 12/1995 | Stefanchik et al. |
| 5,474,572 A | 12/1995 | Hayhurst |
| 5,487,746 A | 1/1996 | Yu et al. |
| 5,501,693 A | 3/1996 | Gravener |
| 5,509,920 A | 4/1996 | Phillips et al. |
| 5,514,149 A | 5/1996 | Green et al. |
| 5,520,701 A | 5/1996 | Lerch |
| 5,522,823 A | 6/1996 | Kuntz et al. |
| 5,527,318 A | 6/1996 | McGarry |
| 5,527,319 A | 6/1996 | Green et al. |
| 5,527,320 A | 6/1996 | Carruthers et al. |
| 5,542,949 A | 8/1996 | Yoon |
| 5,547,474 A | 8/1996 | Kloeckl et al. |
| 5,569,274 A | 10/1996 | Rapacki et al. |

| | | | | | | |
|---|---|---|---|---|---|---|
| 5,571,121 | A | 11/1996 | Heifetz | 5,928,251 A | 7/1999 | Aranyi et al. |
| 5,575,802 | A | 11/1996 | McQuildin et al. | 5,938,667 A | 8/1999 | Peyser et al. |
| 5,582,615 | A | 12/1996 | Foshee et al. | 5,951,574 A | 9/1999 | Stefanchik et al. |
| 5,584,840 | A | 12/1996 | Ramsey et al. | 5,972,003 A | 10/1999 | Rousseau et al. |
| 5,591,178 | A | 1/1997 | Green et al. | 5,976,159 A | 11/1999 | Bolduc et al. |
| 5,593,414 | A | 1/1997 | Shipp et al. | 5,993,465 A | 11/1999 | Shipp et al. |
| 5,593,421 | A | 1/1997 | Bauer | 6,004,335 A | 12/1999 | Vaitekunas et al. |
| 5,601,573 | A | 2/1997 | Fogelberg et al. | 6,017,358 A | 1/2000 | Yoon et al. |
| 5,601,574 | A | 2/1997 | Stefanchik et al. | RE36,720 E | 5/2000 | Green et al. |
| 5,607,436 | A | 3/1997 | Pratt et al. | 6,059,799 A | 5/2000 | Aranyi et al. |
| 5,618,291 | A | 4/1997 | Thompson et al. | 6,099,536 A | 8/2000 | Petillo |
| 5,618,306 | A | 4/1997 | Roth et al. | 6,099,537 A | 8/2000 | Sugai et al. |
| 5,620,452 | A | 4/1997 | Yoon | 6,139,555 A | 10/2000 | Hart et al. |
| 5,626,585 | A | 5/1997 | Mittelstadt et al. | 6,210,418 B1 | 4/2001 | Storz et al. |
| 5,626,586 | A | 5/1997 | Pistl et al. | 6,217,590 B1 | 4/2001 | Levinson |
| 5,626,592 | A | 5/1997 | Phillips et al. | 6,228,097 B1 | 5/2001 | Levinson et al. |
| RE35,525 | E * | 6/1997 | Stefanchik et al. ............ 606/142 | 6,241,740 B1 | 6/2001 | Davis et al. |
| 5,634,930 | A | 6/1997 | Thornton et al. | 6,258,105 B1 | 7/2001 | Hart et al. |
| 5,643,291 | A | 7/1997 | Pier et al. | 6,261,302 B1 | 7/2001 | Voegele et al. |
| 5,645,551 | A | 7/1997 | Green et al. | 6,273,898 B1 | 8/2001 | Kienzle et al. |
| 5,645,553 | A | 7/1997 | Kolesa et al. | 6,277,131 B1 | 8/2001 | Kalikow |
| 5,649,937 | A | 7/1997 | Bito et al. | 6,306,149 B1 | 10/2001 | Meade |
| 5,653,720 | A | 8/1997 | Johnson et al. | 6,318,619 B1 | 11/2001 | Lee |
| 5,662,676 | A | 9/1997 | Koninckx | 6,322,571 B1 | 11/2001 | Adams |
| 5,662,679 | A | 9/1997 | Voss et al. | 6,350,269 B1 | 2/2002 | Shipp et al. |
| 5,665,097 | A | 9/1997 | Baker et al. | 6,352,541 B1 | 3/2002 | Kienzle et al. |
| 5,676,676 | A | 10/1997 | Porter | 6,391,035 B1 | 5/2002 | Appleby et al. |
| 5,681,330 | A | 10/1997 | Hughett et al. | 6,423,079 B1 | 7/2002 | Blake, III |
| 5,683,405 | A | 11/1997 | Yacoubian et al. | 6,428,548 B1 | 8/2002 | Durgin et al. |
| 5,695,502 | A | 12/1997 | Pier et al. | 6,440,144 B1 | 8/2002 | Bacher |
| 5,695,505 | A | 12/1997 | Yoon | 6,461,363 B1 | 10/2002 | Gadberry et al. |
| 5,697,938 | A | 12/1997 | Jensen et al. | 6,464,710 B1 | 10/2002 | Foster |
| 5,700,270 | A | 12/1997 | Peyser et al. | 6,494,886 B1 | 12/2002 | Wilk et al. |
| 5,700,271 | A | 12/1997 | Whitfield et al. | 6,517,536 B2 | 2/2003 | Hooven et al. |
| 5,702,048 | A | 12/1997 | Eberlin | 6,520,972 B2 | 2/2003 | Peters |
| 5,709,706 | A | 1/1998 | Kienzle et al. | 6,527,786 B1 | 3/2003 | Davis et al. |
| 5,713,911 | A | 2/1998 | Racenet et al. | 6,537,289 B1 | 3/2003 | Kayan et al. |
| 5,713,912 | A | 2/1998 | Porter | 6,546,935 B2 | 4/2003 | Hooven |
| 5,720,756 | A | 2/1998 | Green et al. | 6,551,333 B2 | 4/2003 | Kuhns et al. |
| 5,722,982 | A | 3/1998 | Ferreira et al. | 6,569,171 B2 | 5/2003 | DeGuillebon et al. |
| 5,725,537 | A | 3/1998 | Green et al. | 6,579,304 B1 | 6/2003 | Hart et al. |
| 5,725,538 | A | 3/1998 | Green et al. | 6,599,298 B1 | 7/2003 | Forster et al. |
| 5,725,542 | A | 3/1998 | Yoon | 6,602,252 B2 | 8/2003 | Mollenauer |
| 5,733,295 | A | 3/1998 | Back et al. | 6,607,540 B1 | 8/2003 | Shipp |
| 5,755,726 | A | 5/1998 | Pratt et al. | 6,613,060 B2 | 9/2003 | Adams et al. |
| 5,766,189 | A | 6/1998 | Matsuno | 6,626,916 B1 | 9/2003 | Yeung et al. |
| 5,769,857 | A | 6/1998 | Reztzov et al. | 6,626,922 B1 | 9/2003 | Hart et al. |
| 5,772,673 | A | 6/1998 | Cuny et al. | 6,648,898 B1 | 11/2003 | Baxter |
| 5,776,146 | A | 7/1998 | Sackier et al. | 6,652,538 B2 | 11/2003 | Kayan et al. |
| 5,776,147 | A | 7/1998 | Dolendo | 6,652,539 B2 | 11/2003 | Shipp et al. |
| 5,779,718 | A | 7/1998 | Green et al. | 6,673,083 B1 | 1/2004 | Kayan et al. |
| 5,779,720 | A | 7/1998 | Walder-Utz et al. | 6,676,659 B2 | 1/2004 | Hutchins et al. |
| 5,782,844 | A | 7/1998 | Yoon et al. | 6,679,894 B2 | 1/2004 | Damarati |
| 5,788,698 | A | 8/1998 | Savornin | RE38,445 E | 2/2004 | Pistl et al. |
| 5,792,149 | A | 8/1998 | Sherts et al. | 6,695,854 B1 | 2/2004 | Kayan et al. |
| 5,792,150 | A | 8/1998 | Pratt et al. | 6,706,057 B1 | 3/2004 | Bidoia et al. |
| 5,797,922 | A | 8/1998 | Hessel et al. | 6,716,226 B2 | 4/2004 | Sixto, Jr. et al. |
| 5,810,853 | A | 9/1998 | Yoon | 6,723,109 B2 | 4/2004 | Solingen |
| 5,817,116 | A | 10/1998 | Takahashi et al. | 6,743,240 B2 | 6/2004 | Smith et al. |
| 5,827,306 | A | 10/1998 | Yoon | 6,773,438 B1 | 8/2004 | Knodel et al. |
| 5,833,695 | A | 11/1998 | Yoon | 6,773,440 B2 | 8/2004 | Gannoe et al. |
| 5,833,696 | A | 11/1998 | Whitfield et al. | 6,776,783 B1 | 8/2004 | Frantzen et al. |
| 5,833,700 | A | 11/1998 | Fogelberg et al. | 6,776,784 B2 | 8/2004 | Ginn |
| 5,843,097 | A | 12/1998 | Mayenberger et al. | 6,780,195 B2 | 8/2004 | Porat |
| 5,843,101 | A | 12/1998 | Fry | 6,793,663 B2 | 9/2004 | Kneifel et al. |
| 5,846,255 | A | 12/1998 | Casey | 6,793,664 B2 | 9/2004 | Mazzocchi et al. |
| 5,849,019 | A | 12/1998 | Yoon | 6,802,848 B2 | 10/2004 | Anderson et al. |
| 5,858,018 | A | 1/1999 | Shipp et al. | 6,814,742 B2 | 11/2004 | Kimura et al. |
| 5,861,005 | A | 1/1999 | Kontos | 6,818,009 B2 | 11/2004 | Hart et al. |
| 5,868,759 | A | 2/1999 | Peyser et al. | 6,821,273 B2 | 11/2004 | Mollenauer |
| 5,868,761 | A | 2/1999 | Nicholas et al. | 6,821,284 B2 | 11/2004 | Sturtz et al. |
| 5,876,410 | A | 3/1999 | Petillo | 6,824,547 B2 | 11/2004 | Wilson, Jr. et al. |
| 5,895,394 | A | 4/1999 | Kienzle et al. | 6,824,548 B2 | 11/2004 | Smith et al. |
| 5,897,565 | A | 4/1999 | Foster | 6,835,199 B2 | 12/2004 | McGuckin, Jr. et al. |
| 5,904,693 | A | 5/1999 | Dicesare et al. | 6,835,200 B2 | 12/2004 | Laufer et al. |
| 5,913,862 | A | 6/1999 | Ramsey et al. | 6,837,893 B2 | 1/2005 | Miller |
| 5,918,791 | A * | 7/1999 | Sorrentino et al. ........ 227/175.3 | 6,837,894 B2 | 1/2005 | Pugsley, Jr. et al. |
| 5,921,996 | A | 7/1999 | Sherman | 6,837,895 B2 | 1/2005 | Mayenberger |
| 5,921,997 | A | 7/1999 | Fogelberg et al. | 6,840,945 B2 | 1/2005 | Manetakis et al. |

| | | |
|---|---|---|
| 6,843,794 B2 | 1/2005 | Sixto, Jr. et al. |
| 6,849,078 B2 | 2/2005 | Durgin et al. |
| 6,849,079 B1 | 2/2005 | Blake, III et al. |
| 6,853,879 B2 | 2/2005 | Sunaoshi |
| 6,869,435 B2 | 3/2005 | Blake, III |
| 6,869,436 B2 | 3/2005 | Wendlandt |
| 6,889,116 B2 | 5/2005 | Jinno |
| 6,896,682 B1 | 5/2005 | McClellan et al. |
| 6,905,503 B2 | 6/2005 | Gifford, III et al. |
| 6,911,032 B2 | 6/2005 | Jugenheimer et al. |
| 6,911,033 B2 | 6/2005 | de Guillebon et al. |
| 6,913,607 B2 | 7/2005 | Ainsworth et al. |
| 6,916,327 B2 | 7/2005 | Northrup, III et al. |
| 6,923,818 B2 | 8/2005 | Muramatsu et al. |
| 6,939,356 B2 | 9/2005 | Debbas |
| 6,942,674 B2 | 9/2005 | Belef et al. |
| 6,942,676 B2 | 9/2005 | Buelna |
| 6,945,978 B1 | 9/2005 | Hyde |
| 6,945,979 B2 | 9/2005 | Kortenbach et al. |
| 6,949,107 B2 | 9/2005 | McGuckin, Jr. et al. |
| 6,953,465 B2 | 10/2005 | Dieck et al. |
| 6,955,643 B2 | 10/2005 | Gellman et al. |
| 6,959,852 B2 | 11/2005 | Shelton, IV et al. |
| 6,960,218 B2 | 11/2005 | Rennich |
| 6,960,221 B2 | 11/2005 | Ho et al. |
| 6,962,594 B1 | 11/2005 | Thevenet |
| 6,963,792 B1 | 11/2005 | Green |
| 6,964,363 B2 | 11/2005 | Wales et al. |
| 6,964,668 B2 | 11/2005 | Modesitt et al. |
| 6,966,875 B1 | 11/2005 | Longobardi |
| 6,966,917 B1 | 11/2005 | Suyker et al. |
| 6,966,919 B2 | 11/2005 | Sixto, Jr. et al. |
| 6,969,391 B1 | 11/2005 | Gazzani |
| 6,972,023 B2 | 12/2005 | Whayne et al. |
| 6,972,027 B2 | 12/2005 | Fallin et al. |
| 6,973,770 B2 | 12/2005 | Schnipke et al. |
| 6,974,462 B2 | 12/2005 | Sater |
| 6,974,466 B2 | 12/2005 | Ahmed et al. |
| 6,974,475 B1 | 12/2005 | Wall |
| 6,981,505 B2 | 1/2006 | Krause et al. |
| 6,981,628 B2 | 1/2006 | Wales |
| 6,991,635 B2 | 1/2006 | Takamoto et al. |
| 7,052,504 B2 * | 5/2006 | Hughett .............. 606/142 |
| 7,056,330 B2 | 6/2006 | Gayton |
| 7,108,703 B2 | 9/2006 | Danitz et al. |
| 7,144,402 B2 | 12/2006 | Kuester, III |
| 7,175,648 B2 | 2/2007 | Nakao |
| 7,179,265 B2 | 2/2007 | Manetakis et al. |
| 7,207,997 B2 | 4/2007 | Shipp et al. |
| 7,211,091 B2 | 5/2007 | Fowler et al. |
| 7,211,092 B2 | 5/2007 | Hughett |
| 7,214,230 B2 | 5/2007 | Brock et al. |
| 7,214,232 B2 | 5/2007 | Bowman et al. |
| 7,223,271 B2 | 5/2007 | Muramatsu et al. |
| 7,223,272 B2 | 5/2007 | Francese et al. |
| 7,232,445 B2 | 6/2007 | Kortenbach et al. |
| 7,261,724 B2 | 8/2007 | Molitor et al. |
| 7,261,725 B2 | 8/2007 | Binmoeller |
| 7,264,625 B1 | 9/2007 | Buncke |
| 7,288,098 B2 | 10/2007 | Huitema et al. |
| 7,297,149 B2 | 11/2007 | Vitali et al. |
| 7,316,693 B2 | 1/2008 | Viola |
| 7,316,696 B2 | 1/2008 | Wilson, Jr. et al. |
| 7,326,223 B2 | 2/2008 | Wilson, Jr. |
| 7,329,266 B2 | 2/2008 | Royse et al. |
| 7,331,968 B2 | 2/2008 | Arp et al. |
| 7,338,503 B2 | 3/2008 | Rosenberg et al. |
| 7,357,805 B2 | 4/2008 | Masuda et al. |
| 7,637,917 B2 * | 12/2009 | Whitfield et al. .............. 606/143 |
| 7,717,926 B2 * | 5/2010 | Whitfield et al. .............. 606/143 |
| 7,819,886 B2 * | 10/2010 | Whitfield et al. .............. 606/143 |
| 2001/0047178 A1 | 11/2001 | Peters |
| 2002/0068947 A1 | 6/2002 | Kuhns et al. |
| 2002/0082618 A1 | 6/2002 | Shipp et al. |
| 2002/0087169 A1 | 7/2002 | Brock et al. |
| 2002/0087170 A1 | 7/2002 | Kuhns et al. |
| 2002/0099388 A1 | 7/2002 | Mayenberger |
| 2002/0120279 A1 | 8/2002 | DeGuillebon et al. |
| 2002/0128668 A1 | 9/2002 | Manetakis et al. |
| 2002/0177859 A1 | 11/2002 | Monassevitch et al. |
| 2002/0198537 A1 | 12/2002 | Smith et al. |
| 2002/0198538 A1 | 12/2002 | Kortenbach et al. |
| 2002/0198539 A1 | 12/2002 | Sixto, Jr. et al. |
| 2002/0198540 A1 | 12/2002 | Smith et al. |
| 2002/0198541 A1 | 12/2002 | Smith et al. |
| 2003/0014060 A1 | 1/2003 | Wilson, Jr. et al. |
| 2003/0018345 A1 | 1/2003 | Green |
| 2003/0023249 A1 | 1/2003 | Manetakis |
| 2003/0040759 A1 | 2/2003 | de Guillebon et al. |
| 2003/0105476 A1 | 6/2003 | Sancoff et al. |
| 2003/0114867 A1 | 6/2003 | Bolduc et al. |
| 2003/0135224 A1 | 7/2003 | Blake, III |
| 2003/0167063 A1 | 9/2003 | Kerr |
| 2003/0225423 A1 | 12/2003 | Huitema |
| 2003/0233105 A1 | 12/2003 | Gayton |
| 2004/0010272 A1 | 1/2004 | Manetakis et al. |
| 2004/0097970 A1 | 5/2004 | Hughett |
| 2004/0097971 A1 | 5/2004 | Hughett |
| 2004/0138681 A1 | 7/2004 | Pier |
| 2004/0153100 A1 | 8/2004 | Ahlberg et al. |
| 2005/0080440 A1 | 4/2005 | Durgin et al. |
| 2005/0085830 A1 | 4/2005 | Lehman et al. |
| 2005/0090837 A1 | 4/2005 | Sixto, Jr. et al. |
| 2005/0090838 A1 | 4/2005 | Sixto, Jr. et al. |
| 2005/0096670 A1 | 5/2005 | Wellman et al. |
| 2005/0096671 A1 | 5/2005 | Wellman et al. |
| 2005/0096672 A1 * | 5/2005 | Manetakis et al. .............. 606/142 |
| 2005/0101975 A1 | 5/2005 | Nguyen et al. |
| 2005/0107807 A1 | 5/2005 | Nakao |
| 2005/0107809 A1 | 5/2005 | Litscher et al. |
| 2005/0107810 A1 | 5/2005 | Morales et al. |
| 2005/0107811 A1 | 5/2005 | Starksen et al. |
| 2005/0107812 A1 | 5/2005 | Starksen et al. |
| 2005/0107871 A1 | 5/2005 | Realyvasquez et al. |
| 2005/0113847 A1 | 5/2005 | Gadberry et al. |
| 2005/0119671 A1 | 6/2005 | Reydel et al. |
| 2005/0119673 A1 | 6/2005 | Gordon et al. |
| 2005/0119677 A1 | 6/2005 | Shipp |
| 2005/0125010 A1 | 6/2005 | Smith et al. |
| 2005/0143767 A1 | 6/2005 | Kimura et al. |
| 2005/0149063 A1 | 7/2005 | Young et al. |
| 2005/0149064 A1 | 7/2005 | Peterson et al. |
| 2005/0149068 A1 | 7/2005 | Williams et al. |
| 2005/0149069 A1 | 7/2005 | Bertolero et al. |
| 2005/0165415 A1 | 7/2005 | Wales |
| 2005/0165418 A1 | 7/2005 | Chan |
| 2005/0171560 A1 | 8/2005 | Hughett |
| 2005/0177176 A1 | 8/2005 | Gerbi et al. |
| 2005/0177177 A1 | 8/2005 | Viola |
| 2005/0203547 A1 | 9/2005 | Weller et al. |
| 2005/0203548 A1 | 9/2005 | Weller et al. |
| 2005/0216036 A1 | 9/2005 | Nakao |
| 2005/0216056 A1 | 9/2005 | Valdevit et al. |
| 2005/0222588 A1 | 10/2005 | Vandenbroek et al. |
| 2005/0222590 A1 | 10/2005 | Gadberry et al. |
| 2005/0222665 A1 | 10/2005 | Aranyi |
| 2005/0228411 A1 | 10/2005 | Manzo |
| 2005/0228416 A1 | 10/2005 | Burbank et al. |
| 2005/0234478 A1 | 10/2005 | Wixey et al. |
| 2005/0251183 A1 | 11/2005 | Buckman et al. |
| 2005/0251184 A1 | 11/2005 | Anderson |
| 2005/0256529 A1 | 11/2005 | Yawata et al. |
| 2005/0267495 A1 | 12/2005 | Ginn et al. |
| 2005/0273122 A1 | 12/2005 | Theroux et al. |
| 2005/0277951 A1 | 12/2005 | Smith et al. |
| 2005/0277952 A1 | 12/2005 | Arp et al. |
| 2005/0277953 A1 | 12/2005 | Francese et al. |
| 2005/0277954 A1 | 12/2005 | Smith et al. |
| 2005/0277955 A1 | 12/2005 | Palmer et al. |
| 2005/0277956 A1 | 12/2005 | Francese et al. |
| 2005/0277958 A1 | 12/2005 | Levinson |
| 2005/0288689 A1 | 12/2005 | Kammerer et al. |
| 2005/0288690 A1 | 12/2005 | Bourque et al. |
| 2006/0004388 A1 | 1/2006 | Whayne et al. |
| 2006/0004390 A1 | 1/2006 | Rosenberg et al. |
| 2006/0009789 A1 | 1/2006 | Gambale et al. |
| 2006/0009790 A1 | 1/2006 | Blake, III et al. |
| 2006/0009792 A1 | 1/2006 | Baker et al. |

| | | |
|---|---|---|
| 2006/0020270 A1 | 1/2006 | Jabba et al. |
| 2006/0020271 A1 | 1/2006 | Stewart et al. |
| 2006/0047305 A1 | 3/2006 | Ortiz et al. |
| 2006/0047306 A1 | 3/2006 | Ortiz et al. |
| 2006/0064117 A1 | 3/2006 | Aranyi et al. |
| 2006/0079912 A1 | 4/2006 | Whitfield et al. |
| 2006/0079913 A1* | 4/2006 | Whitfield et al. ............. 606/142 |
| 2006/0085015 A1* | 4/2006 | Whitfield et al. ............. 606/142 |
| 2006/0100649 A1 | 5/2006 | Hart |
| 2006/0111731 A1 | 5/2006 | Manzo |
| 2006/0129170 A1 | 6/2006 | Royce et al. |
| 2006/0163312 A1* | 7/2006 | Viola et al. ................. 227/175.1 |
| 2006/0173470 A1 | 8/2006 | Oray et al. |
| 2006/0178683 A1 | 8/2006 | Shimoji et al. |
| 2006/0184182 A1 | 8/2006 | Aranyi et al. |
| 2006/0190013 A1 | 8/2006 | Menn |
| 2006/0195125 A1 | 8/2006 | Sakakine et al. |
| 2006/0200179 A1 | 9/2006 | Barker et al. |
| 2006/0217749 A1 | 9/2006 | Wilson, Jr. et al. |
| 2006/0224170 A1 | 10/2006 | Duff |
| 2006/0235437 A1 | 10/2006 | Vitali et al. |
| 2006/0235438 A1 | 10/2006 | Huitema et al. |
| 2006/0235439 A1 | 10/2006 | Molitor et al. |
| 2006/0235440 A1 | 10/2006 | Huitema et al. |
| 2006/0235441 A1 | 10/2006 | Huitema et al. |
| 2006/0235442 A1 | 10/2006 | Huitema |
| 2006/0235443 A1 | 10/2006 | Huitema et al. |
| 2006/0235444 A1 | 10/2006 | Huitema et al. |
| 2006/0259045 A1 | 11/2006 | Damarati |
| 2006/0259049 A1 | 11/2006 | Harada et al. |
| 2006/0264987 A1 | 11/2006 | Sgro |
| 2006/0271072 A1 | 11/2006 | Hummel et al. |
| 2007/0016228 A1 | 1/2007 | Salas |
| 2007/0021761 A1 | 1/2007 | Phillips |
| 2007/0023476 A1 | 2/2007 | Whitman et al. |
| 2007/0023477 A1 | 2/2007 | Whitman et al. |
| 2007/0027458 A1 | 2/2007 | Sixto, Jr. et al. |
| 2007/0034669 A1 | 2/2007 | de la Torre et al. |
| 2007/0038233 A1 | 2/2007 | Martinez et al. |
| 2007/0049947 A1 | 3/2007 | Menn et al. |
| 2007/0049948 A1 | 3/2007 | Menn et al. |
| 2007/0049949 A1 | 3/2007 | Manetakis |
| 2007/0049950 A1 | 3/2007 | Theroux et al. |
| 2007/0049951 A1 | 3/2007 | Menn |
| 2007/0049953 A2 | 3/2007 | Shimoji et al. |
| 2007/0073314 A1 | 3/2007 | Gadberry et al. |
| 2007/0083218 A1 | 4/2007 | Morris |
| 2007/0093856 A1 | 4/2007 | Whitfield |
| 2007/0106314 A1 | 5/2007 | Dunn |
| 2007/0112365 A1 | 5/2007 | Hilal et al. |
| 2007/0118155 A1 | 5/2007 | Goldfarb et al. |
| 2007/0118161 A1 | 5/2007 | Kennedy et al. |
| 2007/0118163 A1 | 5/2007 | Boudreaux et al. |
| 2007/0118174 A1 | 5/2007 | Chu |
| 2007/0123916 A1 | 5/2007 | Maier et al. |
| 2007/0142848 A1 | 6/2007 | Ainsworth et al. |
| 2007/0142851 A1 | 6/2007 | Sixto, Jr. et al. |
| 2007/0149988 A1 | 6/2007 | Michler et al. |
| 2007/0149989 A1 | 6/2007 | Santilli et al. |
| 2007/0162060 A1 | 7/2007 | Wild |
| 2007/0185504 A1 | 8/2007 | Manetakis et al. |
| 2007/0191868 A1 | 8/2007 | Theroux et al. |
| 2007/0213747 A1 | 9/2007 | Monassevitch et al. |
| 2007/0250080 A1 | 10/2007 | Jones et al. |
| 2007/0265640 A1 | 11/2007 | Kortenbach et al. |
| 2007/0276417 A1 | 11/2007 | Mendes, Jr. et al. |
| 2007/0282355 A1 | 12/2007 | Brown et al. |
| 2007/0293875 A1 | 12/2007 | Soetikno et al. |
| 2008/0004636 A1 | 1/2008 | Walberg et al. |
| 2008/0004637 A1 | 1/2008 | Klassen et al. |
| 2008/0004639 A1 | 1/2008 | Huitema et al. |
| 2008/0015615 A1 | 1/2008 | Molitor et al. |
| 2008/0027465 A1 | 1/2008 | Vitali et al. |
| 2008/0027466 A1 | 1/2008 | Vitali et al. |
| 2008/0045981 A1 | 2/2008 | Margolin et al. |
| 2008/0051808 A1 | 2/2008 | Rivera et al. |
| 2008/0065118 A1 | 3/2008 | Damarati |
| 2008/0065119 A1 | 3/2008 | Viola |
| 2008/0243145 A1 | 10/2008 | Whitfield et al. |
| 2009/0228024 A1* | 9/2009 | Whitfield et al. ............. 606/143 |
| 2010/0057102 A1* | 3/2010 | Sorrentino et al. ............. 606/143 |
| 2010/0057103 A1* | 3/2010 | Sorrentino et al. ............. 606/143 |
| 2010/0057104 A1* | 3/2010 | Sorrentino et al. ............. 606/143 |
| 2010/0057105 A1* | 3/2010 | Sorrentino et al. ............. 606/143 |
| 2010/0057106 A1* | 3/2010 | Sorrentino et al. ............. 606/143 |
| 2010/0057107 A1* | 3/2010 | Sorrentino et al. ............. 606/143 |
| 2010/0121351 A1* | 5/2010 | Whitfield et al. ............. 606/143 |
| 2010/0222790 A1* | 9/2010 | Whitfield et al. ............. 606/143 |
| 2010/0274262 A1 | 10/2010 | Schulz et al. |

FOREIGN PATENT DOCUMENTS

| | | |
|---|---|---|
| EP | 0 392 750 A1 | 10/1990 |
| EP | 0 598 529 A2 | 5/1994 |
| EP | 0 769 275 A1 | 5/1994 |
| EP | 0 685 204 A1 | 12/1995 |
| EP | 0 732 078 A2 | 9/1996 |
| EP | 0 755 655 A | 1/1997 |
| EP | 0 769 274 A1 | 4/1997 |
| EP | 0 769 275 | 4/1997 |
| EP | 0 834 286 | 4/1998 |
| EP | 1 317 906 | 6/2003 |
| EP | 1 609 427 A1 | 12/2005 |
| EP | 1 712 191 A2 | 10/2006 |
| EP | 1 813 199 A1 | 8/2007 |
| EP | 1 908 423 A | 4/2008 |
| EP | 1 908 423 A2 | 4/2008 |
| EP | 1 913 881 A1 | 4/2008 |
| EP | 2 229 895 A1 | 9/2010 |
| JP | 2003 033361 A | 2/2003 |
| WO | WO 2005/091457 | 9/2005 |
| WO | WO 2006/042076 | 4/2006 |
| WO | WO 2006/042084 | 4/2006 |
| WO | WO 2006/042110 | 4/2006 |
| WO | WO 2008/118928 A2 | 10/2008 |
| WO | WO 2008/127968 A | 10/2008 |

OTHER PUBLICATIONS

European Search Report corresponding to EP 09252053; date of mailing is Dec. 1, 2009; date of completion of Search is Nov. 24, 2009 (3 Pages).

European Search Report corresponding to EP 09252051; date of mailing is Jan. 28, 2010; date of completion of Search is Dec. 21, 2009 (3 Pages).

European Search Report corresponding to EP 09252050; date of mailing is Jan. 21, 2010; date of completion of Search is Dec. 23, 2009 (3 Pages).

European Search Report corresponding to EP 09252054; date of mailing is Jan. 22, 2010; date of completion of Search is Jan. 7, 2010 (3 Pages).

International Search Report for application EP 07 25 3905 dated Feb. 7, 2008.

Extended European Search Report corresponding to EP 09252056.8, date of mailing is Feb. 5, 2010, date of completion of Search is Jan. 8, 2010 (3 Pages).

Extended European Search Report corresponding to EP 10250497.4. date of mailing is May 12, 2010; date of completion of Search is May 4, 2010 (6 Pages).

International Search Report for corresponding PCT/US08/58185 date of completion is Sep. 9, 2008 (2 Pages).

International Search Report from European Application No. EP 07 25 3807 mailed Aug. 1, 2008.

International Search Report from PCT Application No. PCT/US08/59859 dated Sep. 18, 2008.

European Search Report corresponding to EP 05810218.7, mailed on May 20, 2011; completed on Apr. 18, 2011; 3 pages.

European Search Report corresponding to EP 05807612.6, mailed on May 20, 2011; completed on May 2, 2011; 3 pages.

Extended European Search Report corresponding to EP 10251737.2, mailed on May 20, 2011; completed on May 9, 2011; 4 pages.

Extended European Search Report corresponding to EP 10252079.8, date of mailing is Mar. 17, 2011; date of completion of Search is Mar. 8, 2011 (3 Pages).

The Extended European Search Report corresponding to European Application No. EP 11250214.1, completed May 25, 2011; mailed Jun. 1, 2011; (3 Pages).

European Search Report corresponding to European Application No. EP 05 80 2686.5, completed Jan. 9, 2012; mailed Jan. 18, 2012; (3 Pages).

The Extended European Search Report corresponding to European Application No. EP 12 15 1313.9, completed Mar. 20, 2012 and mailed Apr. 12, 2012; (5 Pages).

The Extended European Search Report corresponding to European Application No. EP 12 16 1291.5, completed Apr. 24, 2012 and mailed May 4, 2012; (5 Pages).

The Extended European Search Report corresponding to European Application No. EP 12 16 2288.0, completed Jun. 4, 2012 and mailed Jul. 7, 2012; (6 Pages).

The Extended European Search Report corresponding to European Application No. EP 12 16 5891.8, completed Jun. 12, 2012 and mailed Jun. 20, 2012; (6 Pages).

The Extended European Search Report corresponding to European Application No. EP 12 16 4955.2, completed Aug. 23, 2012 and mailed Sep. 4, 2012; (5 Pages).

* cited by examiner

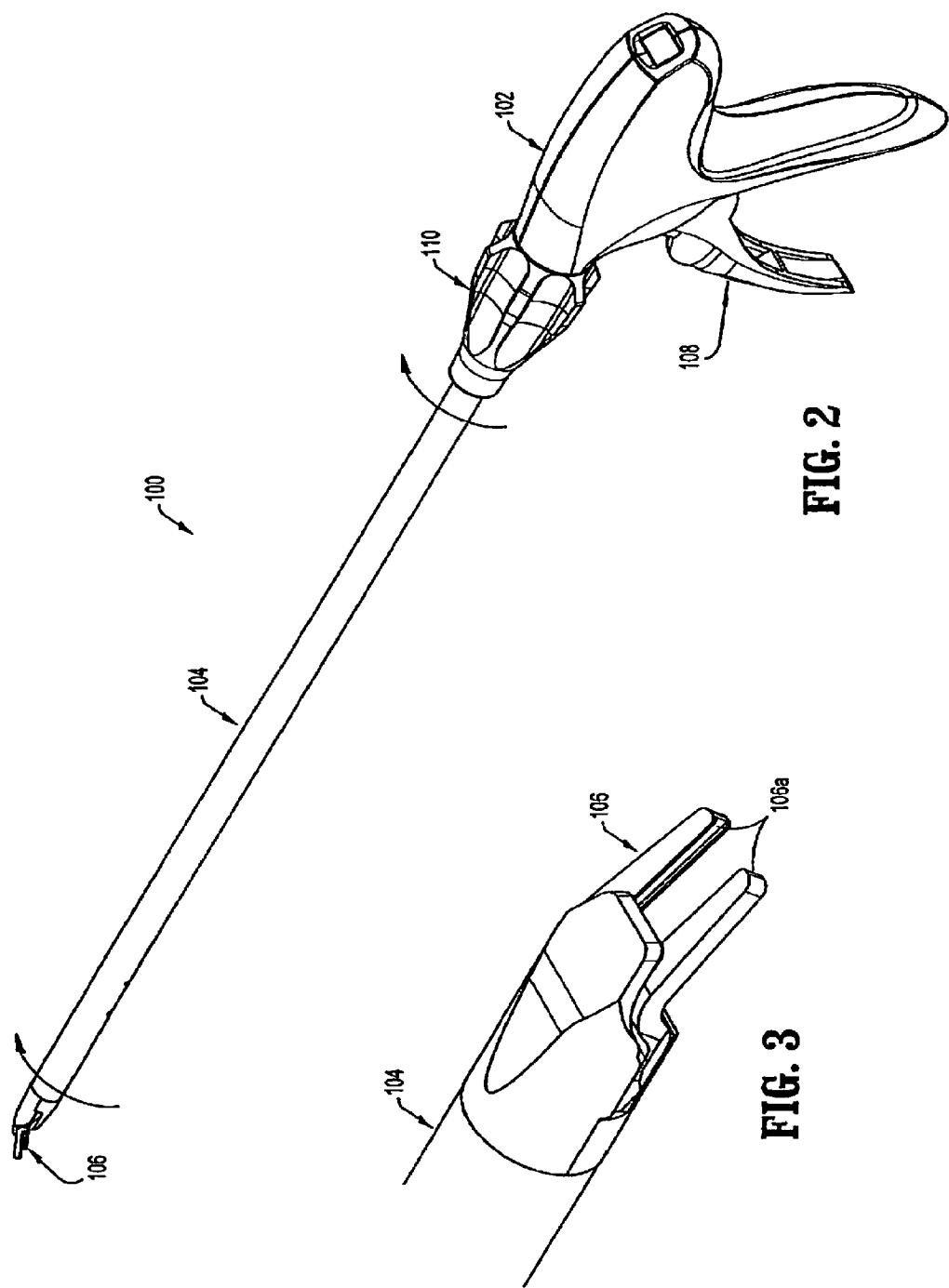

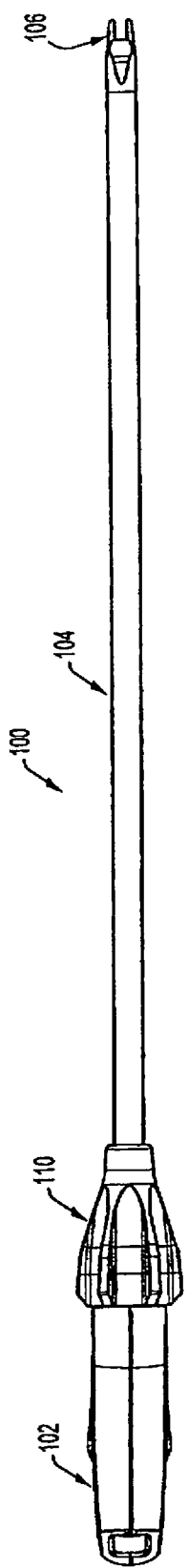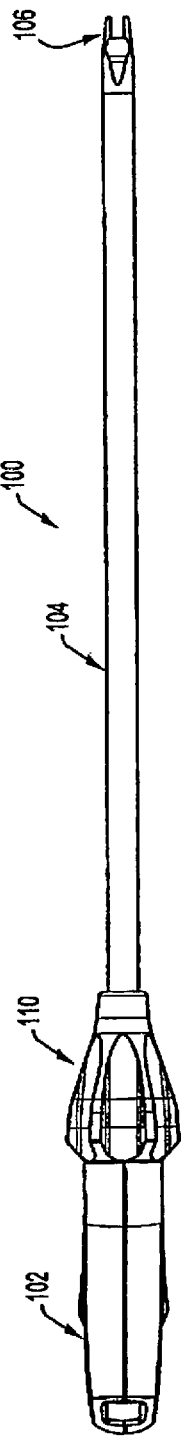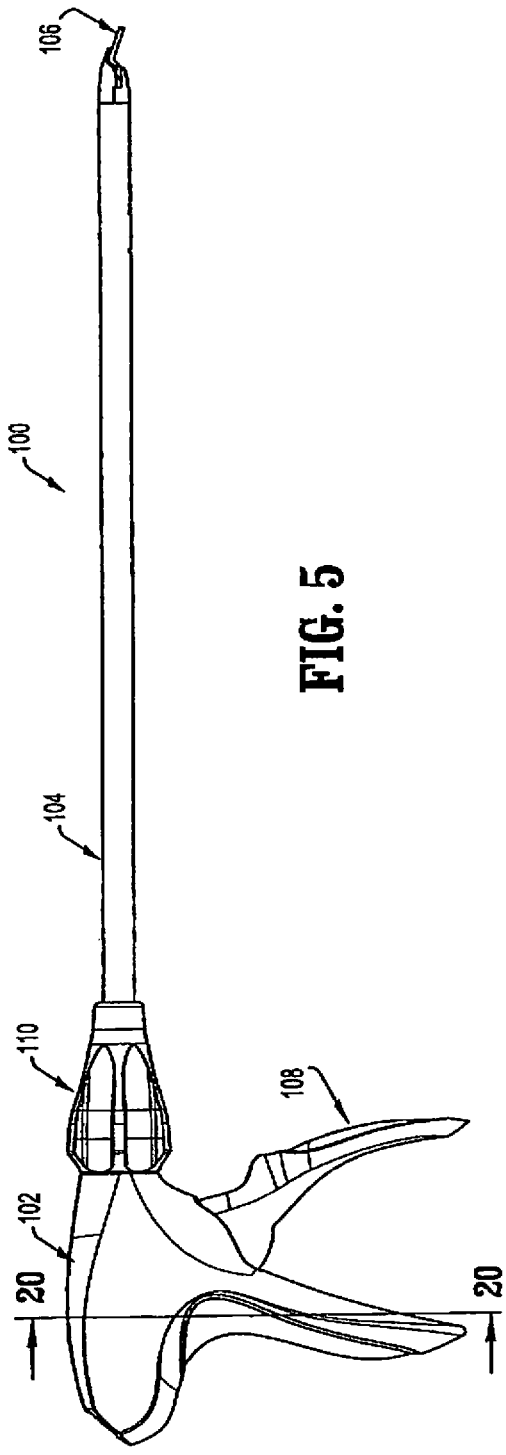

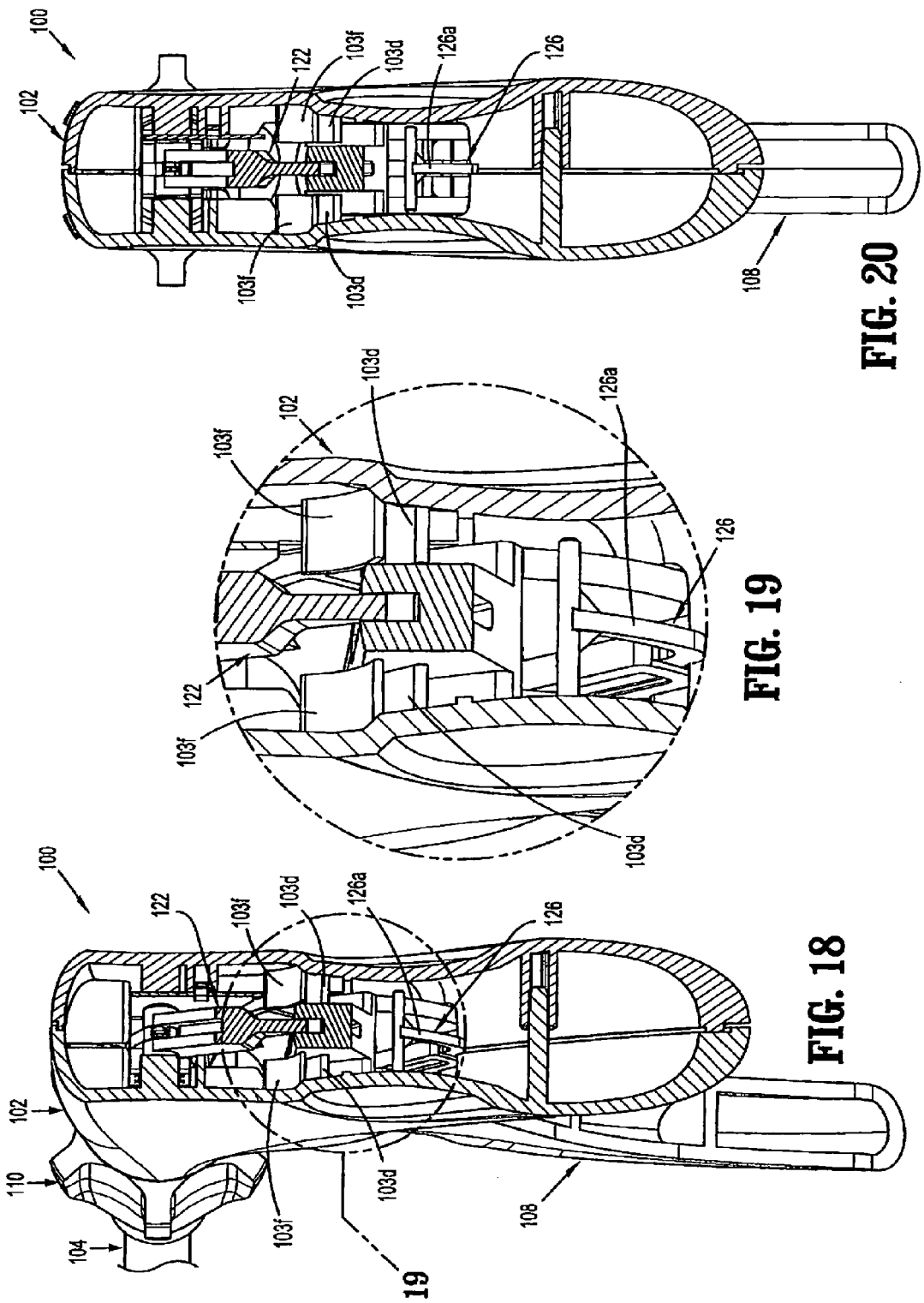

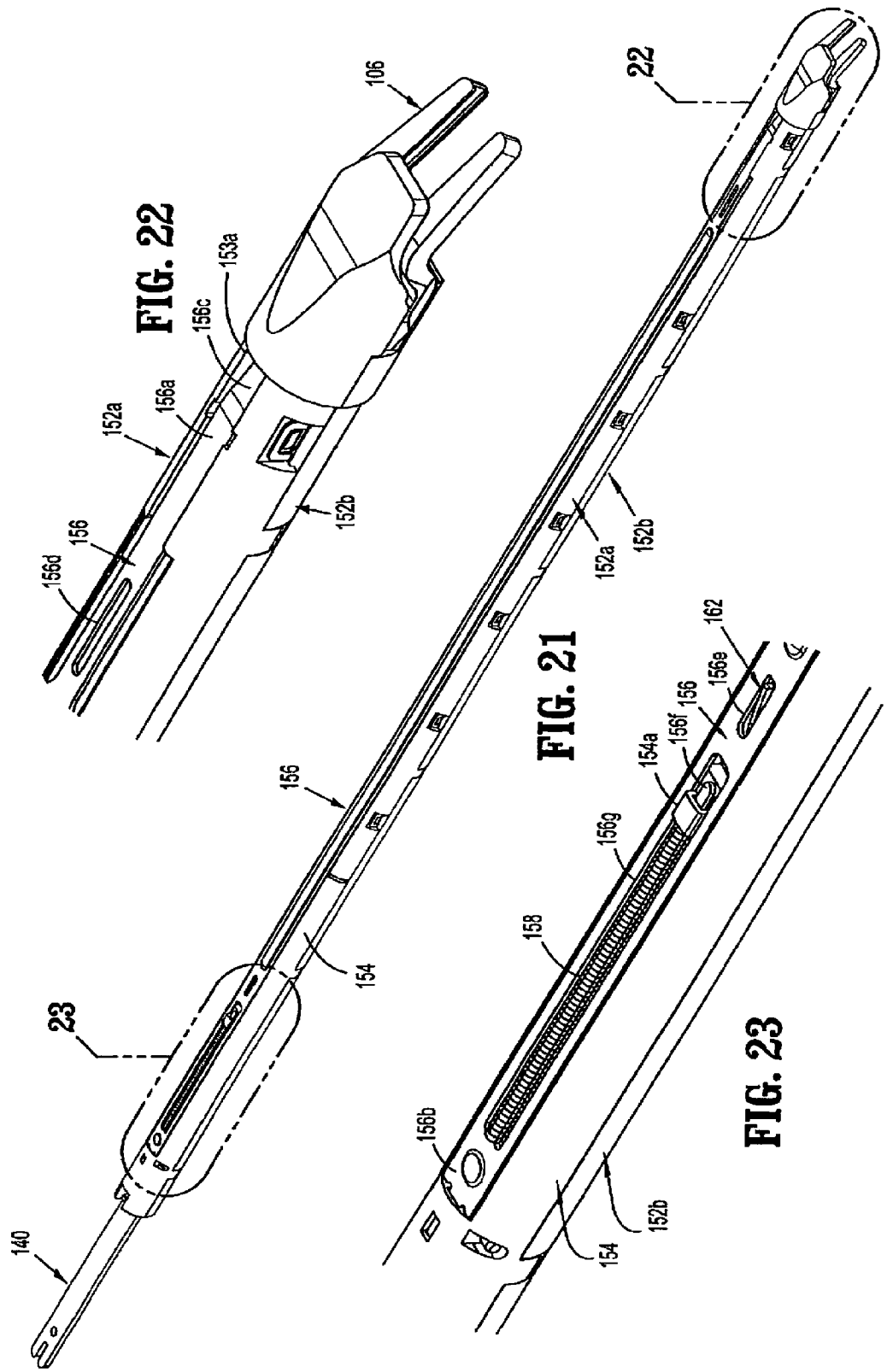

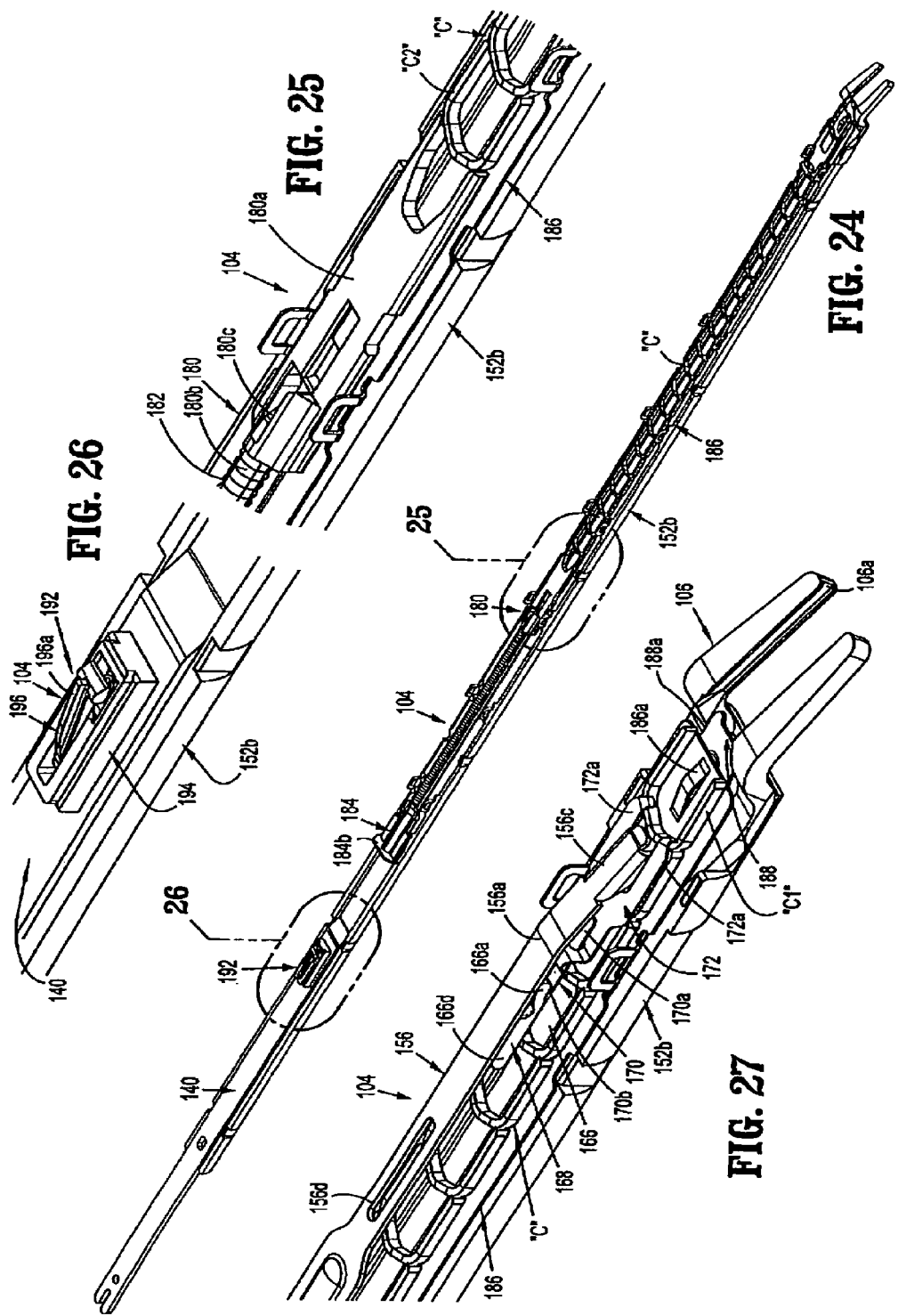

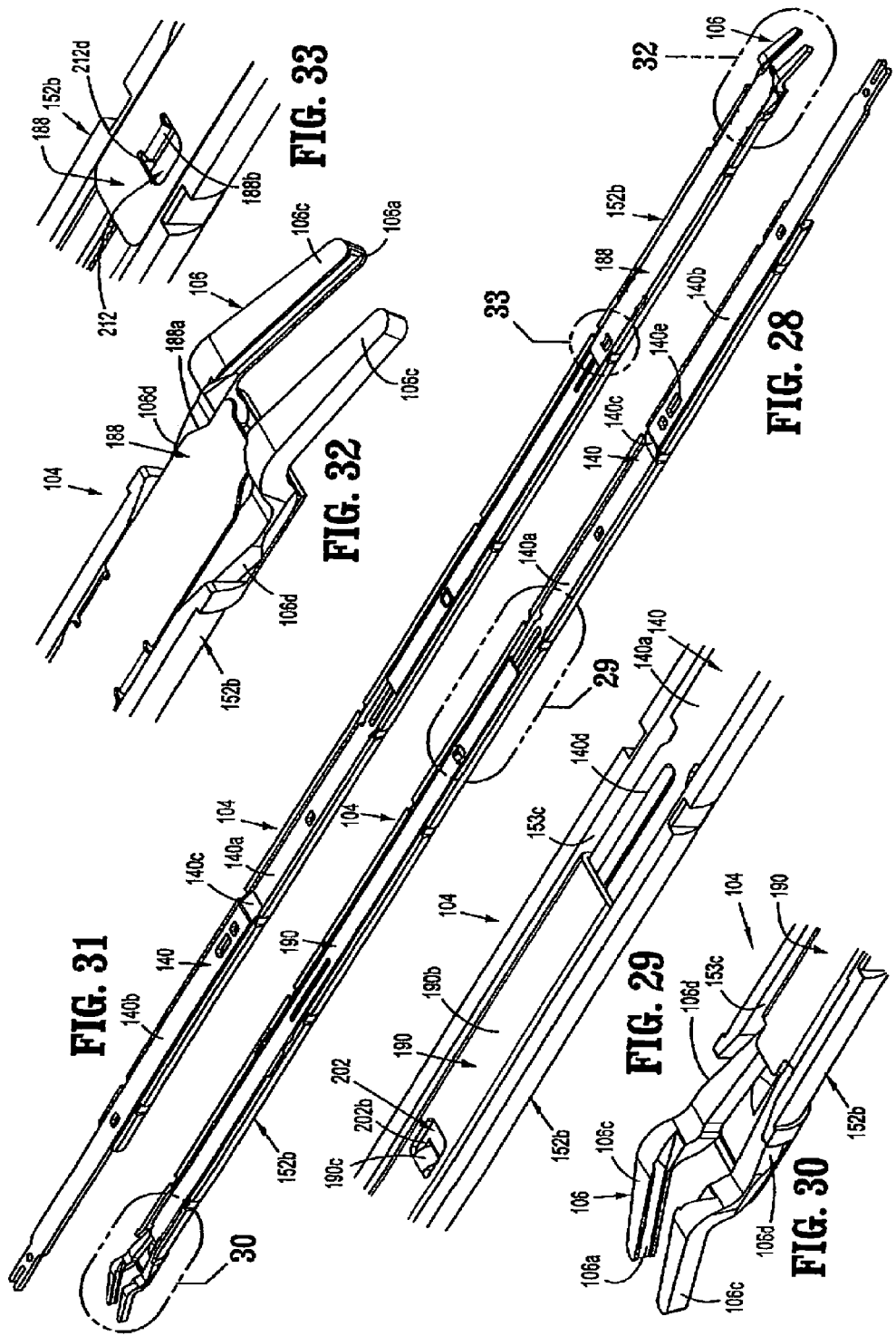

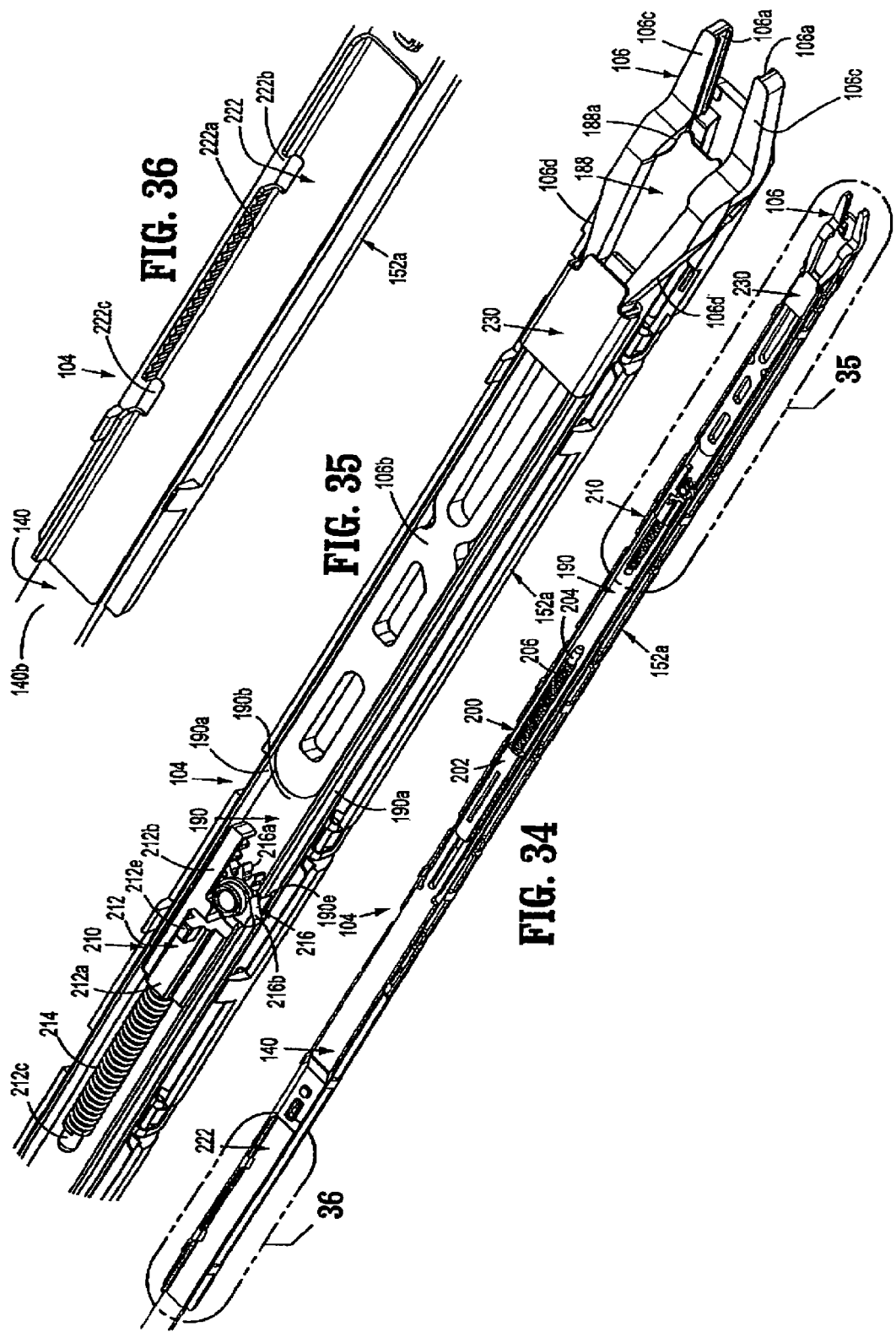

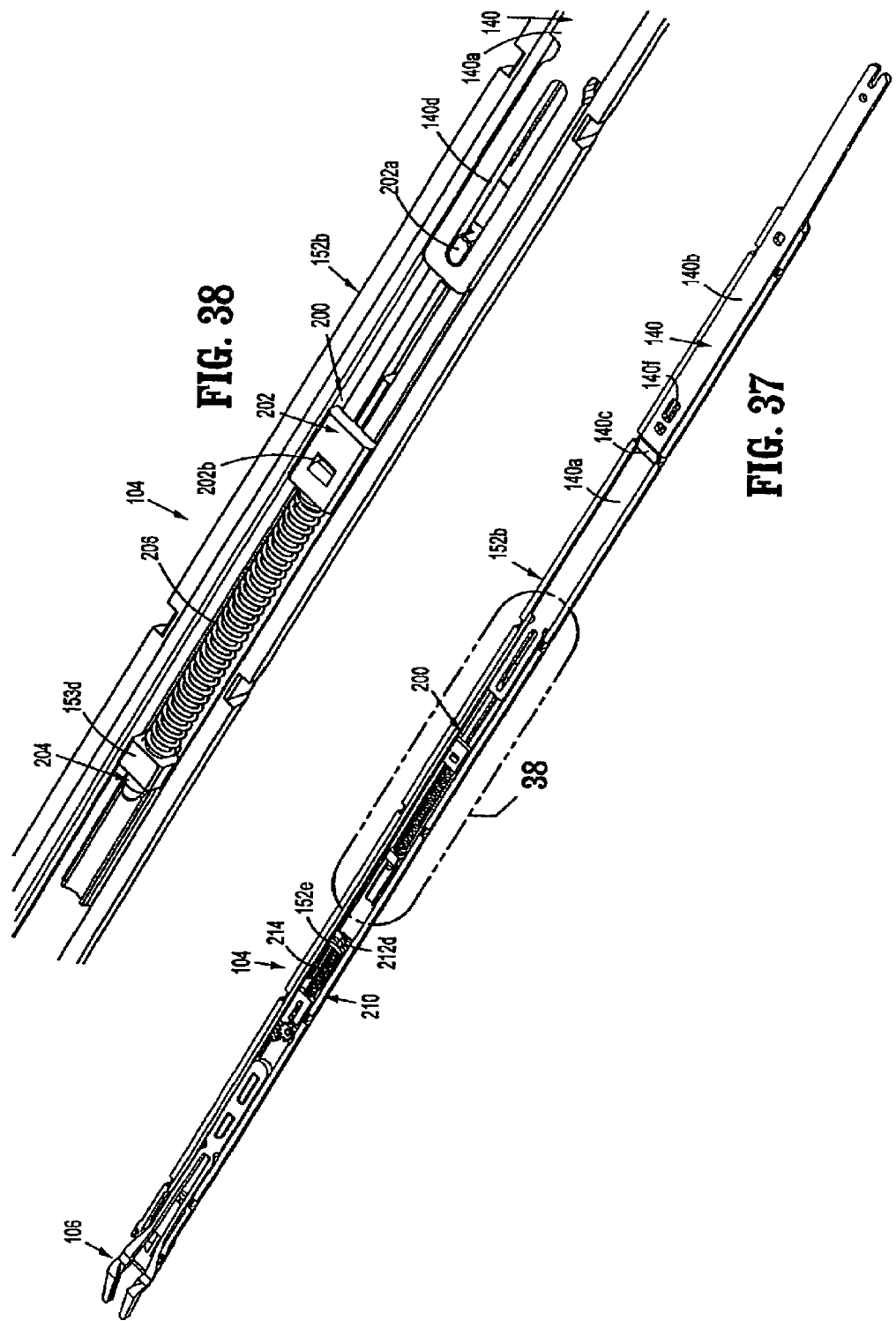

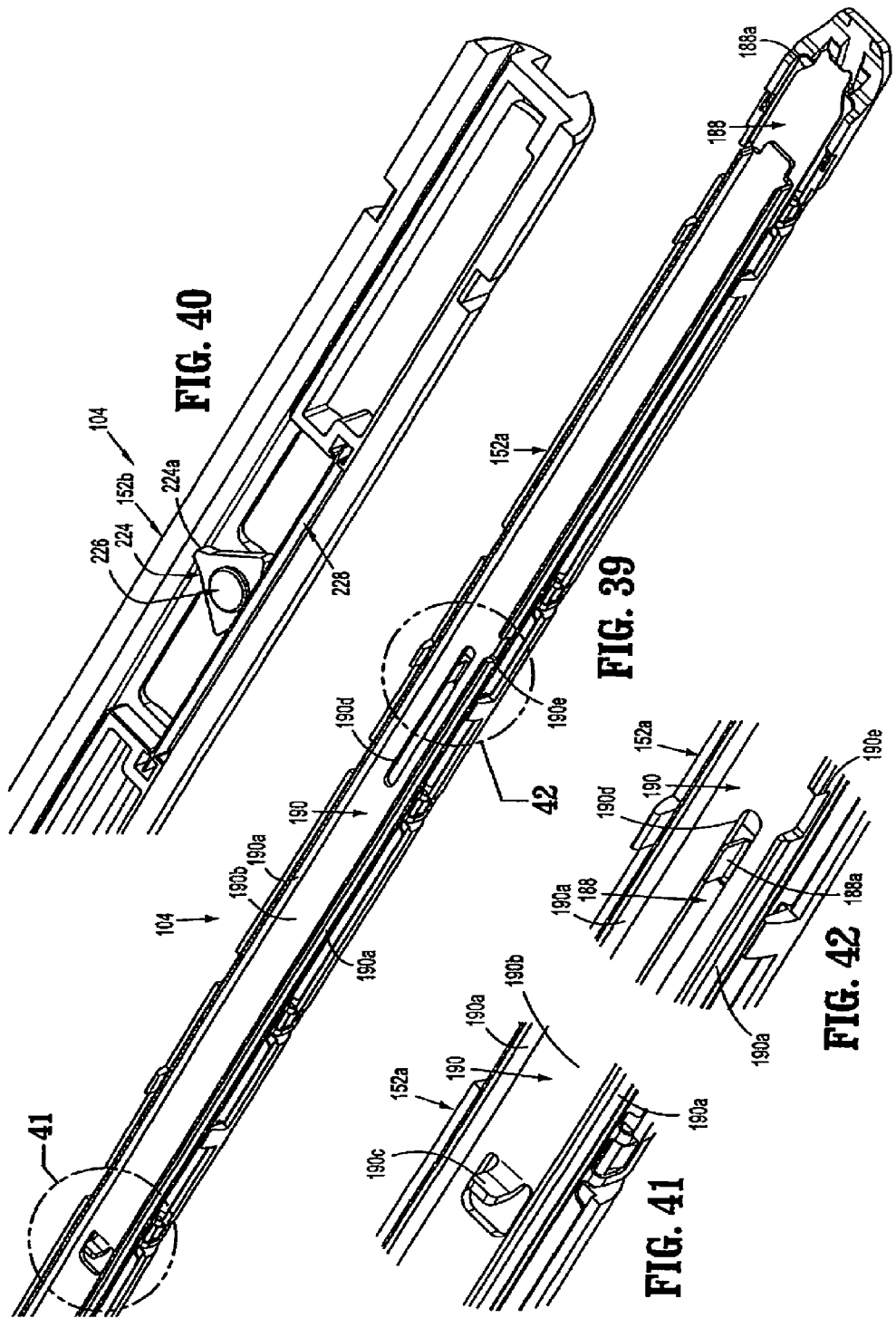

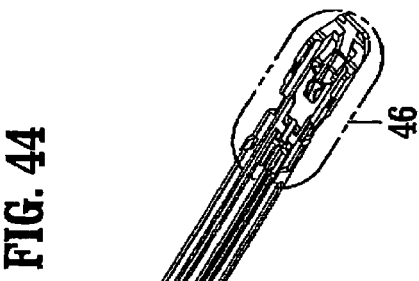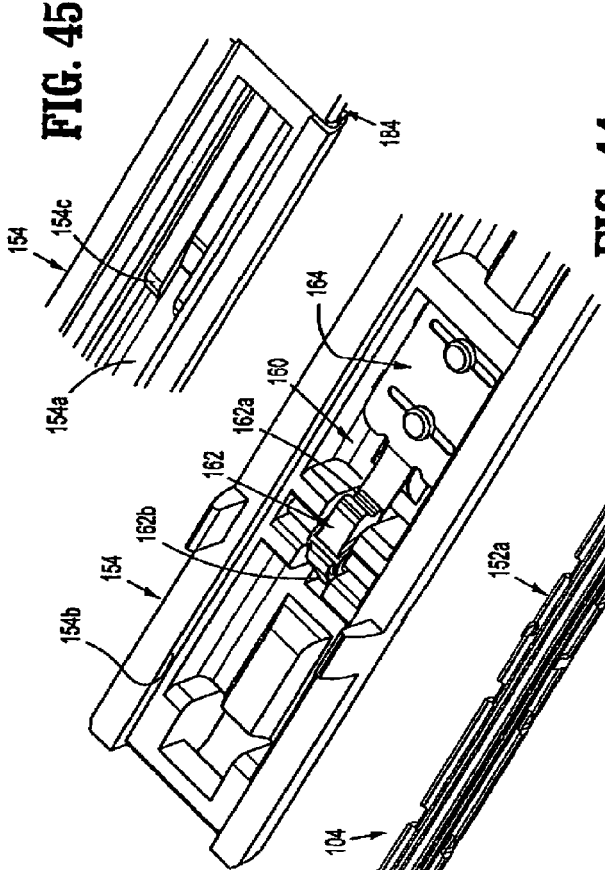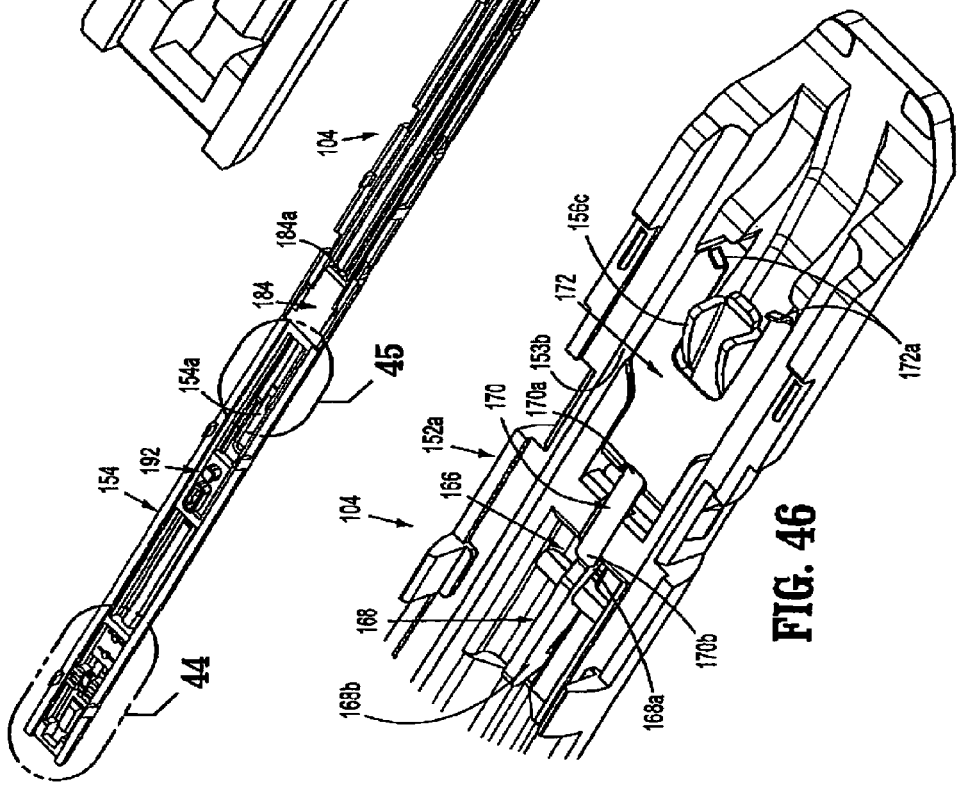

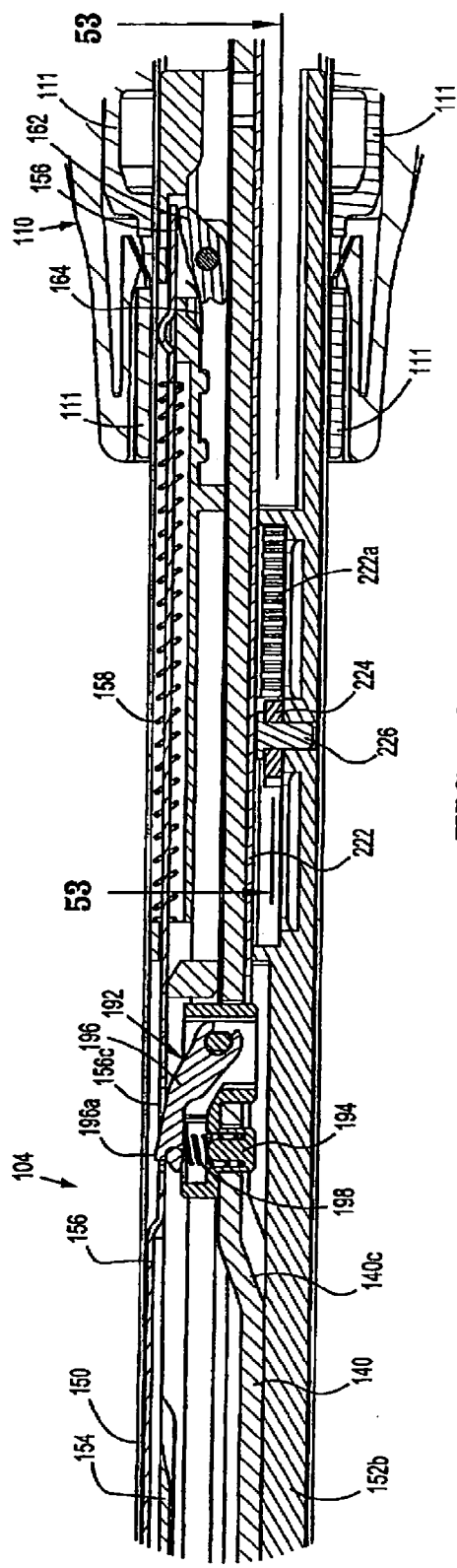
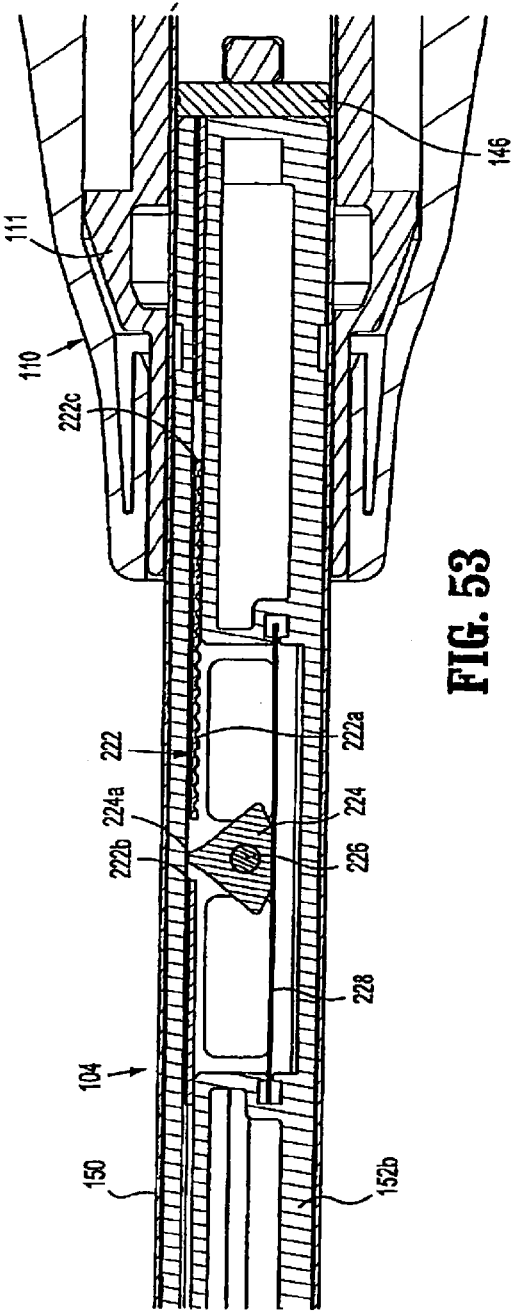
FIG. 52
FIG. 53

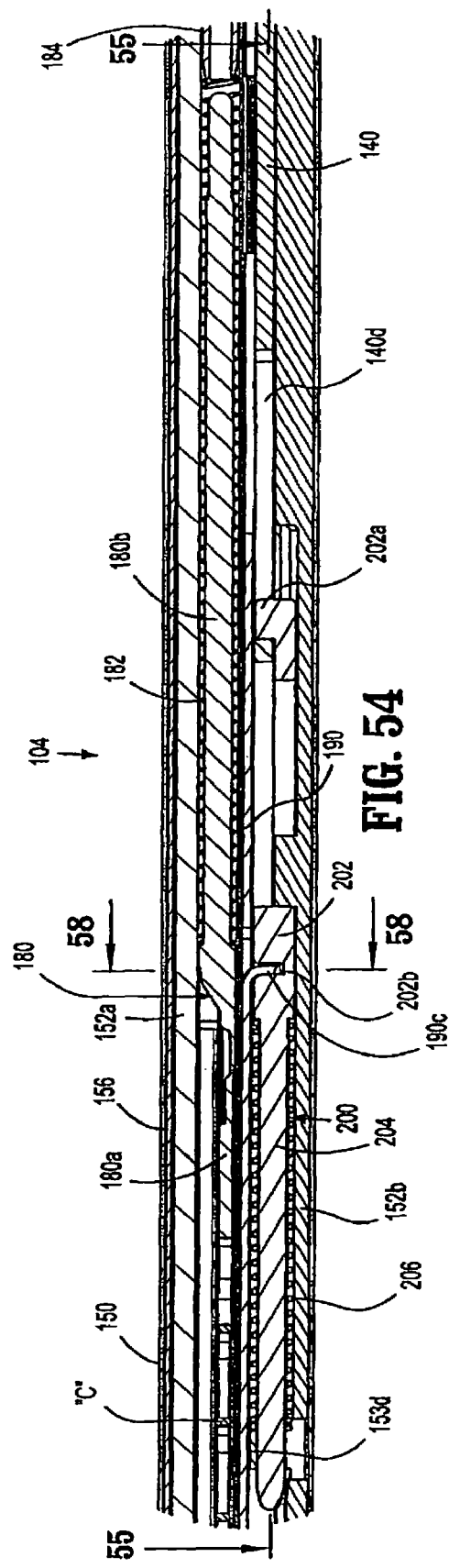
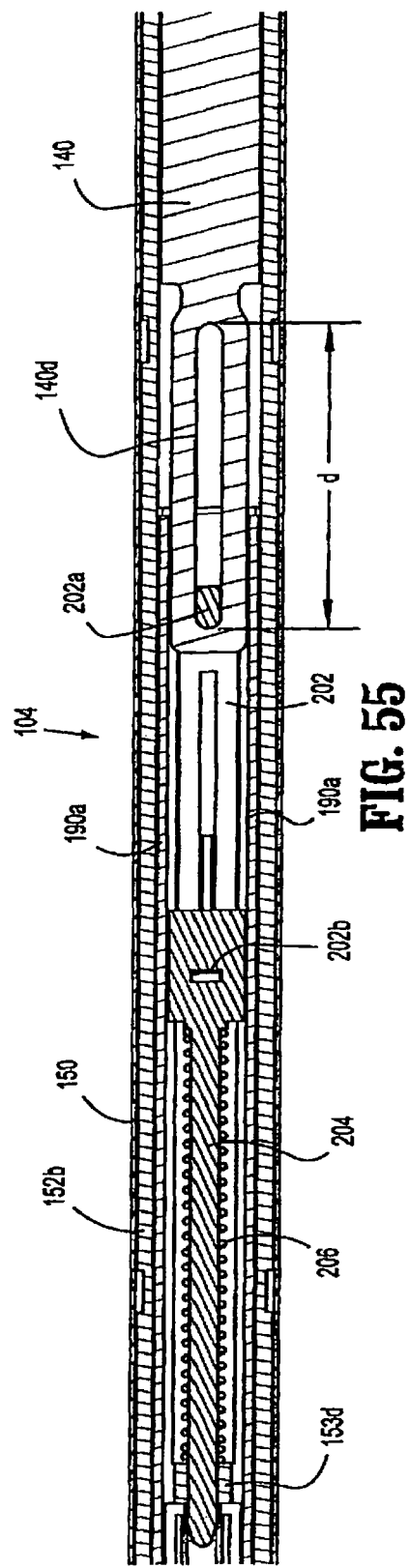

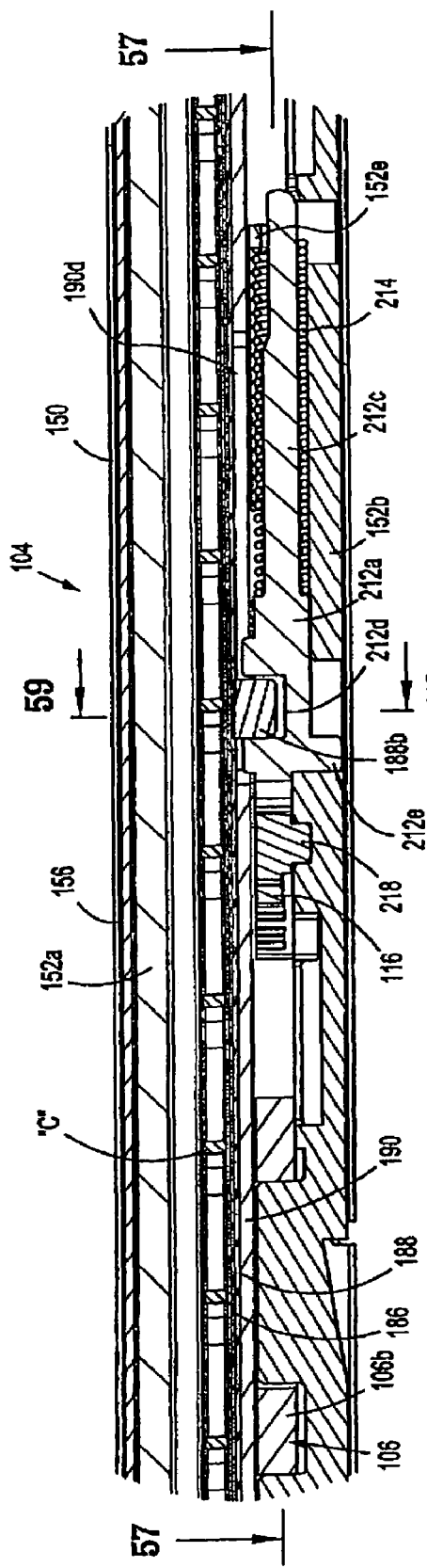
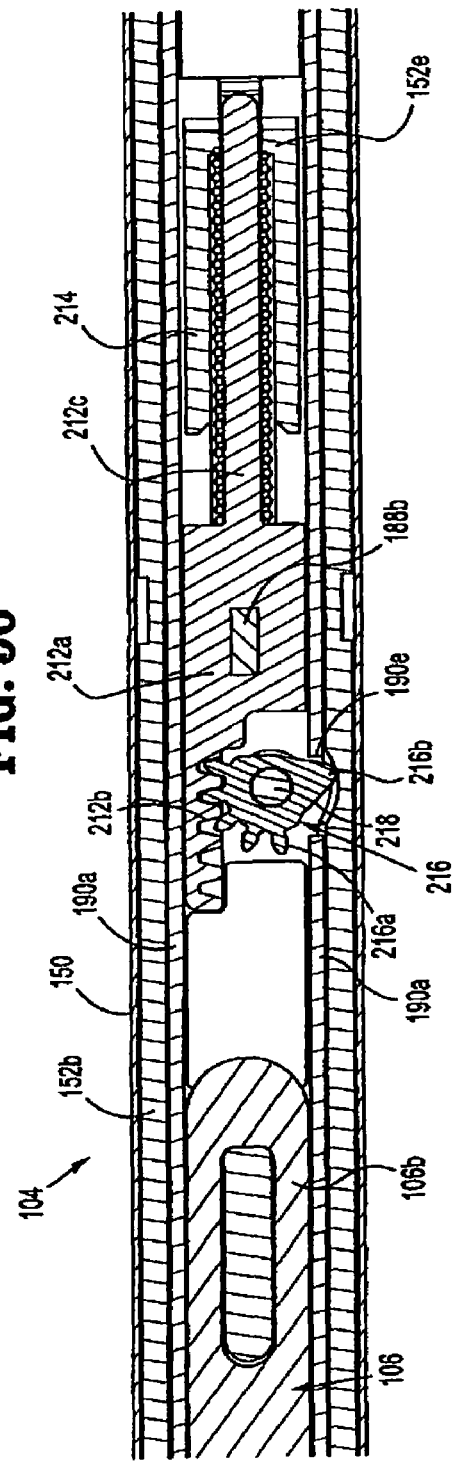
FIG. 56
FIG. 57

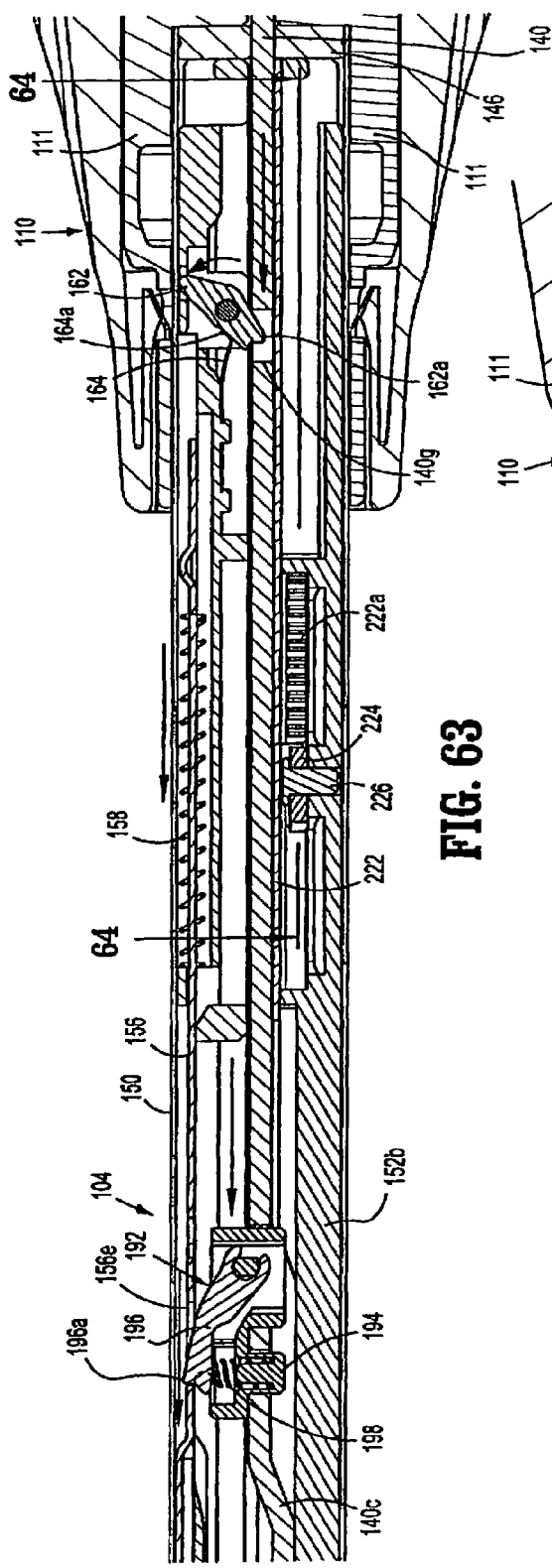
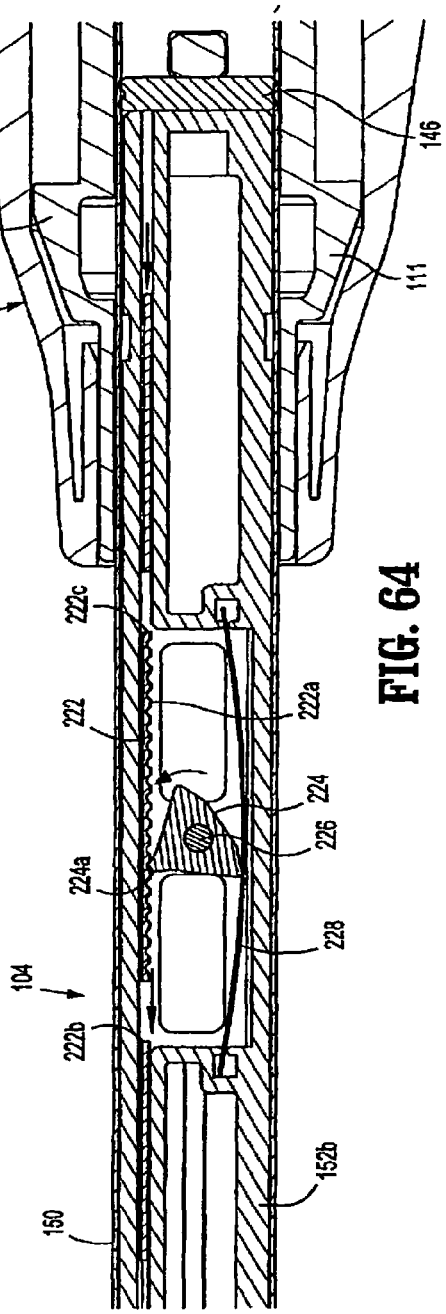
FIG. 63
FIG. 64

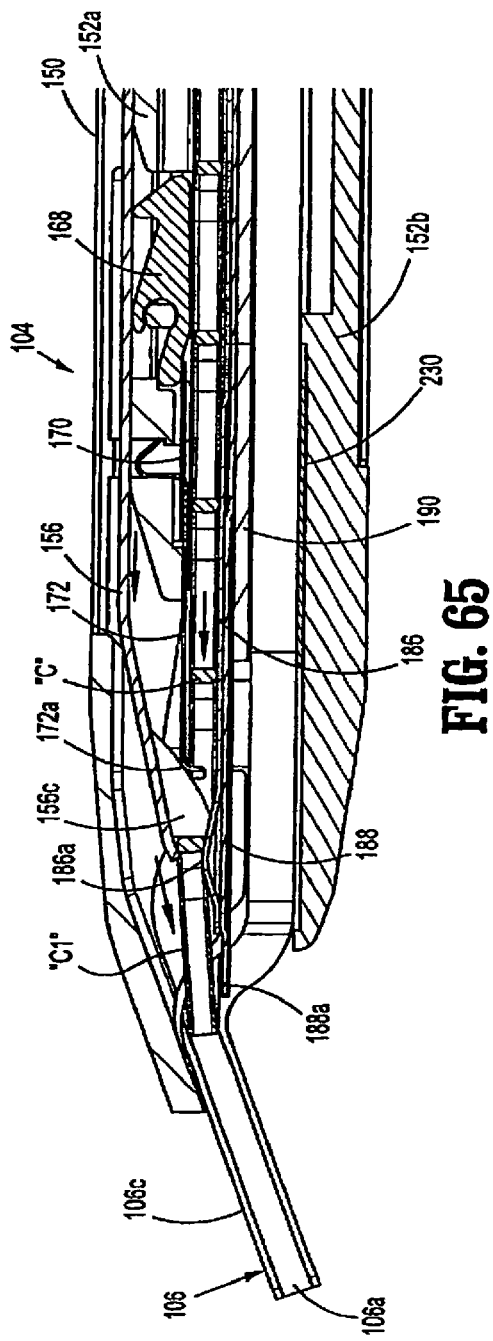
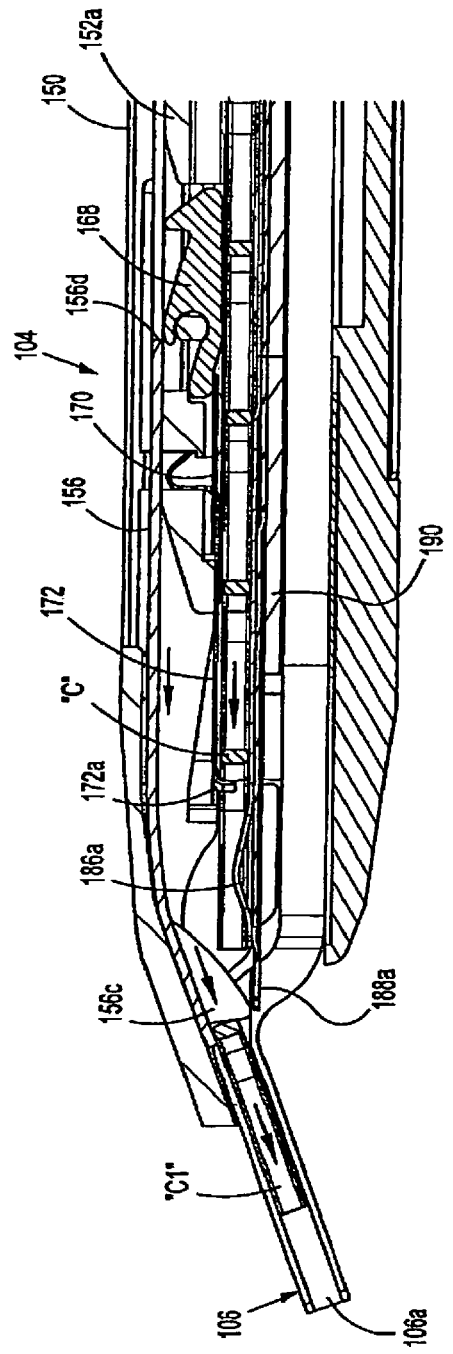
FIG. 65
FIG. 66

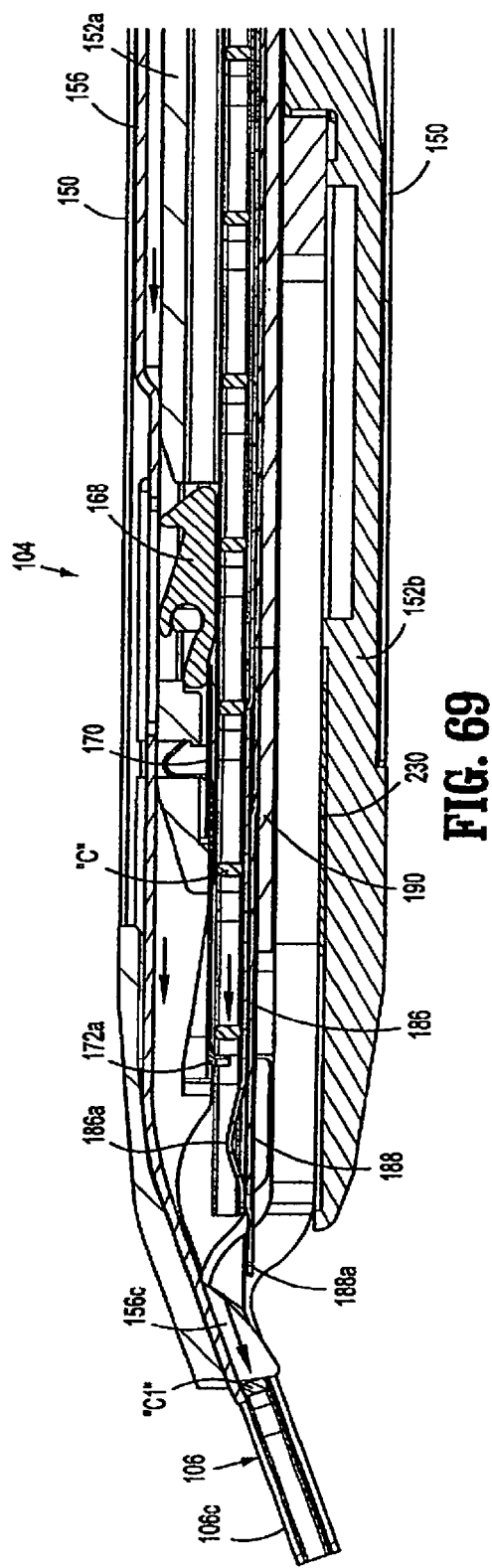
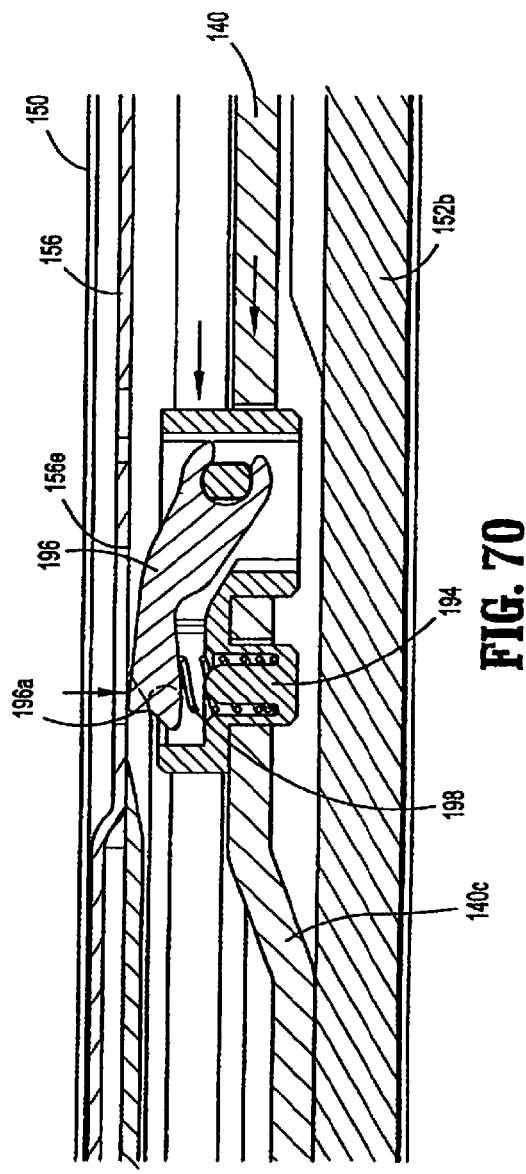
FIG. 69
FIG. 70

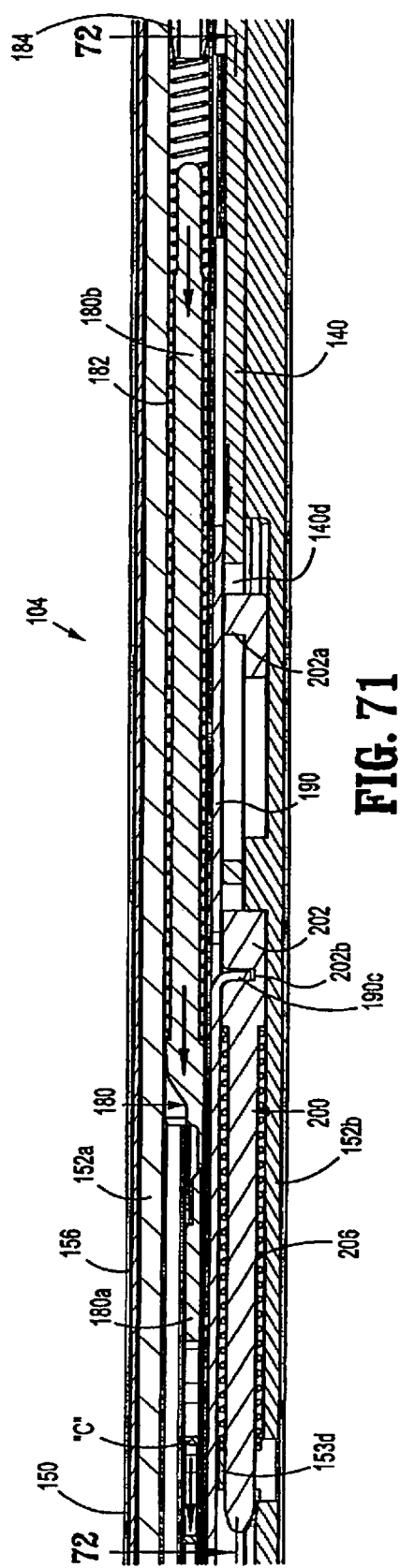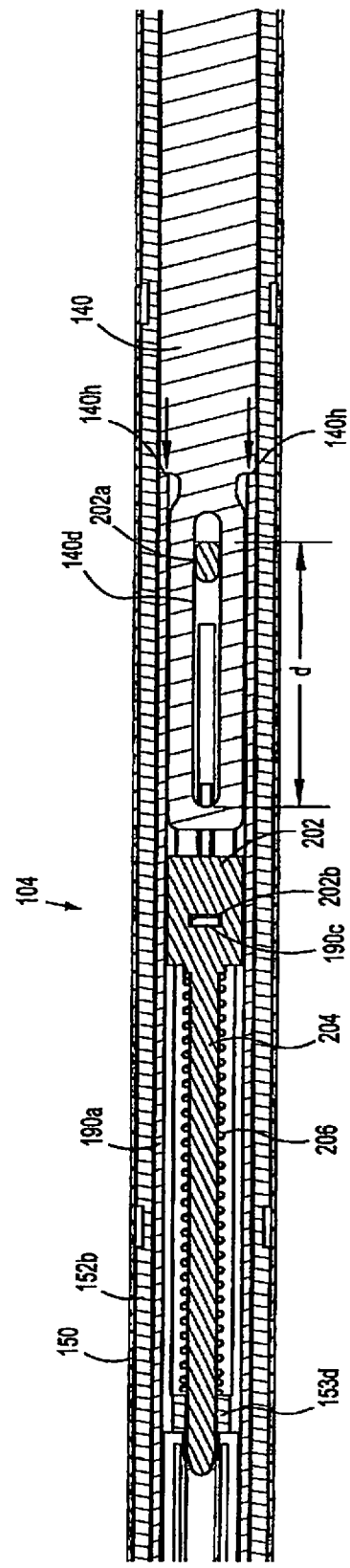

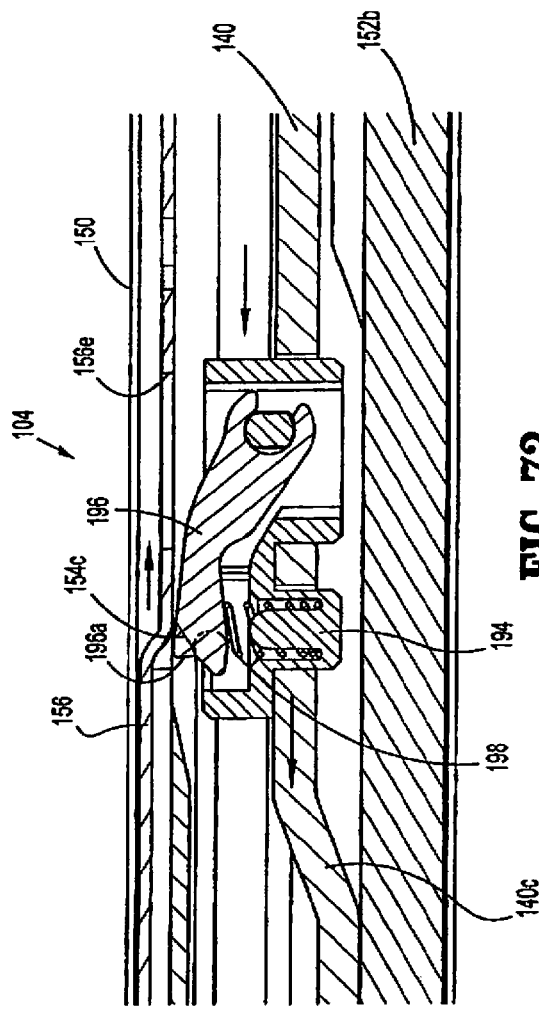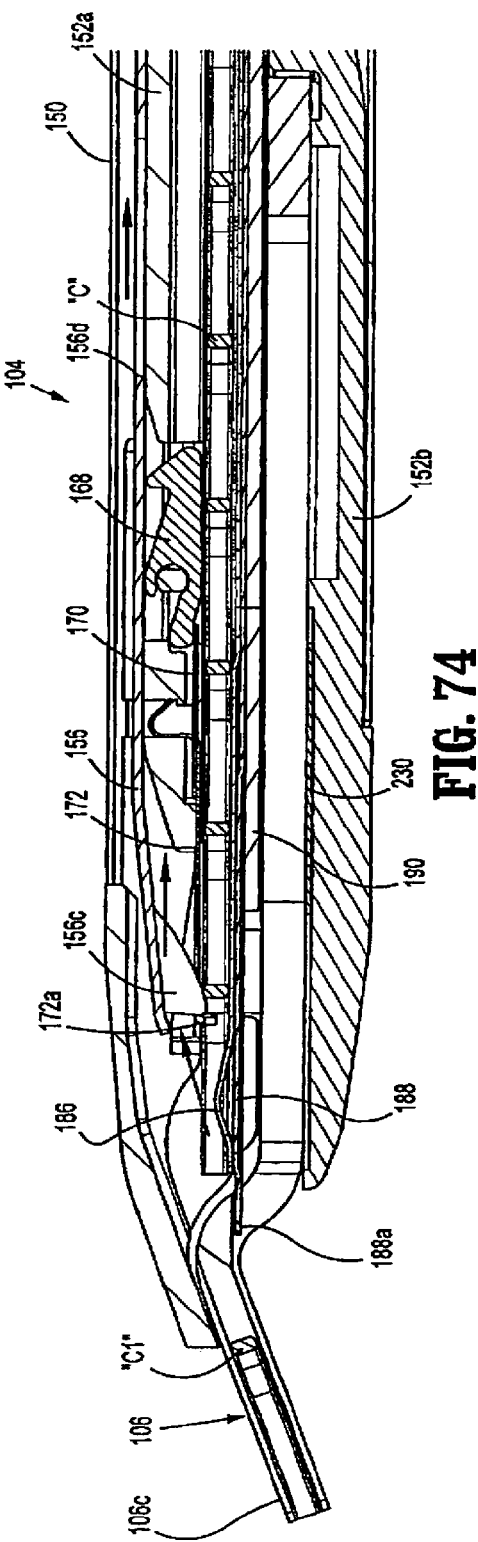

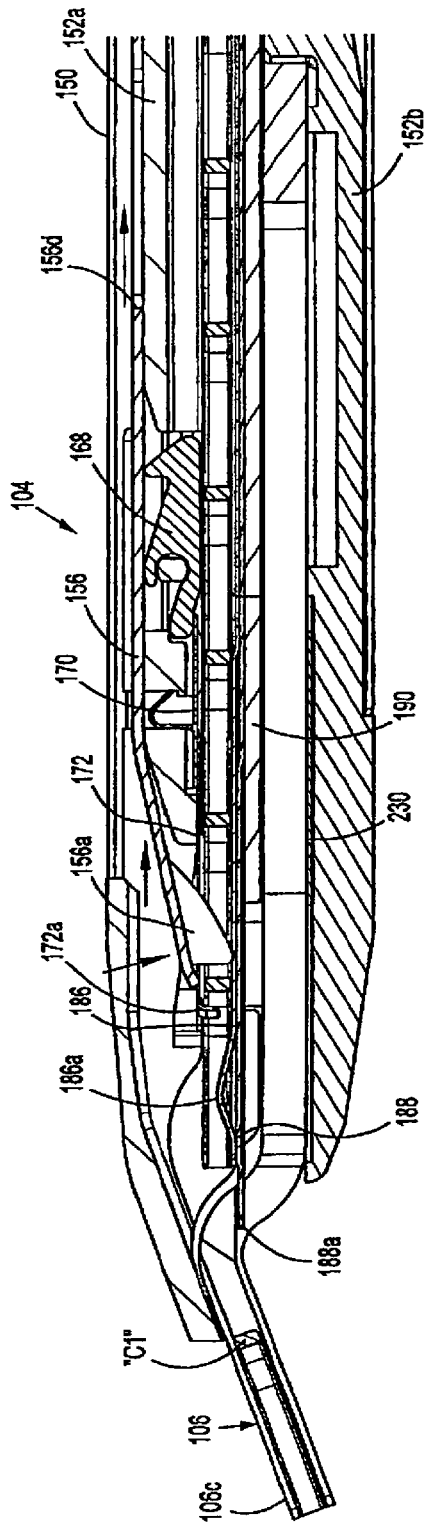
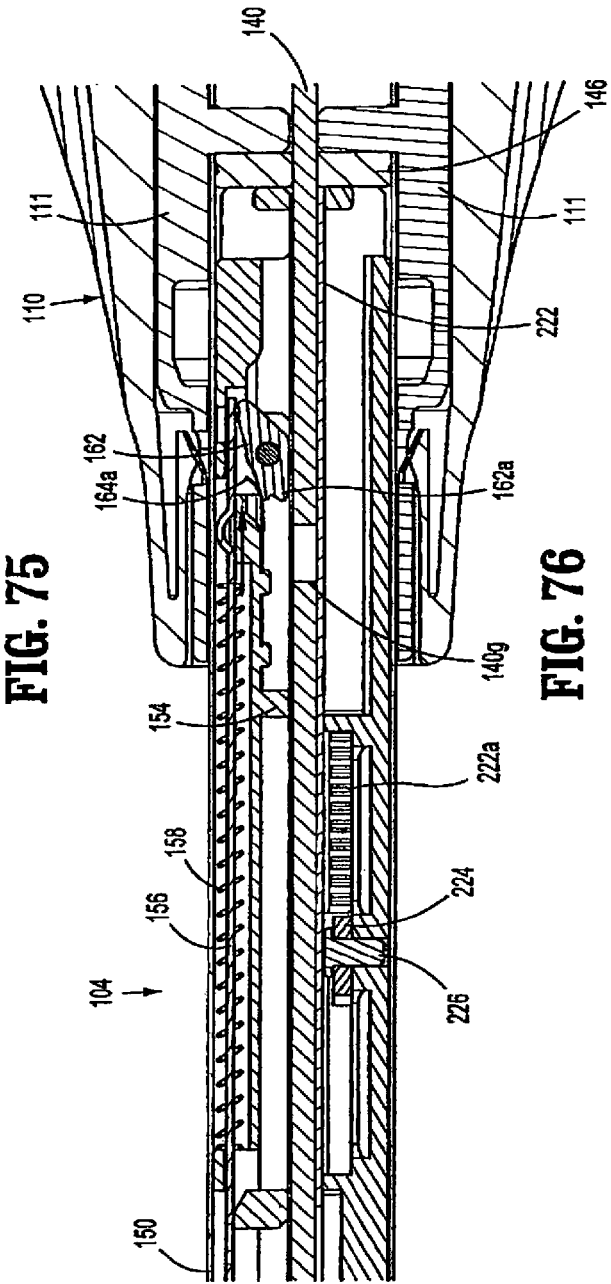
FIG. 75
FIG. 76

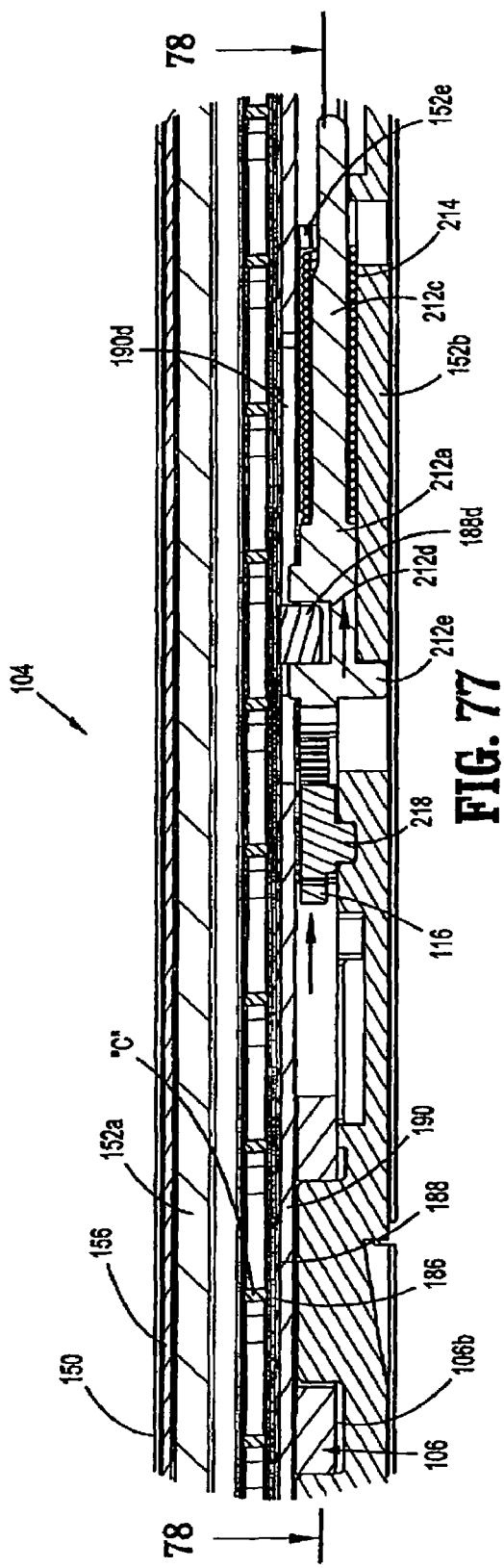
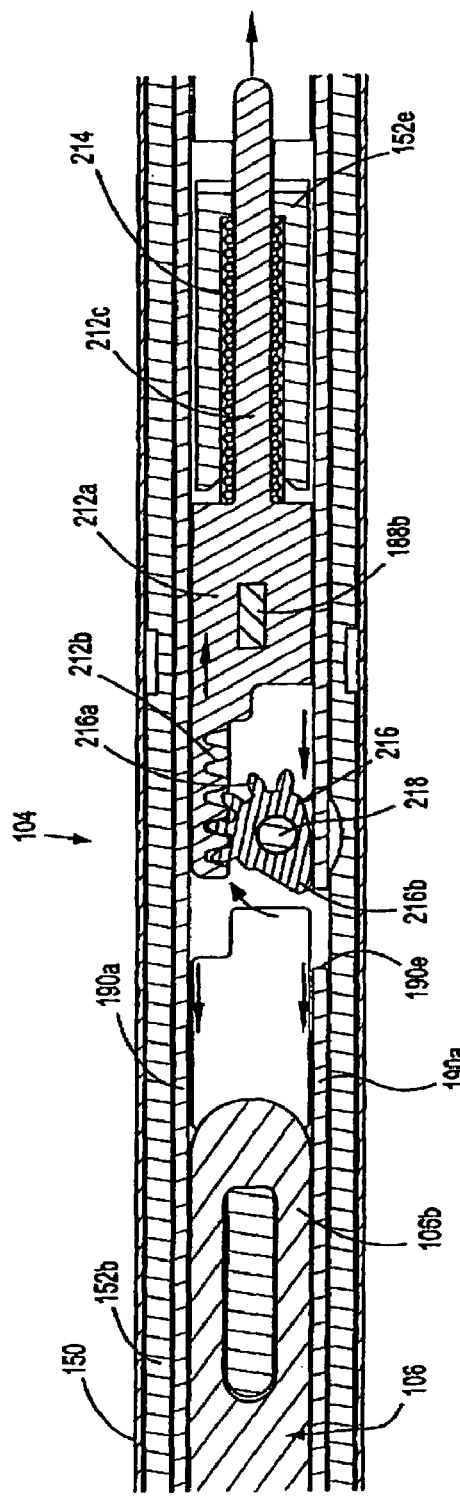

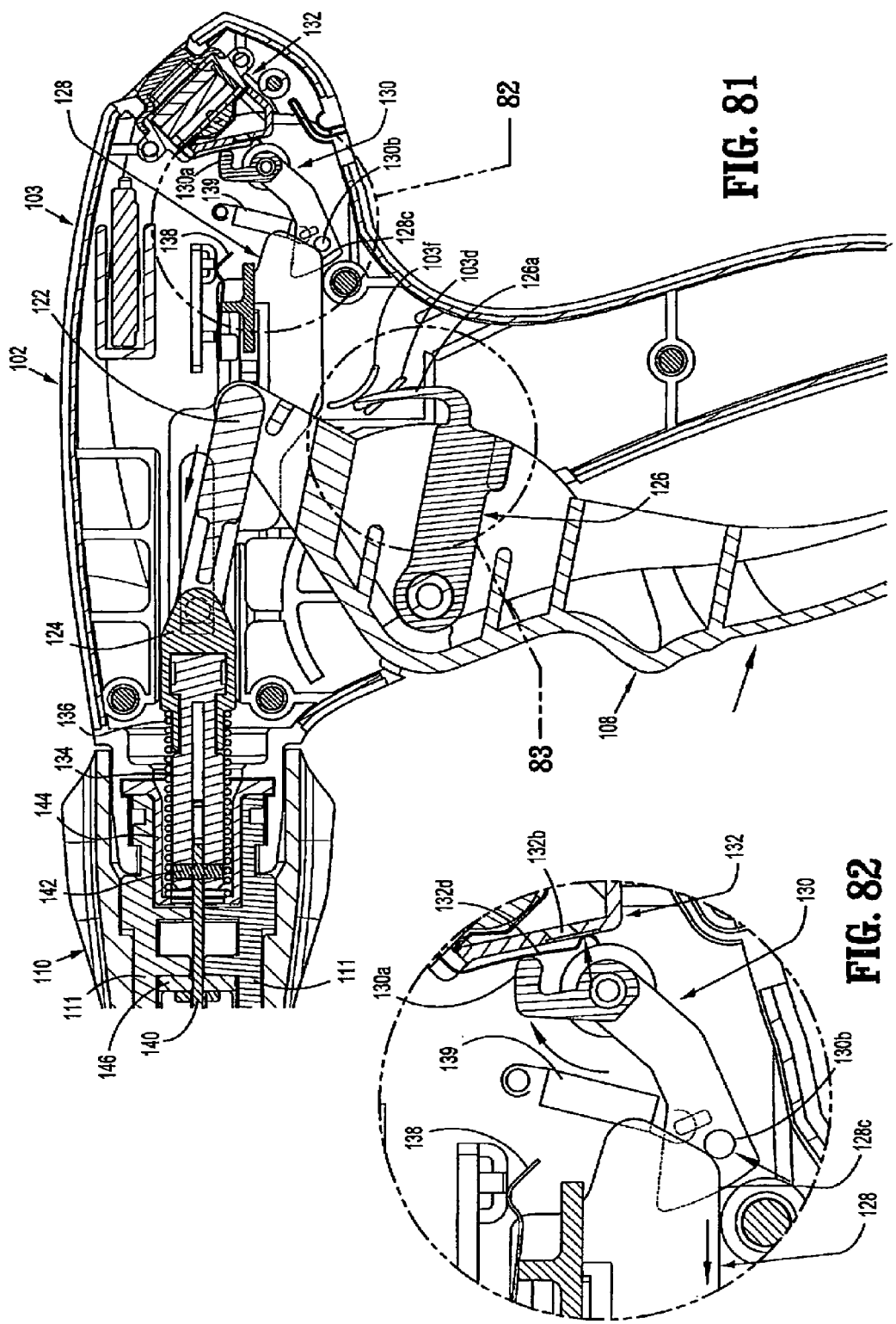

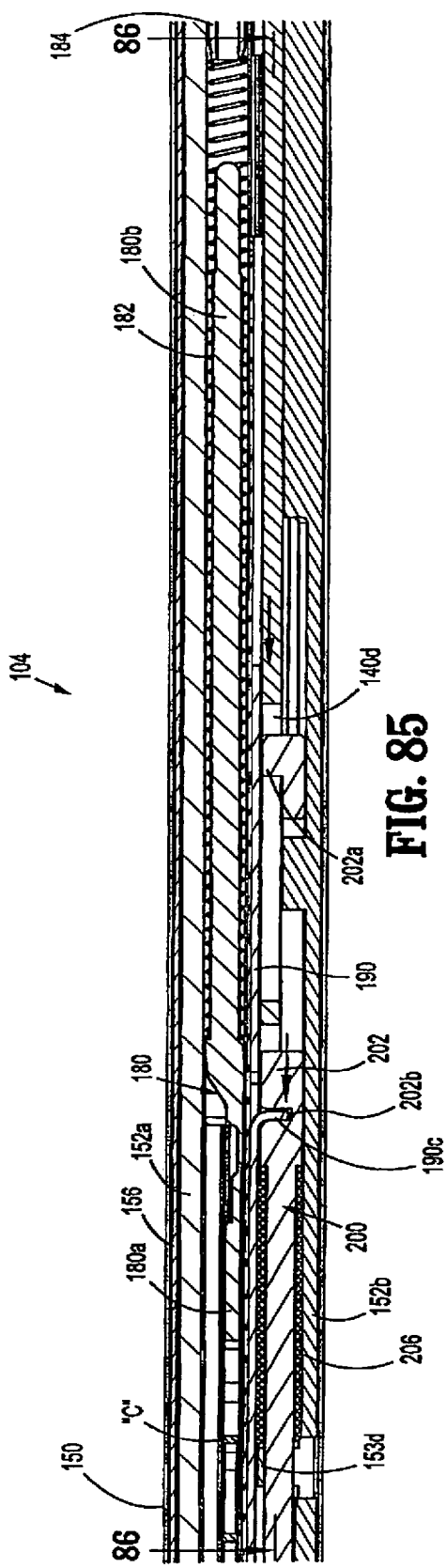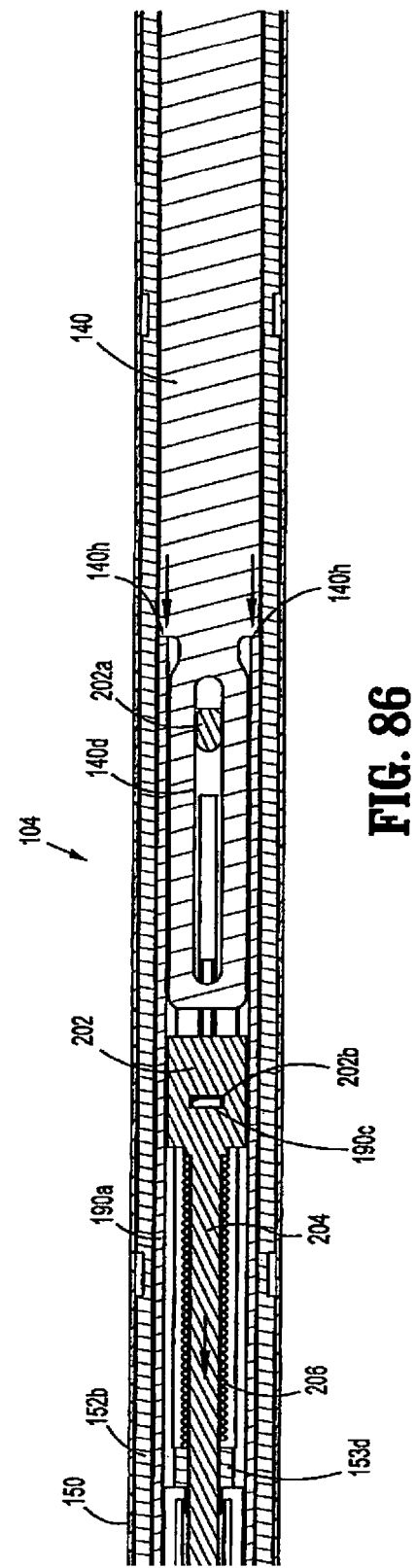

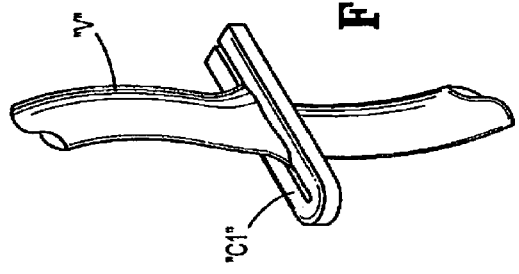
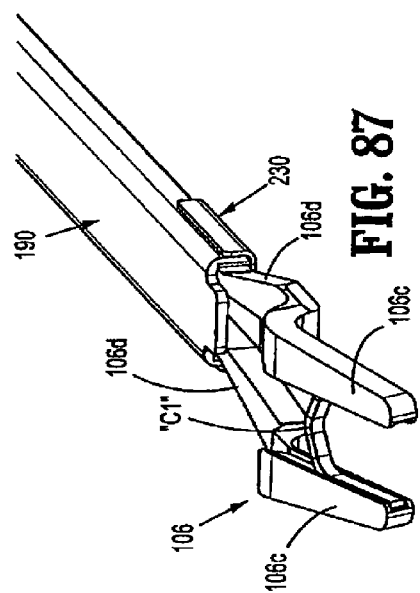
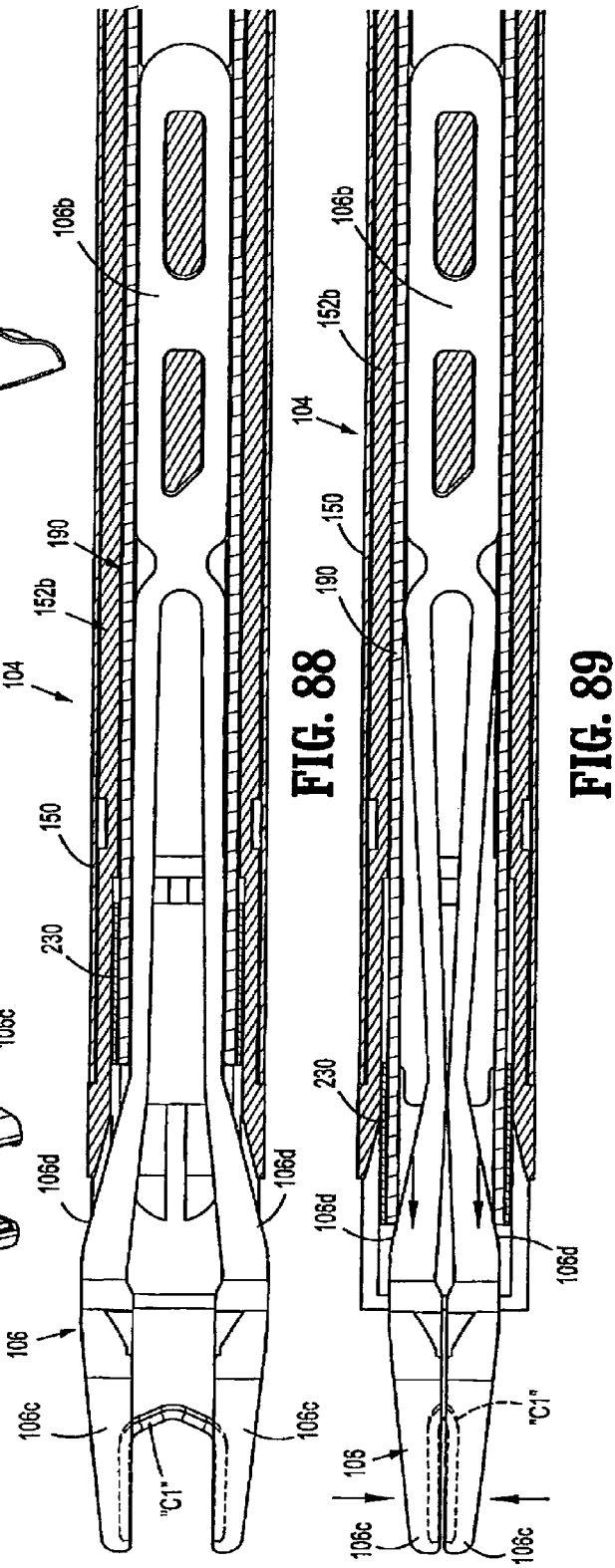
FIG. 87
FIG. 88
FIG. 89
FIG. 90

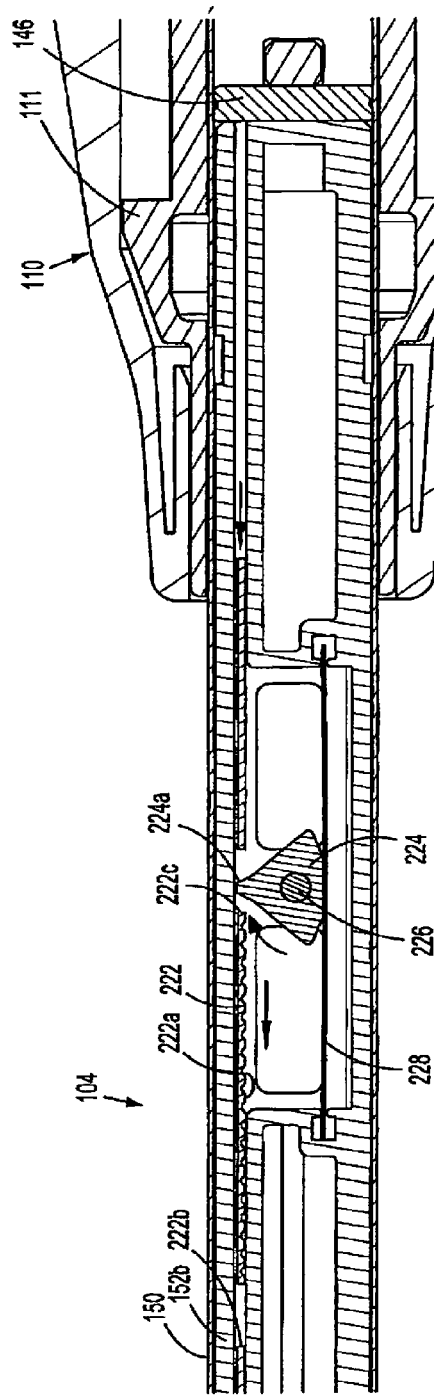
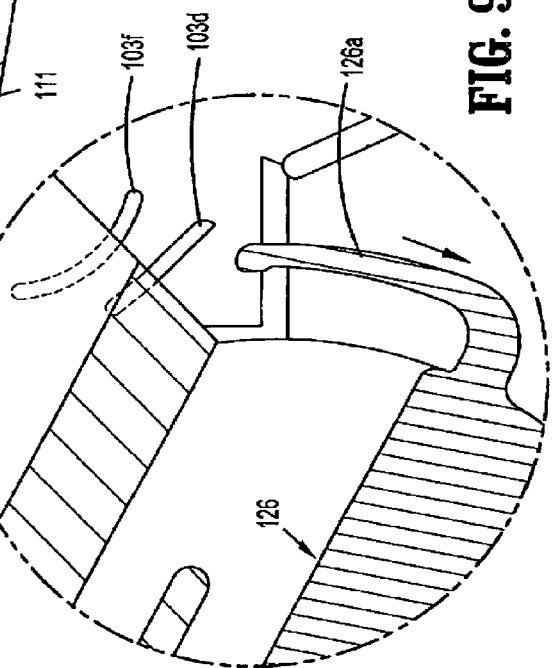
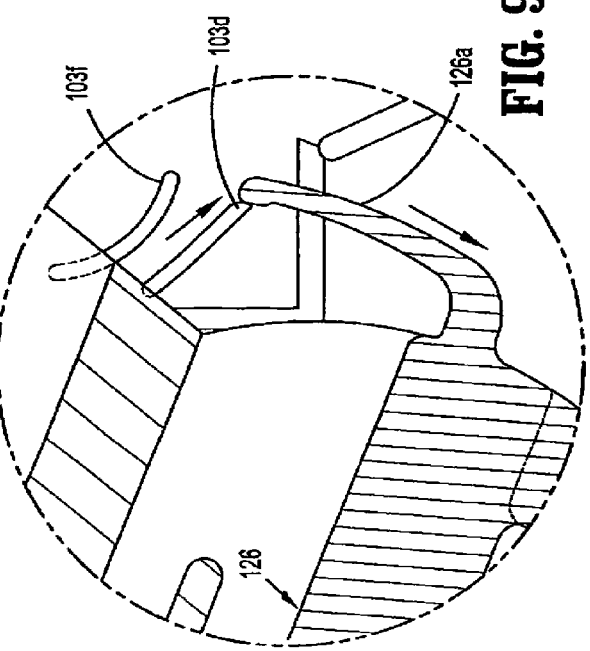

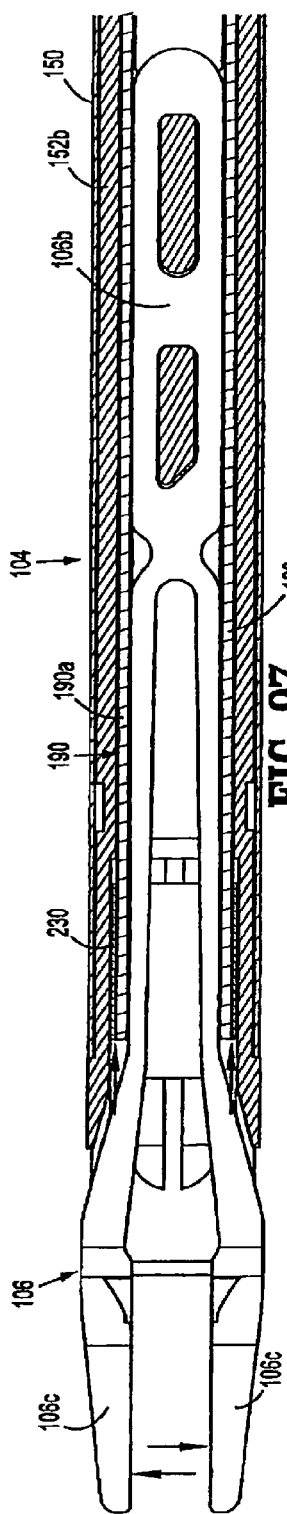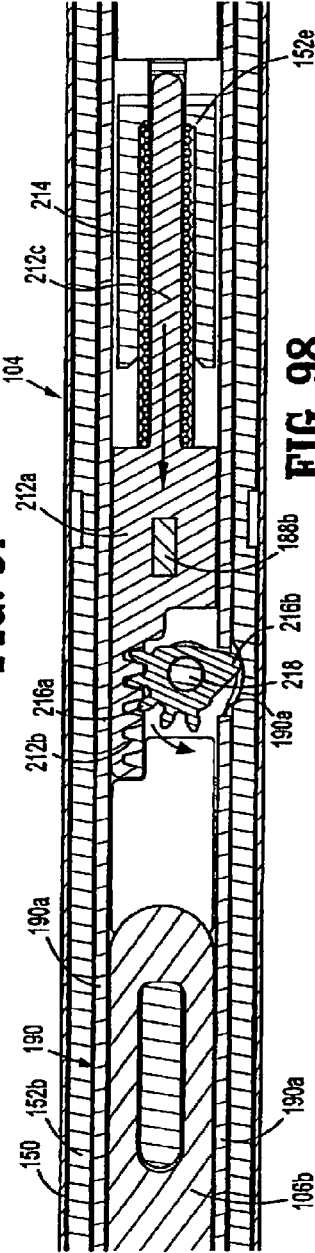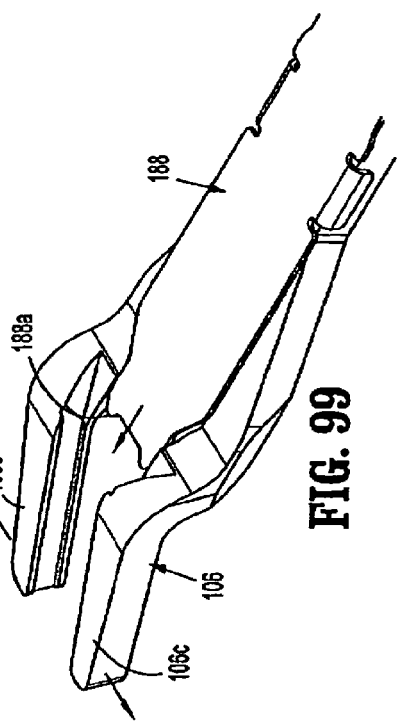

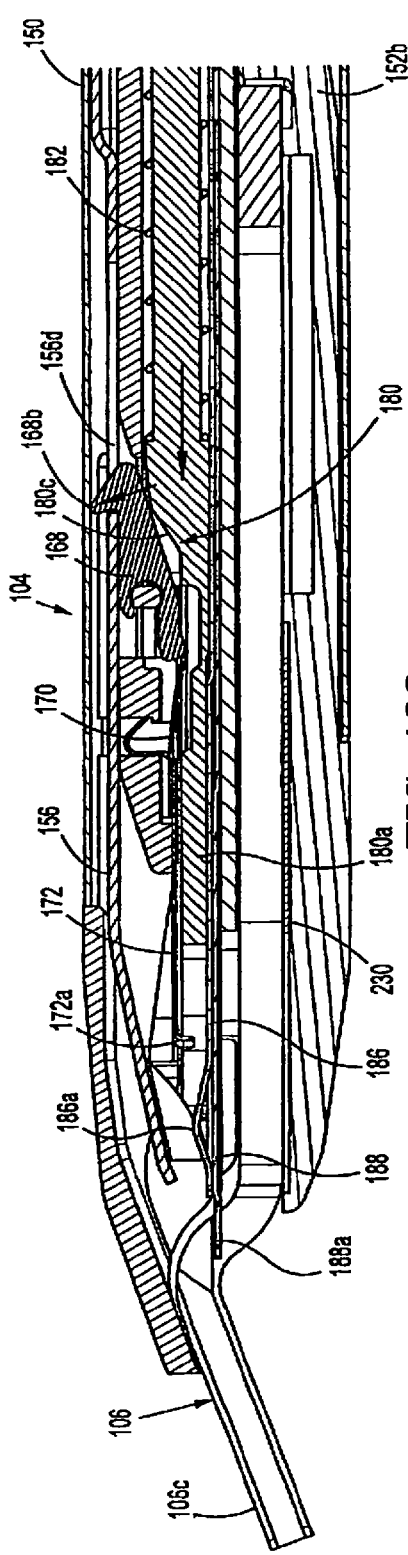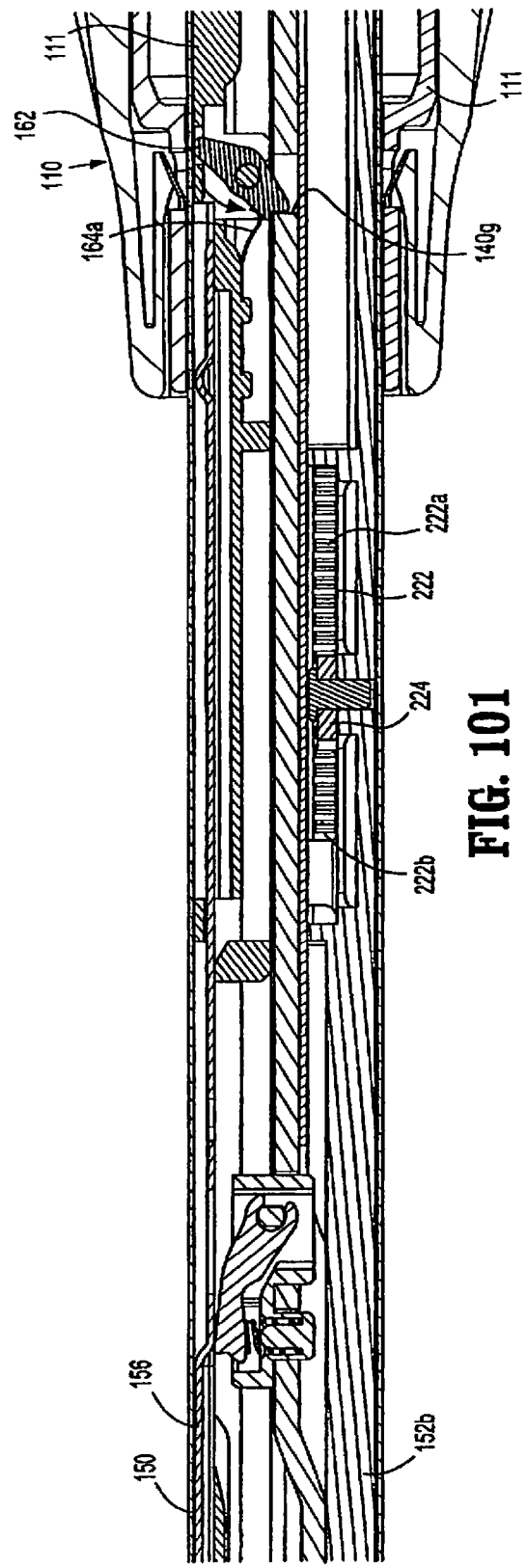

ENDOSCOPIC SURGICAL CLIP APPLIER

CROSS-REFERENCE TO RELATED APPLICATIONS

The present application claims the benefit of and priority to U.S. Provisional Application Ser. No. 60/920,114, filed Mar. 26, 2007, the entire content of which is incorporated herein by reference.

BACKGROUND

1. Technical Field

The technical field relates to surgical clip appliers. More particularly, the present disclosure relates to an endoscopic surgical clip applier having a mechanism for stabilizing the jaw structure during the insertion of a surgical clip.

2. Description of Related Art

Endoscopic staplers and clip appliers are known in the art and are used for a number of distinct and useful surgical procedures. In the case of a laparoscopic surgical procedure, access to the interior of an abdomen is achieved through narrow tubes or cannulas inserted through a small entrance incision in the skin. Minimally invasive procedures performed elsewhere in the body are often generally referred to as endoscopic procedures. Typically, a tube or cannula device is extended into the patient's body through the entrance incision to provide an access port. The port allows the surgeon to insert a number of different surgical instruments therethrough using a trocar and for performing surgical procedures far removed from the incision.

During a majority of these procedures, the surgeon must often terminate the flow of blood or another fluid through one or more vessels. The surgeon will often apply a surgical clip to a blood vessel or another duct to prevent the flow of body fluids therethrough during the procedure. An endoscopic clip applier is known in the art for applying a single clip during an entry to the body cavity. Such clips are typically fabricated from a biocompatible material and are usually compressed over a vessel. Once applied to the vessel, the compressed clip terminates the flow of fluid therethrough.

Endoscopic clip appliers that are able to apply multiple clips in endoscopic or laparoscopic procedures during a single entry into the body cavity are described in commonly-assigned U.S. Pat. Nos. 5,084,057 and 5,100,420 to Green et al., which are both incorporated by reference in their entirety. Another multiple endoscopic clip applier is disclosed in commonly-assigned U.S. Pat. No. 5,607,436 by Pratt et al., the contents of which is also hereby incorporated by reference herein in its entirety. These devices are typically, though not necessarily, used during a single surgical procedure. U.S. patent application Ser. No. 08/515,341 now U.S. Pat. No. 5,695,502 to Pier et al., the disclosure of which is hereby incorporated by reference herein, discloses a resterilizable surgical clip applier. The clip applier advances and forms multiple clips during a single insertion into the body cavity. This resterilizable clip applier is configured to receive and cooperate with an interchangeable clip magazine so as to advance and form multiple clips during a single entry into a body cavity. One significant design goal is that the surgical clip be loaded between the jaws without any compression of the clip from the loading procedure. Such bending or torque of the clip during loading often has a number of unintended consequences. Such compression during loading may alter slightly the alignment of the clip between the jaws. This will cause the surgeon to remove the clip from between the jaws for discarding the clip. Additionally, such preloading compression may slightly compress parts of the clip and change a geometry of the clip. This may require the surgeon to remove the compressed clip from between the jaws for discarding the clip.

Endoscopic or laparoscopic procedures are often performed remotely from the incision. Consequently, application of clips may be complicated by a reduced field of view or reduced tactile feedback for the user at the proximal end of the device. It is therefore desirable to improve the operation of the instrument by providing an indication to the user of a firing of an individual clip, the depletion of the clips contained in the loading unit, or any other surgical event. It is also desirable to provide a surgical clip applier that promotes a successful loading of the clip and that wedges the jaws of the surgical clip applier open, then loads the clip between the jaws, in order to prevent any damage or excessive compression of the clip and prevents compression of the jaws on the clip before firing.

SUMMARY

The present disclosure relates to an endoscopic surgical clip applier.

According to an aspect of the present disclosure, an apparatus for application of surgical clips to body tissue is provided and includes a handle assembly; a shaft assembly extending distally from the handle assembly and defining a longitudinal axis; a plurality of surgical clips disposed within the shaft assembly; jaws mounted adjacent a distal end portion of the shaft assembly, the jaws including a pair of jaw members movable between a spaced-apart and an approximated position; a clip pusher bar configured to individually distally advance a surgical clip to the jaws while the jaw members are in the spaced apart position; a drive bar at least partially disposed within the handle assembly and the shaft assembly, the drive bar being longitudinally movable in response to actuation of a trigger of the handle assembly; and a drive channel positioned adjacent the first and second jaw members to move the jaw members to the approximated position.

The apparatus further includes a lockout system configured to selectively engage the clip pusher bar to prevent the clip pusher bar from returning to a home position and to prevent the trigger from completing a full stroke when the plurality of clips are substantially exhausted.

The lockout system may include a pusher-bar latch mechanism supported in the shaft assembly. In use, a lock-out bar of the latch mechanism may be actuated to engage the clip pusher bar when a final clip is exhausted. The lock-out bar may prevent the clip pusher bar from returning to the home position.

The apparatus may further include a clip follower slidably disposed within the shaft assembly at a location proximal of the plurality of clips. In use, the clip follower may urge the lock-out bar of the pusher-bar latch mechanism into engagement with the clip pusher bar when the final clip is exhausted.

The lockout system may include a rack having a plurality of ratchet teeth and being secured to the drive channel; and a pawl having at least one tooth and being disposed at a location to selectively engage the rack. The pawl may be biased into engagement with the rack. In use, as the drive channel is longitudinally reciprocated, the plurality of teeth may be passed over the pawl, and the pawl may prevent inadvertent return of the drive channel before full actuation of the apparatus.

The apparatus lockout system may include a latch member operatively engageable by the clip pusher bar and the drive channel. The latch member may include a position that is out of engagement with the drive channel when the clip pusher bar is in the home position, and a position that is engaged with the drive channel when the clip pusher bar is in a non-home position. In use, when the clip pusher bar is prevented from returning to the home position by the lock-out bar, the latch member is engaged with the drive channel and prevents the drive channel from moving proximally, whereby the plurality of teeth of the rack are maintained in engagement with the pawl.

The apparatus may further include a wedge plate slidably supported in the shaft assembly. The wedge plate may include a distal end configured and dimensioned for placement between the jaw members when the jaw members are in the spaced-apart position. In use, the wedge plate may be moved in a proximal direction to withdraw the distal end thereof from between the jaw members when the drive channel is moved in a distal direction.

The apparatus may further include a gear operatively disposed between the wedge plate and the drive channel. In use, the gear may translate distal movement of the drive channel into proximal movement of the wedge plate and proximal movement of the drive channel into distal movement of the wedge plate.

The apparatus may be provided with a delay between the distal advancement of the drive bar and the distal advancement of the drive channel.

The apparatus may further include a trip mechanism supported on the drive bar. The trip mechanism may include a trip lever biased into contact with the clip pusher bar. In use, distal movement of the drive bar may move the trip mechanism until the trip lever thereof engages a lip of the clip pusher bar and in turn distally moves the clip pusher bar.

The apparatus may further include a shear pin operatively connected to the drive bar to transmit axial forces to the drive bar during movement of the trigger, wherein the shear pin includes at least one region of reduced strength. The shear pin may fail at the at least one region of reduced strength when a minimum predetermined shear force is exerted on the shear pin.

According to another aspect of the present disclosure, an apparatus for application of surgical clips to body tissue is provided and includes a handle assembly; a shaft assembly extending distally from the handle assembly; a plurality of surgical clips disposed within the shaft assembly, wherein each clip has an outer width; and jaws mounted adjacent a distal end portion of the shaft assembly, wherein the jaws include a pair of jaw members movable between a spaced-apart and an approximated position. The pair of jaw members have an outer width when in the spaced-apart position.

According to yet another aspect of the present disclosure, an apparatus for application of surgical clips to body tissue is provided. The apparatus includes a) a handle assembly; b) a shaft assembly extending distally from the handle assembly; c) a plurality of surgical clips disposed within the shaft assembly, each clip having an outer width; and d) jaws mounted adjacent a distal end portion of the shaft assembly, the jaws including a pair of jaw members movable between a spaced-apart and an approximated position, wherein when the pair of jaw members are in the spaced-apart position the pair of jaw members have an outer width, wherein a ratio of the outer width of the clip to the outer width of the pair of jaw members when in the spaced-apart position in less than or equal to 1:1.8.

According to still another aspect of the present disclosure, a method of applying surgical clips from a surgical clip applier is provided. The method includes the step of providing a surgical clip applier comprising at least a plurality of clips, jaws configured to receive and form said clips, and a trigger configured to actuate the jaws between an open position for receiving said clips and a closed position for forming said clips. The method further includes the steps of actuating the trigger from an open position to a closed position to load a first clip into the jaws and to move the jaws from the open position to the closed position to form said first clip; and then releasing the trigger to return the trigger to the open position and to return the jaws to the open position.

The trigger can only return to the open position after the trigger has been actuated to a fully closed position. The method may further comprise the step of providing a drive bar connected to the trigger, and wherein the step of actuating the trigger from the open position to the closed position may then cause the drive bar to move distally.

The method may further comprise the step of providing a pusher bar selectively connected to the drive bar, and wherein the step of actuating the trigger from the open position to the closed position may then cause the pusher bar to move distally.

The step of moving the pusher bar distally may include the step of a distal end of the pusher bar contacting a backspan of a distalmost clip and then moving the distalmost clip to a position between into the jaws. The method may further comprise the step of then disengaging the drive bar from the pusher bar, whereby the drive bar continues to move distally.

The method may further comprise the step of simultaneously moving a remainder of clips in a distal direction as said distalmost clip is moved into the jaws.

The method may further comprise the step of the drive bar then engaging a drive channel to move the drive channel in a distal direction.

The method may further comprise the step of then moving the pusher bar in a proximal direction.

The method may further comprise the step of then moving a wedge plate in a proximal direction such that a distal end of the wedge plate is withdrawn from between the jaws.

The method may further comprise the step of then engaging a distal end of the drive channel against the jaws to move the jaws from the open position to the closed position to from the clip disposed therein.

The method may further comprise the step of actuating a counter mechanism to indicate that an event has occurred.

The method may further comprise the step of then releasing the trigger to move the drive bar and drive channel in a proximal direction and to move the wedge plate in a distal direction.

The method may further comprise the step of actuating a lock member, following placement of a final clip into the jaws, that engages the pusher bar and prevents the pusher bar from moving to a fully proximal position.

DESCRIPTION OF THE DRAWINGS

A particular embodiment of a surgical clip applier is disclosed herein with reference to the drawings wherein:

FIG. 2 is a further perspective view of the surgical clip applier of FIG. 1, illustrating a rotation of an elongate tubular member thereof;

FIG. 3 is an enlarged, perspective view of the jaw structure of the surgical clip applier of FIGS. 1 and 2;

FIG. 4A is a top view of a surgical clip applier having a first overall length;

FIG. 4 is a top view of the surgical clip applier of FIGS. 1-3, having a second overall length;

FIG. 5 is a side view of the surgical clip applier of FIGS. 1-4;

FIG. 18 is a rear, perspective, cross-sectional view of the surgical clip applier of FIGS. 1-4, as taken through 18-18 of FIG. 5;

FIG. 19 is an enlarged view of the indicated area of detail of FIG. 18;

FIG. 20 is a rear, elevational, cross-sectional view of the surgical clip applier of FIGS. 1-4, as taken through 20-20 of FIG. 5;

FIG. 21 is a front, perspective view of the shaft assembly of the surgical clip applier of FIGS. 1-4, with an outer tubular member removed therefrom for illustrative purposes;

FIG. 22 is an enlarged, perspective view of the indicated area of detail of FIG. 21;

FIG. 23 is an enlarged, perspective view of the indicated area of detail of FIG. 21;

FIG. 24 is a front, perspective view of the shaft assembly of the surgical clip applier of FIGS. 1-4, with an upper housing removed therefrom for illustrative purposes;

FIG. 25 is an enlarged, perspective view of the indicated area of detail of FIG. 24;

FIG. 26 is an enlarged, perspective view of the indicated area of detail of FIG. 24;

FIG. 27 is an enlarged, perspective view of a distal end of the shaft assembly of FIG. 24;

FIG. 28 is a rear, perspective view of the shaft assembly of the surgical clip applier of FIGS. 1-4, with a pusher bar, a clip advance mechanism and a plurality of clips removed therefrom;

FIG. 29 is an enlarged, perspective view of the indicated area of detail of FIG. 28;

FIG. 30 is an enlarged, perspective view of the indicated area of detail of FIG. 28;

FIG. 31 is a front, perspective view of the shaft assembly of the surgical clip applier of FIGS. 1-4, with a lower housing pusher bar, a clip advance mechanism and a plurality of clips removed therefrom;

FIG. 32 is an enlarged, perspective view of the indicated area of detail of FIG. 31;

FIG. 33 is a perspective view of the indicated area of detail of FIG. 31;

FIG. 34 is a bottom, front, perspective view of the shaft assembly of the surgical clip applier of FIGS. 1-4, with a lower housing removed therefrom;

FIG. 35 is an enlarged, perspective view of the indicated area of detail of FIG. 34;

FIG. 36 is an enlarged, perspective view of the indicated area of detail of FIG. 34;

FIG. 37 is a rear, perspective view of the shaft assembly of the surgical clip applier of FIGS. 1-4, with a drive channel and wedge plate removed therefrom;

FIG. 38 is an enlarged, perspective view of the indicated area of detail of FIG. 34;

FIG. 39 is a bottom, front, perspective view of the distal end of the shaft assembly of the surgical clip applier of FIGS. 1-4, illustrating the upper housing, the wedge plate and a drive channel in an assembled condition;

FIG. 40 is an enlarged, rear perspective view of a pawl and rack assembly of the shaft assembly with the drive bar removed;

FIG. 41 is an enlarged, perspective view of the indicated area of detail of FIG. 39;

FIG. 42 is an enlarged, perspective view of the indicated area of detail of FIG. 39;

FIG. 43 is a bottom, front, perspective view of the distal end of the shaft assembly of FIG. 39, with the wedge plate and the drive channel, clip stack and follower removed therefrom;

FIG. 44 is an enlarged, perspective view of the indicated area of detail of FIG. 43;

FIG. 45 is an enlarged, perspective view of the indicated area of detail of FIG. 43;

FIG. 46 is an enlarged, perspective view of the indicated area of detail of FIG. 43;

FIG. 52 is an enlarged, elevational, cross-sectional view of the indicated area of detail of FIG. 49;

FIG. 53 is a longitudinal, cross-sectional view taken through 53-53 of FIG. 52;

FIG. 54 is an enlarged, elevational, cross-sectional view of the indicated area of detail of FIG. 49;

FIG. 55 is a longitudinal, cross-sectional view taken through 55-55 of FIG. 54;

FIG. 56 is an enlarged, elevational, cross-sectional view of the indicated area of detail of FIG. 49;

FIG. 57 is a longitudinal, cross-sectional view taken through 57-57 of FIG. 56;

FIG. 63 is an enlarged, elevational, cross-sectional view of the of detail 52 of FIG. 49, during the first stage of the initial stroke of the trigger of the handle assembly;

FIG. 64 is a longitudinal, cross-sectional view taken through 64-64 of FIG. 63;

FIGS. 65 and 66 are enlarged, elevational, cross-sectional views of detail 60 of FIG. 49, during the first stage of the initial stroke of the trigger of the handle assembly;

FIG. 69 is an enlarged, elevational, cross-sectional view of detail 60 of FIG. 49, during the second stage of the initial stroke of the trigger of the handle assembly;

FIG. 70 is an enlarged, elevational, cross-sectional view of detail 52 of FIG. 49, during the second stage of the initial stroke of the trigger of the handle assembly;

FIG. 71 is an enlarged, elevational, cross-sectional view of detail 54 of FIG. 49, during the second stage of the initial stroke of the trigger of the handle assembly;

FIG. 72 is a longitudinal, cross-sectional view taken through 72-72 of FIG. 71;

FIG. 73 is an enlarged, elevational, cross-sectional view of detail 52 of FIG. 49, during the second stage of the initial stroke of the trigger of the handle assembly;

FIGS. 74 and 75 are enlarged, elevational, cross-sectional views of detail 60 of FIG. 49, during the second stage of the initial stroke of the trigger of the handle assembly;

FIG. 76 is an enlarged, elevational, cross-sectional view of the of detail 52 of FIG. 49, during the second stage of the initial stroke of the trigger of the handle assembly;

FIG. 77 is an enlarged, elevational, cross-sectional view of the detail 56 of FIG. 49, during the second stage of the initial stroke of the trigger of the handle assembly;

FIG. 78 is a longitudinal, cross-sectional view taken through 78-78 of FIG. 77;

FIG. 81 is a longitudinal, elevational, cross-sectional view of the handle assembly of the surgical clip applier of FIGS. 1-4, illustrating a third stage of an initial stroke of the trigger of the handle assembly;

FIG. 82 is an enlarged, elevational, cross-sectional view of the indicated area of detail of FIG. 81;

FIG. 85 is an enlarged, elevational, cross-sectional view of detail 54 of FIG. 49, during third stage of the initial stroke of the trigger of the handle assembly;

FIG. 86 is a longitudinal, cross-sectional view taken through 86-86 of FIG. 85;

FIG. 87 is a front, perspective view of the jaws of the surgical clip applier illustrating a drive channel and a drive plate operatively associated therewith;

FIG. 88 is a longitudinal, top-plan, cross-sectional view of a distal end of the shaft assembly of the surgical stapling device of FIGS. 1-4, illustrating an un-approximated position of the jaws;

FIG. 89 is a longitudinal, top-plan, cross-sectional view of a distal end of the shaft assembly of the surgical stapling device of FIGS. 1-4, illustrating an approximated position of the jaws;

FIG. 90 is a perspective view of the body vessel including a clip of the surgical stapling device of FIGS. 1-4, applied thereto;

FIG. 91 is a longitudinal, cross-sectional view taken through 64-64 of FIG. 63, illustrating an operation the pawl and rack assembly of FIG. 40;

FIGS. 92 and 93 are enlarged, elevational, cross-sectional views of detail 83 of FIG. 81, illustrating the operation of the tactile feedback element;

FIG. 97 is a longitudinal, top-plan, cross-sectional view of a distal end of the shaft assembly of the surgical stapling device of FIGS. 1-4, illustrating the un-approximation of the jaws during the release stoke of the trigger of the handle assembly;

FIG. 98 is a longitudinal, cross-sectional view taken through 78-78 of FIG. 77, illustrating the operation of the wedge plate rack mechanism during the release stoke of the trigger handle assembly;

FIG. 99 is a rear, perspective view of the jaws of the surgical clip applier illustrating the wedge plate being inserted therebetween;

FIG. 100 is an enlarged, elevational, cross-sectional view of detail 60 of FIG. 49, beginning a lockout phase after the final clip has been fired;

FIG. 101 is an enlarged, elevational, cross-sectional view of the of detail 52 of FIG. 49, during the release stroke of the trigger of the handle assembly and engaging a lockout mechanism;

DETAILED DESCRIPTION OF EMBODIMENTS

Figure 1:
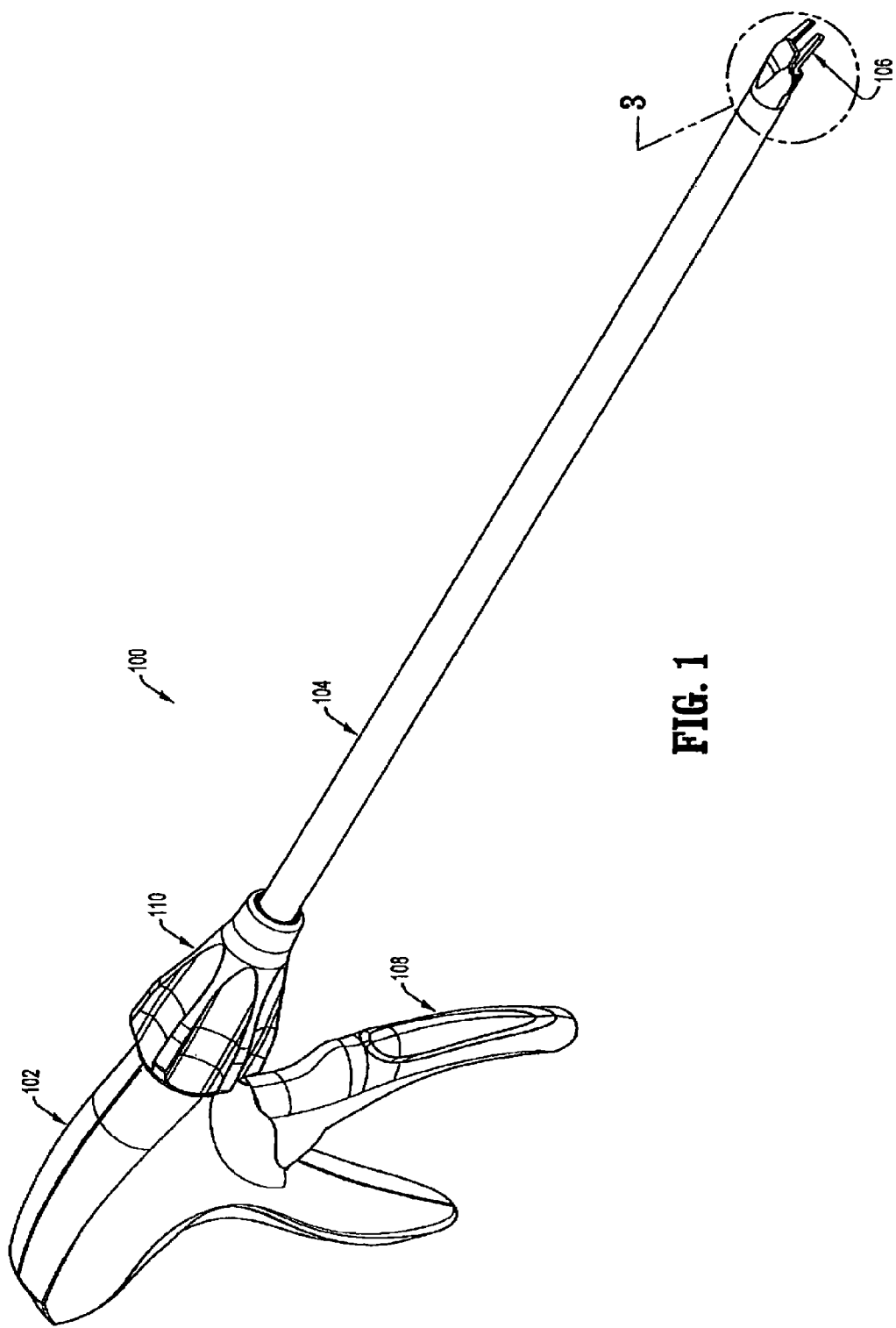
FIG. 1 is a perspective view of a surgical clip applier.

Embodiments of surgical clip appliers in accordance with the present disclosure will now be described in detail with reference to the drawing figures wherein like reference numerals identify similar or identical structural elements. As shown in the drawings and described throughout the following description, as is traditional when referring to relative positioning on a surgical instrument, the term "proximal" refers to the end of the apparatus which is closer to the user and the term "distal" refers to the end of the apparatus which is further away from the user.

Referring now to FIGS. 1-5, a surgical clip applier in accordance with an embodiment of the present disclosure is generally designated as 100. Surgical clip applier 100 generally includes a handle assembly 102 and an endoscopic portion including a shaft assembly 104 extending distally from handle assembly 102.

Shaft assembly 104 may have various outer diameters such as, for example, about 5 mm or about 10 mm, depending on intended use. Further, shaft assembly 104 may have various elongated (see FIG. 4A) or shortened lengths (see FIGS. 4 and 5) depending on intended use, such as, for example, in bariatric surgery. In one embodiment, in bariatric surgery, elongated tubular member 104 may have a length of between about 30 cm and about 40 cm. However one skilled in the art should appreciate that shaft assembly 104 may have any length in excess of about 30 cm and the present disclosure is not limited to any of the above identified lengths.

Surgical clip applier 100 includes a pair of jaws 106 mounted on a distal end of shaft assembly 104 and actuatable by a trigger 108 of handle assembly 102. Jaws 106 are formed of a suitable biocompatible material such as, for example, stainless steel or titanium. Notably, in some embodiments, when jaws 106 are in an open or un-approximated condition relative to each other, a maximum width of jaws 106 measures substantially less than or equal to an outer diameter of shaft assembly 104 to allow for insertion of a distal end of surgical clip applier 100 through a trocar during endoscopic surgery or an opening or orifice in a body during open surgery.

Jaws 106 are mounted in the distal end of shaft assembly 104 such that they are longitudinally stationary relative thereto. A knob 110 may be rotatably mounted on a distal end of handle assembly 102 and affixed to shaft assembly 104 to transmit and/or provide 360° rotation to shaft assembly 104 and jaws 106 about a longitudinal axis thereof (see FIG. 2). Referring momentarily to FIG. 3, jaws 106 define a channel 106a therebetween for receipt of a surgical clip (not shown) therein.

Figure 6:
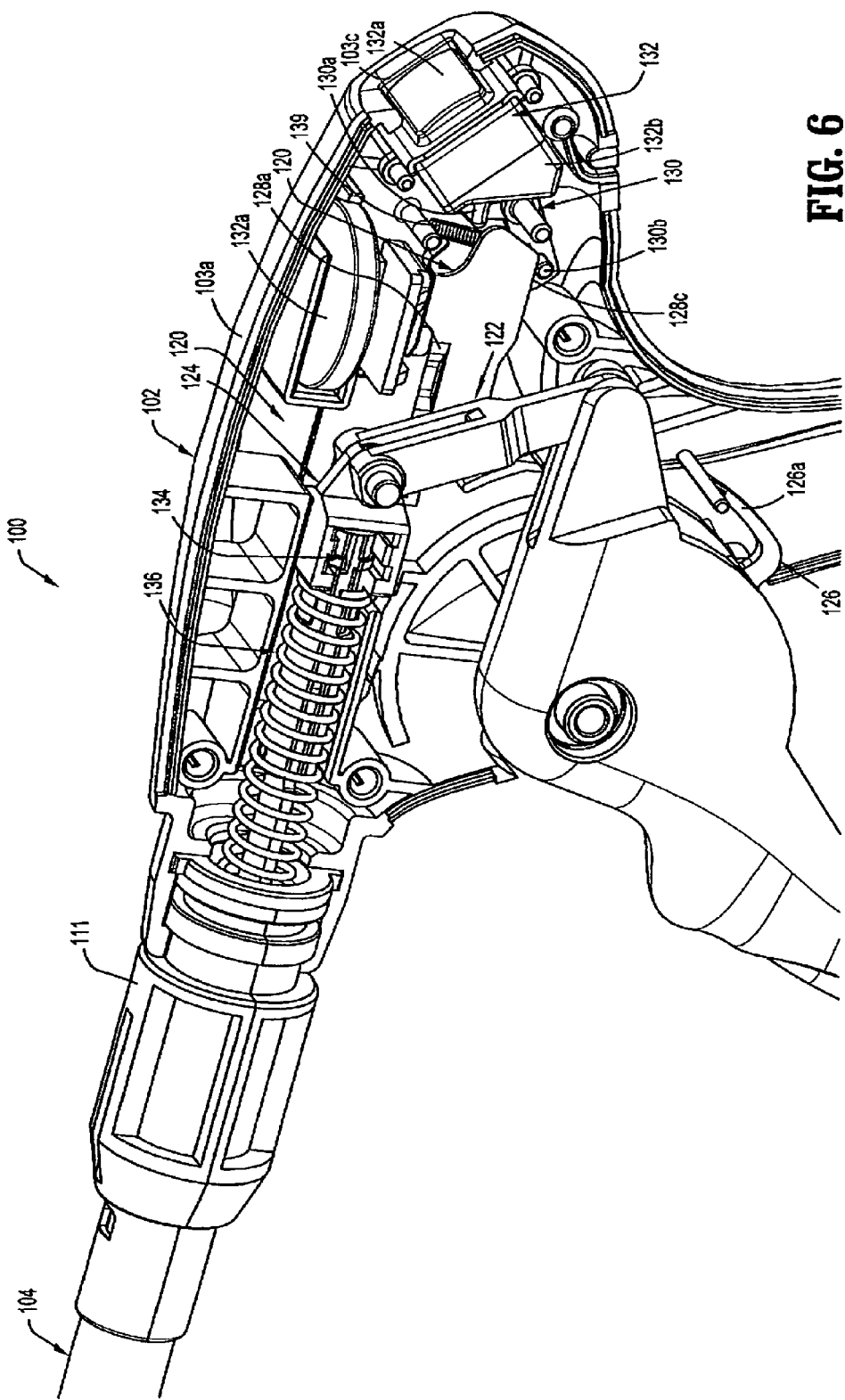
FIG. 6 is a left-side, perspective view of a handle assembly of the surgical clip applier of FIGS. 1-4, with a half of the body removed therefrom.
Figure 7:
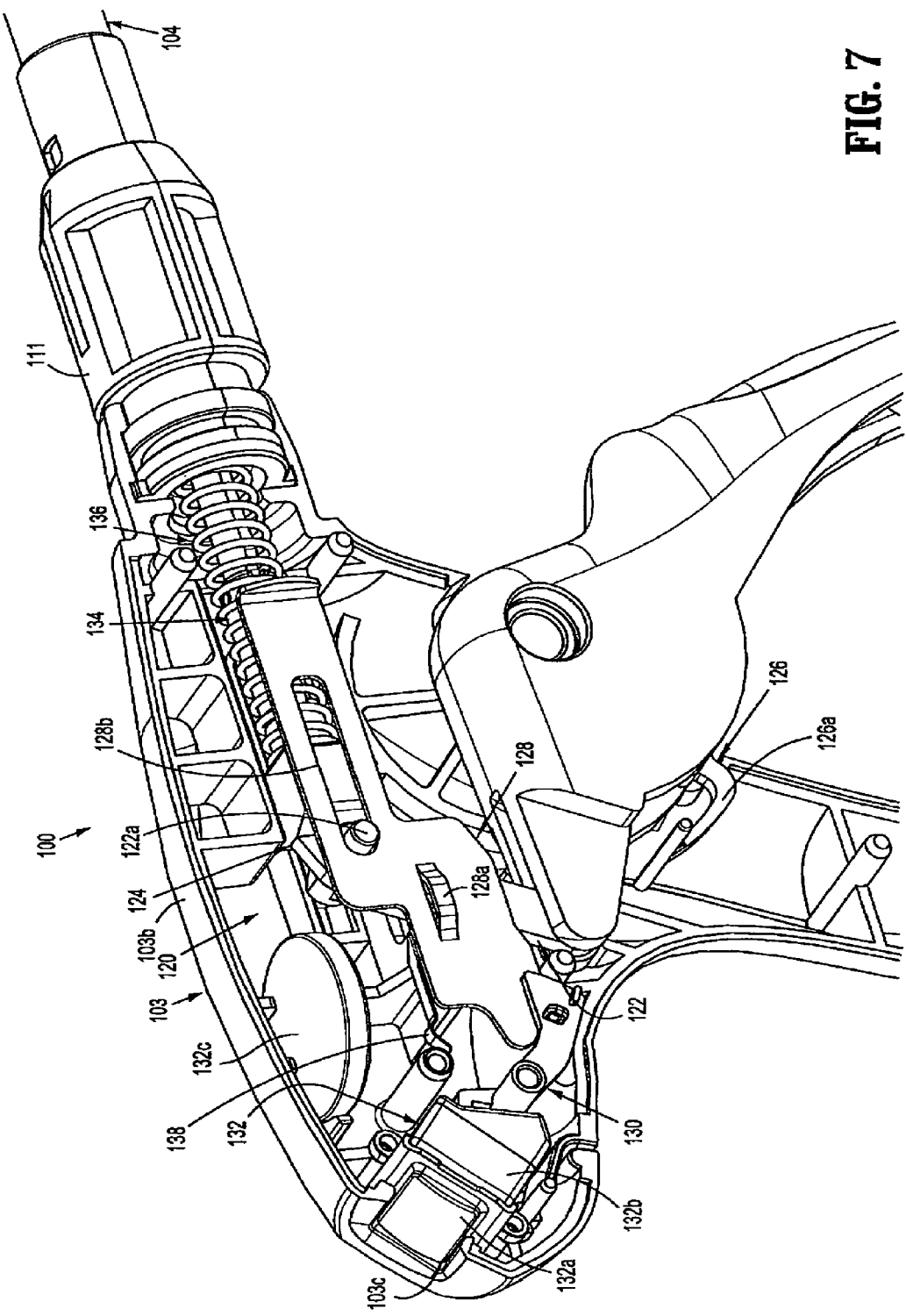
FIG. 7 is a right-side, perspective view of a handle assembly of the surgical clip applier of FIGS. 1-4, with a half of the body removed therefrom.
Figure 8:
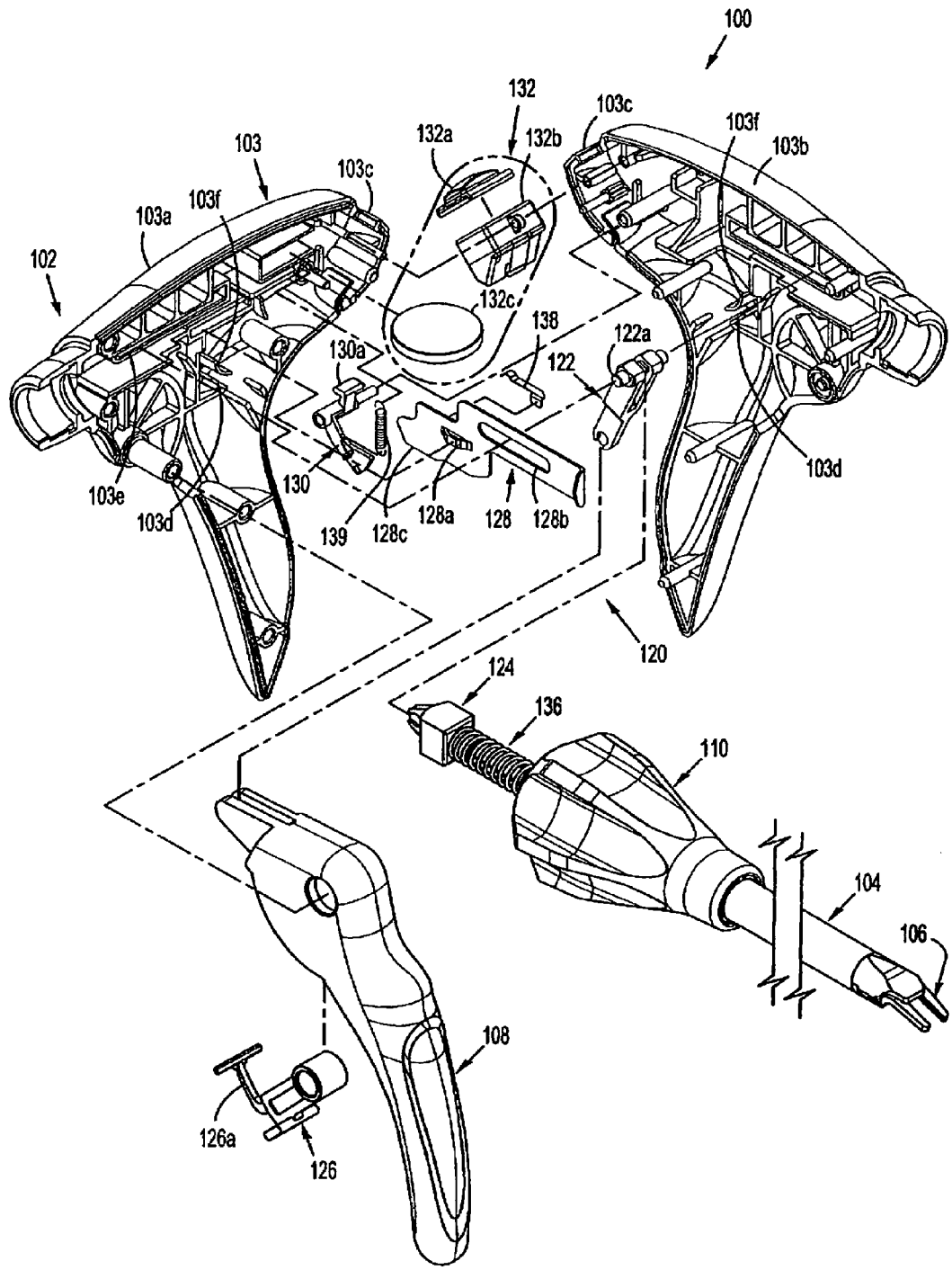
FIG. 8 is an exploded, perspective view of the handle assembly of the surgical clip applier of FIGS. 1-4, and a perspective view of a shaft assembly of the surgical clip applier of FIGS. 1-4 shown operatively associated therewith.

Referring now to FIGS. 6-8, handle assembly 102 of surgical clip applier 100 is shown. Handle assembly 102 includes a housing 103 having a first or right side half-section 103a and a second or left side half-section 103b. Handle assembly 102 includes a trigger 108 pivotably supported between right side half-section 103a and left side half-section 103b. Handle assembly 102 defines a window 103c formed in housing 103 for supporting and displaying a counter mechanism 132a, as will be discussed in greater detail below. Housing 103 of handle assembly 102 may be formed of a suitable plastic material.

Housing 103 supports a drive assembly 120 between right side half-section 103a and left side half-section 103b. Drive assembly 120 includes a wishbone link 122 having a first end pivotally connected to trigger 108, and a second end pivotally connected to a yoke 124. As seen in FIGS. 6-9, drive assembly 120 further includes a plunger 134 rotatably connected to yoke 124, and a spring 136 supported on plunger 134. Plunger 134 defines a longitudinal slot 134a (see FIG. 9) configured and adapted to receive a proximal end of a drive bar 140 therein.

Drive bar 140 is pinned to plunger 134 via a shear pin 142, the structure and function of which will be described in greater detail below. A cap 144 is provided through which drive bar 140 extends. A knob insert 111 is provided and is configured and adapted for rotational support in a distal end of housing 103 and for support of cap 144 therewithin. Knob insert 111 is keyed to knob 110 such that rotation of knob 110 results in concomitant rotation of knob insert 111. A seal 146 is provided to create an air-tight seal between drive bar 140 and an outer tube 150.

As seen in FIGS. 6-8, 48, 62, 67, 81, 83, 84, 92, 93 and 95, handle assembly 102 further includes an audible/tactile feedback member 126 operatively associated with trigger 108 so as to rotate together with and about a common axis as trigger 108. Feedback member 126 includes a deflectable arm 126a. In operation, as trigger 108 is actuated, arm 126a of feedback member 126 rides over and/or along a rib 103d formed in at least one of right side half-section 103a and left side half-section 103b. As will be discussed in greater detail below, as arm 126a reaches the end of rib 103d, arm 126a snaps over the end of rib 103d and creates and audible sound/click and/or a tactile vibration as arm 126a comes into contact with a surface 103f of right side half-section 103a and left side half-section 103b.

As seen in FIGS. 6-8, housing 103 further supports an actuator plate 128 on right side half-section 103a. Actuator plate 128 includes a protrusion 128a configured and adapted for slidable engagement in a slot 103e defined in right side half-section 103a of housing 103. Actuator plate 128 defines a longitudinally oriented slot 128b therein for slidably receiving a boss 122a of wishbone link 122. Actuator plate 128 further defines a counter actuation surface 128c for slidably engaging an arm 130b of a counter actuation lever 130. Counter actuation lever 130 is pivotally supported within housing 103.

As seen in FIGS. 6-8, 48, 62, 67, 81, 82, and 95, counter actuation lever 130 includes a first arm 130a configured and adapted to operatively, selectively engage a counter mechanism 132 supported in housing 103 and visible through window 103c defined in housing 103. Counter actuation lever 130 further includes a second arm 130b configured and adapted to operatively, slidably engage actuation surface 128c of actuation plate 128. A biasing member, in the form of a spring 139, is provided to bias second arm 130b of counter actuation lever 130 against counter actuation surface 128c of actuator plate 128.

In operation, as will be described in greater detail below, as trigger 108 is squeezed, trigger 108 causes wishbone link 122 to be advanced distally, causing yoke 124 to be advanced distally. When boss 122a of wishbone link 122 reaches the end of slot 128b of actuator plate 128, boss 122a forces actuator plate 128 in a distal direction thereby actuating counter actuation lever 130 to activate counter mechanism 132. In particular, when actuator plate 128 is moved distally a sufficient distance, second arm 130b of counter actuation lever 130 clears counter actuation surface 128c of actuator plate 128 and is urged in a first or clockwise direction by spring 139 resulting in first arm 130a of counter actuation lever 130 engaging counter mechanism 132. When actuator plate 128 is moved proximally a sufficient distance, second arm 130b of counter actuation lever 130 is cammed by counter actuation surface 128c of actuator plate 128 and is urged in a second or counter-clockwise direction thereby resulting in first arm 130a of counter actuation lever 130 disengaging counter mechanism 132.

Counter mechanism 132 includes a display 132a, a processor 132b, and an energy source 132c in the form of a battery or the like.

Display 132a may be any device known in the art to provide an indication of an event. The event may be related to the procedure or the operation of the clip applier 100. Display 132a may be a liquid crystal display (LCD), a plasma display, one or more light emitting diodes (LEDs), a luminescent display, a multi-color display, a digital display, an analog display, a passive display, an active display, a so called "twisted nematic" display, a so called "super twisted nematic" display, a "dual scan" display, a reflective display, a backlit display, an alpha numeric display, a monochrome display, a so called "Low Temperature Polysilicon Thin Film Transistor" (LPTS TFT) display, or any other suitable display 132a that indicates a parameter, information or graphics related to the procedure or clip applier 100.

In one embodiment, display 132a is a liquid crystal display which may be a black & white or color display that displays one or more operating parameters of clip applier 100 to the surgeon. In one embodiment, the operating parameter displayed may be an amount or number of remaining clips, a number of clips that have been used, a position parameter, a surgical time of usage, or any other parameter of the procedure. The display 132a may display text, graphics or a combination thereof.

In one embodiment, counter mechanism 132 may have a tab, preferably made from a Mylar or another polymeric insulating material, disposed between battery or energy source 132c and a contact of processor 132b which prevents the battery or energy source 132c from becoming drained during storage. The tab may extend out of housing 103 of surgical clip applier 100 in order to allow for easy removal of the tab therefrom. Once the tab is removed, battery or energy source 132c comes into electrical contact with the contact of processor 132b and in turn energizes display 132a.

Display 132c may include a lens or the like for magnifying the parameters displayed thereon. The lens of display 132a may magnify the display to any desired size in order to allow a surgeon to read the display with ease from a distance.

In an embodiment, counter mechanism may be a digital counter including a light source and an optical sensor for cooperating with the light source. The optical sensor may include an electronic eye or fiber optic lead producing a constant infrared beam that is shown on a detector such that the infrared beam or an interruption of the infrared beam can be translated into an electrical signal.

Turning now to FIGS. 9-46, shaft assembly 104 of surgical clip applier 100 is shown and described hereinbelow. Shaft assembly 104 and the components thereof may be formed of suitable biocompatible materials, such as, for example, stainless steel, titanium, plastics and the like. Shaft assembly 104 includes an outer tube 150 having a proximal end 150a supported within knob insert 111, a distal end 150b, and a lumen 150c extending therethrough. Shaft assembly 104 further includes an upper housing 152a and a lower housing 152b, each disposed within lumen 150c of outer tube 150. Outer tube 150 is secured within knob insert 111 by protrusions 111c extending from inner surface of knob insert 111a, 111b and engaging holes 150d formed in outer tube 150 (see FIG. 9). A trip block 154 is disposed within outer tube 150 and proximal of upper housing 152a. As seen in FIGS. 43 and 45, trip block 154 includes a window 154a formed in an upper surface thereof.

Shaft assembly 104 further includes a pusher bar 156 slidably interposed between outer tube 150, and upper housing 152a and trip block 154. Pusher bar 156 includes a distal end 156a defining a pusher 156c configured and adapted to selectively enter into a window 153a formed in upper housing 152a (see FIGS. 21 and 22) and engage/move (i.e., distally advance) clips stored in surgical clip applier 100. Pusher bar 156 further includes a proximal end 156b operatively secured to trip block 154 (see FIGS. 21 and 23). Pusher bar 156 defines a distal window 156d and a proximal window 156e.

As seen in FIG. 23, pusher bar 156 is biased to a proximal position, relative to trip block 154, by a biasing element 158, such as for example a compression spring, interposed between a boss 154a extending from trip block 154 and a surface of pusher bar 156. In an embodiment, as seen in FIG. 23, spring 158 is supported on a tine 156f formed in a window 156g of pusher bar 156, wherein a distal end of tine 156f slidably extends through boss 154a of trip block 154. Spring 158 is disposed between a base of tine 156f and stem 154a of trip block 154.

As best seen in FIGS. 9, 12, 43 and 44, shaft assembly 104 further includes a latch lock-out 160 operatively supported within a channel 154b (see FIG. 44) defined in an underside of trip block 154. Latch lock-out 160 includes a latch member 162 pivotally supported in channel 154b of trip block 154, and a biasing member 164 securely connected within channel 154b of trip block 154 and operatively connected to latch member 162 so as to bias latch member 162, in a counter-clockwise direction as shown, to a first condition. Latch member 162 includes a distal portion 162a defining a shoulder and a proximal portion 162b defining a rounded surface 162b. Biasing member 164 includes an arm 164a in contact with and acting on distal portion 162a of latch member 162 to force distal portion 162a of latch member 162 radially inward (i.e., towards or in a counter-clockwise direction as shown) and likewise to force proximal portion 162b of latch member 162 radially outward (i.e., away or in a counter-clockwise direction as shown).

As best seen in FIGS. 9, 14, 43 and 46, shaft assembly 104 further includes a pusher-bar latch mechanism 166 operatively supported within a channel 153b (see FIG. 46) defined in an underside of upper housing 152a. Pusher-bar latch mechanism 166 includes a lock-out bar 168 pivotally supported in channel 153b of upper housing 152a, and a biasing member 170 securely connected within channel 153b of upper housing 152b and operatively connected to lock-out bar 168 so as to bias lock-out bar 168, in a clockwise direction as shown, to a first condition. Lock-out bar 168 includes a distal portion 168a operatively connected to biasing member 170, and a proximal portion 168b defining a catch. Biasing member 170 includes a proximal portion 170b in contact with and acting on distal portion 168a of lock-out bar 168 to force distal portion 168a of lock-out bar 168 radially outward (i.e., away from lower housing 152b or in a clockwise direction as shown) and likewise to force proximal portion 168b of lock-out bar 168 radially inward (i.e., toward lower housing 152b or in a clockwise direction as shown).

As seen in FIGS. 27 and 46, a distal portion 170a of biasing member 170 is received in an aperture formed in a retention plate 172. Retention plate 172 is operatively supported in channel 153b of upper housing 152a and includes a pair of spaced apart, resilient, distal tangs 172a. Tangs 172a of retention plate 172 are configured and adapted to selectively engage a backspan of a distal-most surgical clip "C1" (not shown in FIG. 46) of a stack of surgical clips "C" retained within surgical clip applier 100.

As seen in FIGS. 9, 24, 25 and 27, a stack of surgical clips "C" is loaded and/or retained within channel 153b of upper housing 152a in a manner so as to slide therewithin and/or therealong. As mentioned above, a distal-most surgical clip "C1" of the stack of surgical clips "C" is selectively held in position by tangs 172a of retention plate 172.

Shaft assembly 104 further includes a clip follower 180 slidably supported and/or retained within channel 153b of upper housing 152a. Clip follower 180 includes a head portion 180a disposed behind and in contact with a proximal-most surgical clip "C2" of the stack of surgical clips "C". Clip follower 180 further includes a tail portion 180b extending in a proximal direction from head portion 180a. Head portion 180a defines a ramp 180c near a proximal end thereof. In operation, as will be discussed in greater detail below, as clip follower 180 is distally advanced, head portion 180a thereof will contact and engage lock-out bar 168 of pusher-bar latch mechanism 166 such that distal portion 168b of lock-out bar 168 is cammed or urged in a radially outward direction (i.e., toward upper housing 152a or in a counter-clockwise direction as shown) by ramp 180c of head portion 180a of clip follower 180.

A biasing member in the form of a compression spring 182 is disposed about tail portion 180b of clip follower 180. Biasing member 182 functions to bias clip follower 180 in a distal direction, thereby applying a distally oriented force on the stack of clips "C". Retainer block 184 includes a flange 184b interposed between upper housing 152a and trip block 154.

As seen in FIGS. 9 and 24-26, shaft assembly 104 further includes a clip retainer plate 186 configured and adapted to under/overlie the stack of surgical clips "C", clip follower 180 and at least a portion of retainer block 184. As best seen in FIG. 27, clip retainer plate 186 includes a ramp 186a formed near a distal end thereof. As will be described in greater detail below, ramp 186a of clip retainer plate 186 functions to engage a backspan of distal-most clip "C1" as distal-most clip "C1" is being advanced by pusher bar 156. Clip retainer plate 186 snap-fit and/or press-fit engages into channel 153b of upper housing 152a utilizing tabs 186b engaged with elements 153j (see FIG. 9).

As seen in FIGS. 9, 27, 31-35, 39, 41 and 42, shaft assembly 104 further includes a wedge plate 188 under/overlying clip retainer plate 186. Wedge plate 188 includes a substantially tapered distal end 188a for selective operative interposition between jaws 106. As seen in FIGS. 33 and 42, wedge plate 188 defines a fin or tab 188b projecting from a lower surface thereof.

As seen in FIGS. 9, 28-30, 34, 35, 39, 41 and 42, shaft assembly 104 further includes a drive channel 190 positioned adjacent wedge plate 188. Drive channel 190 includes a pair of side walls 190a depending from a backspan 190b thereof, in a direction away from wedge plate 188 and into a channel 153c defined by lower housing 152b. Drive channel 190 further includes a tab 190c extending from backspan 190b, in the direction of side walls 190a (see FIGS. 39 and 41), an elongate slot 190d formed in backspan 190b (see FIGS. 39 and 42), and a cut-out 190e formed in one of side walls 190a (see FIGS. 39 and 42).

As seen in FIGS. 9, 11, 24, 26, 28, 29, 31, 37 and 38, and as described above, shaft assembly 104 includes a drive bar 140 having a proximal end 140b extending into handle assembly 102, and distal end 140a extending below and/or adjacent to a proximal end of wedge plate 188. Drive bar 140 includes a goose-neck 140c (see FIG. 11) such that distal end 140a thereof is on/in a different plane than proximal end 140b thereof, and such that at least a portion of distal end 140a underlies or is adjacent to drive channel 190. Distal end 140a of drive bar 140 defines an elongate slot 140d formed therein. Distal end 140a of drive bar 140 further includes a stop 140h formed therein at a location proximal of slot 140d and extending in a direction away from lower housing 152b. Proximal end 140b of drive bar 140 includes formations and/or structure 140f (see FIG. 11) configured and adapted to support and/or otherwise retain trip mechanism 192 thereon.

Figure 11:
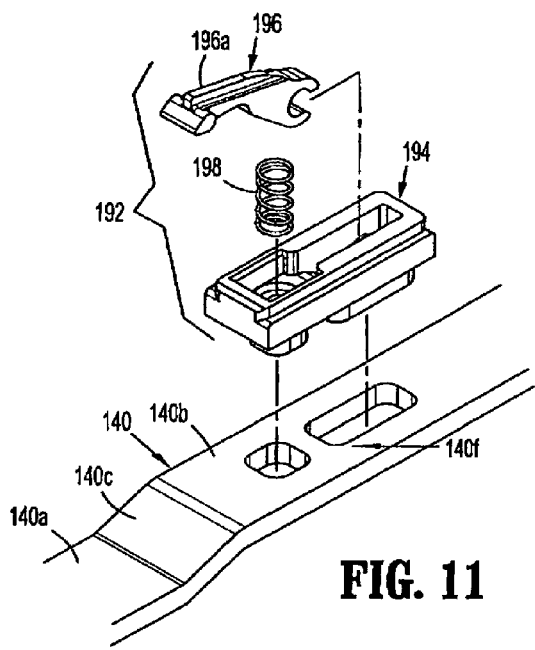
FIG. 11 is an exploded, perspective view of the indicated area of detail of FIG. 9, illustrating a trip mechanism of the shaft assembly.
Figure 12:
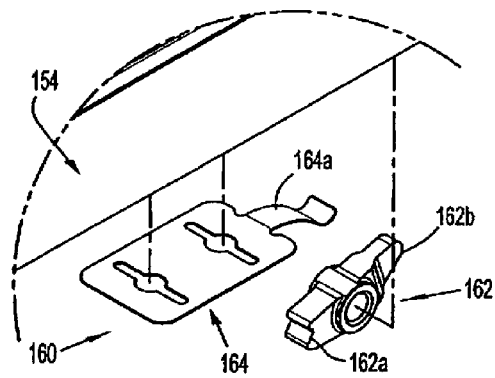
FIG. 12 is an exploded, perspective view of the indicated area of detail of FIG. 9, illustrating a latch lock-out of the shaft assembly.
Figure 14:
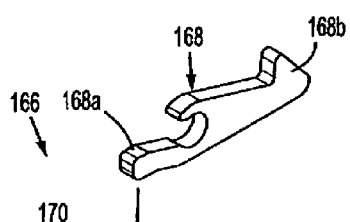
FIG. 14 is an exploded, perspective view of the indicated area of detail of FIG. 9, illustrating a pusher-bar latch mechanism of the shaft assembly.
Figure 13:
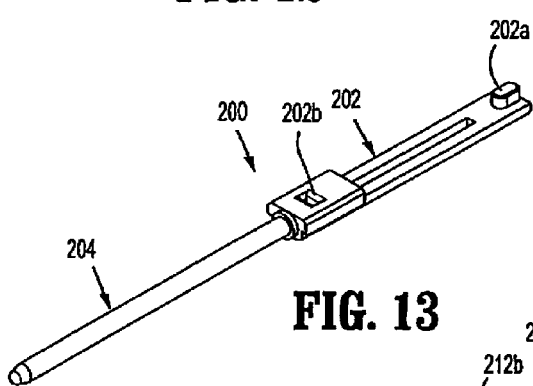
FIG. 13 is a perspective view of the indicated area of detail of FIG. 9, illustrating a joint slider the shaft assembly.
Figure 15:
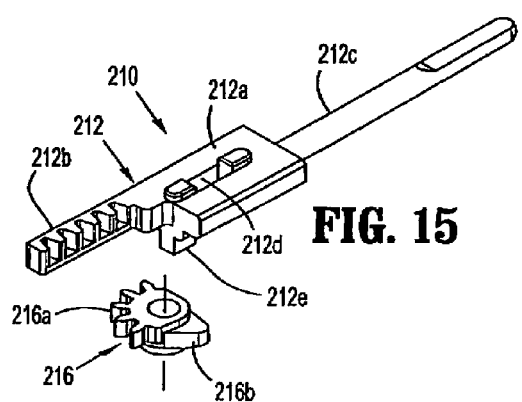
FIG. 15 is an exploded, perspective view of the indicated area of detail of FIG. 9, illustrating a wedge plate rack mechanism of the shaft assembly.

As seen in FIGS. 9, 11, 24, 26 and 43, shaft assembly 104 further includes a trip mechanism 192 supported in proximal end 140b of drive bar 140, in the manner described above. In particular, trip mechanism 192 includes a trip block 194 configured and adapted for retention in or support on formations and/or structure 140f of drive bar 140, and a trip lever 196 pivotally connected to trip block 194. Trip mechanism 192 further includes a biasing member 198, in the form of a compression spring, interposed between trip block 194 and a free end of trip lever 196, for biasing the free end of trip lever 196 in a direction (i.e., clockwise as shown) toward trip block 154. As seen in FIG. 11, trip lever 196 defines a catch 196a formed along an upper surface thereof.

As seen in FIGS. 9, 13, 34, 37 and 38, shaft assembly 104 further includes a slider joint 200 slidably interposed between channel 153c of lower housing 152b and distal end 140a of drive bar 140. Slider joint 200 includes a body portion 202 and a rod 204 extending therefrom. When properly interposed between channel 153c of lower housing 152b and distal end 140a of drive bar 140, rod 204 of slider joint 200 extends in a substantially distal direction. Rod 204 of slider joint 200 is slidably passed through a stub 153d formed in and extending from channel 153c of lower housing 152b (see FIG. 38). Shaft assembly 104 further includes a biasing member 206, in the form of a compression spring, supported on rod 204 and interposed between stub 153d of lower housing 152b and body portion 202 of slider joint 200.

Body portion 202 of slider joint 200 includes a tab 202a formed near a proximal end thereof, and configured and adapted for slidably engagement in elongate slot 140d of drive bar 140 (see FIGS. 37 and 38). Body portion 202 of slider joint 200 further includes a pocket 202b formed near a distal end thereof, and configured and adapted for receiving tab 190c of drive channel 190 therein (see FIG. 29).

As seen in FIGS. 9, 15, 34, 35 and 37, shaft assembly 104 further includes a wedge plate rack mechanism 210 operatively interposed between channel 153c of lower housing 152b and drive channel 190. Wedge plate rack mechanism 210 includes a wedge plate rack 212 slidably disposed within channel 153c of lower housing 152b. Wedge plate rack 212 includes a body portion 212a, a rack 212b extending distally from body portion 212a, a tail or rod 212c extending proximally from body portion 212a, a pocket 212d formed in an upper surface of body portion 212a, and a stem 212e extending from a bottom surface of body portion 212a.

Stem 212e of wedge plate rack 212 rides within a groove (not shown) formed in a surface of channel 153c of lower housing 152b. Tail or rod 212d of wedge plate rack 212 is slidably passed through a stub 153e formed in and extending from channel 153c of lower housing 152b (see FIGS. 9 and 37). Wedge plate rack mechanism 210 further includes a biasing member 214, in the form of a compression spring, supported on rod 212d and interposed between stub 153e of lower housing 152b and body portion 212a of wedge plate rack 212. As seen in FIG. 33, fin or tab 188b of wedge plate 188 is disposed within pocket 212d formed in an upper surface of body portion 212a of wedge plate rack 212.

Wedge plate rack mechanism 210 further includes a gear 216 pivotally connected to lower housing 152b. Gear 216 includes a set of teeth 216a that are in operative engagement with rack 212b of wedge plate rack 212, and an opposed tooth 216b operatively engageable with cut-out 190e formed in one of side walls 190a of drive channel 190 (see FIG. 35). In operation, as will be discussed in greater detail below, as drive channel 190 is axially displaced in a distal direction, drive channel 190 causes gear 216 to rotate (i.e., in a clockwise direction as shown) and thus causes wedge plate rack 212 to axially move in a proximal direction, or vice-versa.

As seen in FIGS. 9, 34, 36 and 40, shaft assembly 104 further includes a pawl and rack assembly 220 operatively interposed between channel 153c of lower housing 152b and proximal end 140b of drive bar 140. Pawl and rack assembly 220 includes a rack 222 secured to an underside of drive bar 140 (i.e., interposed between proximal end 140b of drive bar 140 and channel 153c of lower housing 152b) such that rack 222 is movable together with drive bar 140. Rack 222 includes a plurality of teeth 222a interposed between a distal recess 222b and a proximal recess 222c (see FIG. 36). Recesses 222b and 222c are provided to allow a pawl to reverse and advance back over teeth 222a of rack 222 when rack 222 changes between proximal and distal movement.

Pawl and rack assembly 220 includes a pawl 224 pivotally connected to lower housing 152b by a pawl pin 226 at a location wherein pawl 224 is in substantial operative engagement with rack 222. Pawl 224 includes a pawl tooth 224a which is selectively engageable with teeth 222a of rack 222. Pawl tooth 224a is engageable with rack teeth 222b to restrict longitudinal movement of rack 222 and, in turn, drive bar 140 within shaft assembly 104 and trigger 108 of handle assembly 102.

Pawl and rack assembly 220 further includes a pawl spring 228 configured and positioned to bias pawl 224 into operative engagement with rack 222.

As seen throughout the figures and particularly FIGS. 34 and 35, shaft assembly 104 further includes a set of jaws 106 operatively supported in a distal end thereof. Jaws 106 include a proximal section 106b disposed within a distal end of drive channel 190 and a pair of jaw members 106c extending from the distal end of upper and lower housing 152a, 152b. Each jaw member 106c defines a camming surface 106d against which a distal edge of drive channel 190 will engage, when drive channel 190 is distally advanced, to urge jaw members 106c toward one another. The set of jaws 106 may be configured so as to flex or splay outward in order to receive and/or accommodate a clip "C" that is wider than an at rest inner width distance of jaw members 106c. In this manner, the set of jaws 106 have the ability to pass through a 5 mm, 10 mm or fixed size cannula or trocar and be able to accommodate a relatively wider clip "C" so as to engage a relatively wider vessel "V".

Figure 9:
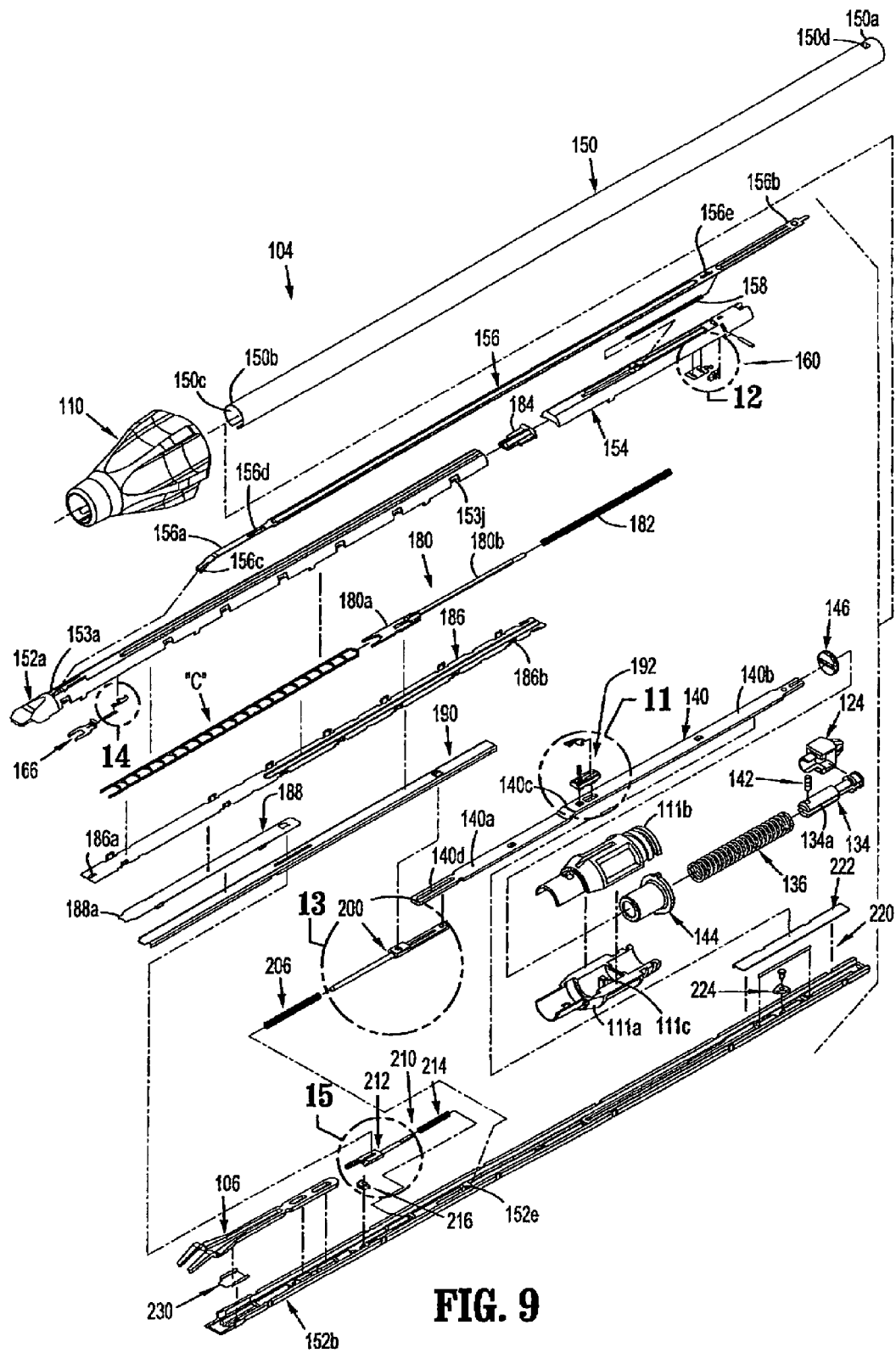
FIG. 9 is an exploded, perspective view of the shaft assembly of the surgical clip applier of FIGS. 1-4.
Figure 10:
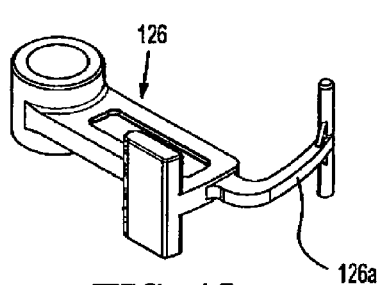
FIG. 10 is a perspective view of a tactile feedback member of the surgical clip applier of FIGS. 1-4.

As best seen from FIGS. 9, 27 and 88, each clip "C" has a pre-formed or un-formed outer width and jaws 106 have a manufactured outer width, wherein the outer width of jaws 106 relative to the outer width of clip "C" results in a ratio approximately less than or equal to 1 to 1.8 (e.g., 1:1.8). The ratio may be established or determined when clip "C" is present within jaws 106 or when clip "C" is not present within jaws 106.

As seen in FIGS. 9, 34 and 35, shaft assembly 104 further includes a substantially U-shaped channel 230 disposed within lower housing 152b and operatively connected to a distal end of drive channel 190. U-shaped channel 230 functions to retain jaw members 106c in a substantially aligned orientation with one another during an operation of surgical clip applier 100.

Figure 17:
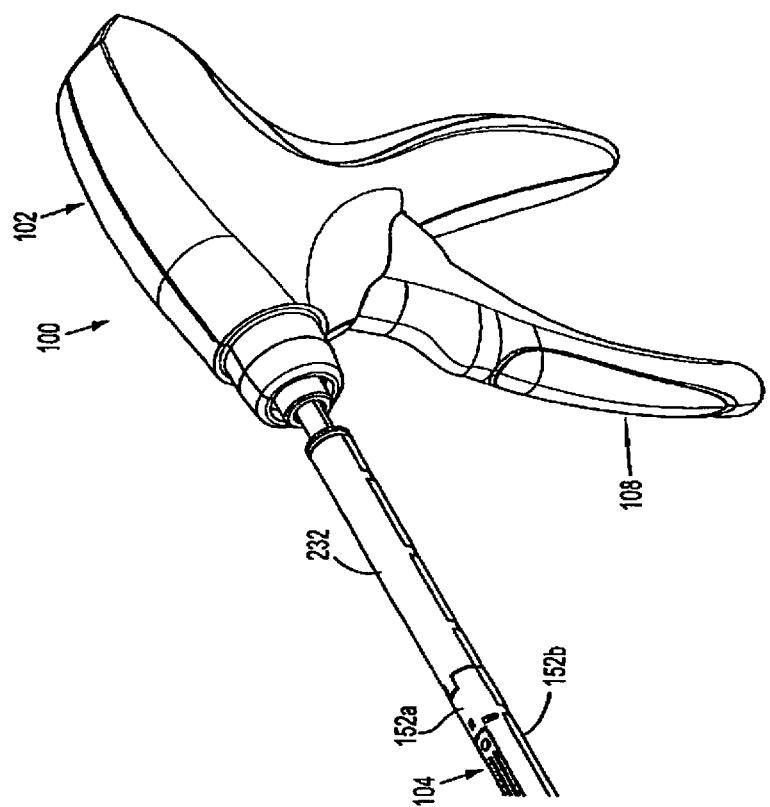
FIG. 17 is an assembled, perspective view of a proximal end of the surgical clip applier of FIG. 16, illustrating a joint extension disposed between the shaft assembly and the handle assembly.
Figure 16:
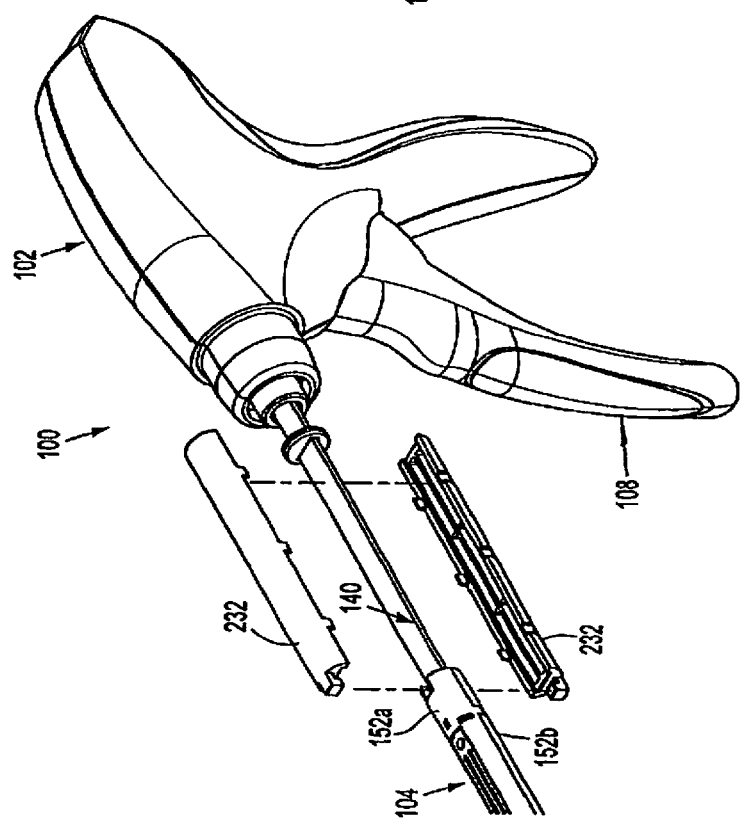
FIG. 16 is a partially exploded, perspective view of a proximal end of the surgical clip applier of FIGS. 1-4, illustrating a joint extension disposed between the shaft assembly and the handle assembly.
Figures 47, 48:
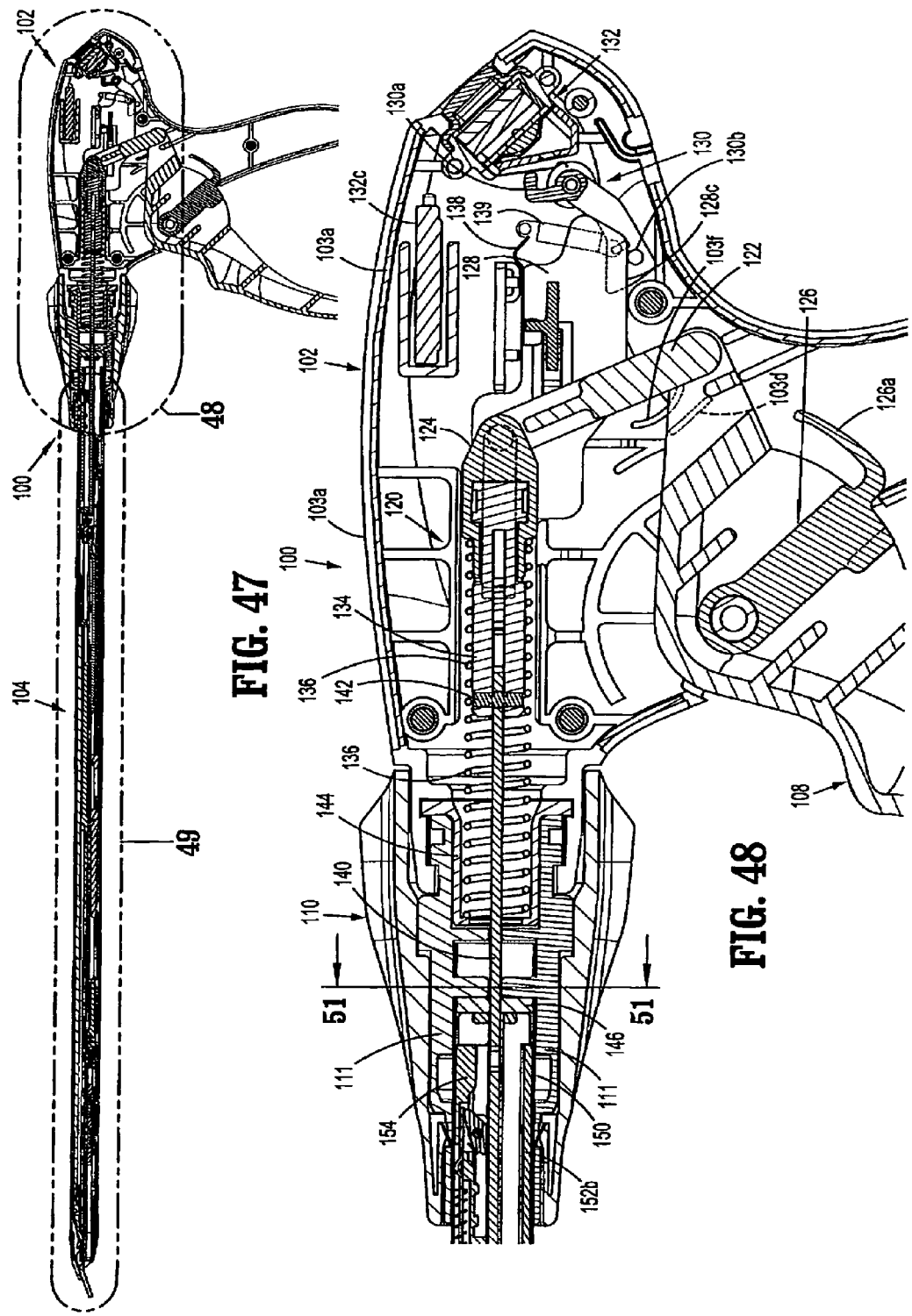
FIG. 47 is a longitudinal, elevational, cross-sectional view of the surgical clip applier of FIGS. 1-4.
FIG. 48 is an enlarged, elevational, cross-sectional view of the indicated area of detail of FIG. 47.
Figure 51:
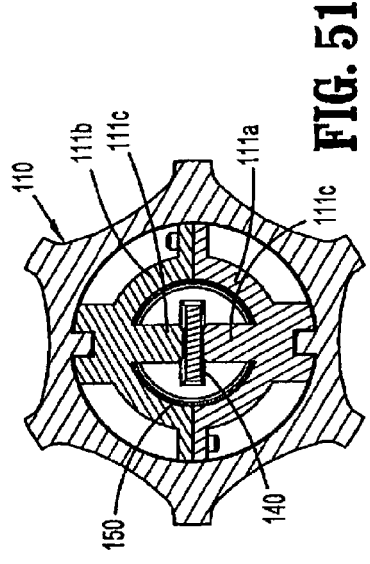
FIG. 51 is a transverse, cross-sectional view as taken through 51-51 of FIG. 48.
Figure 49:
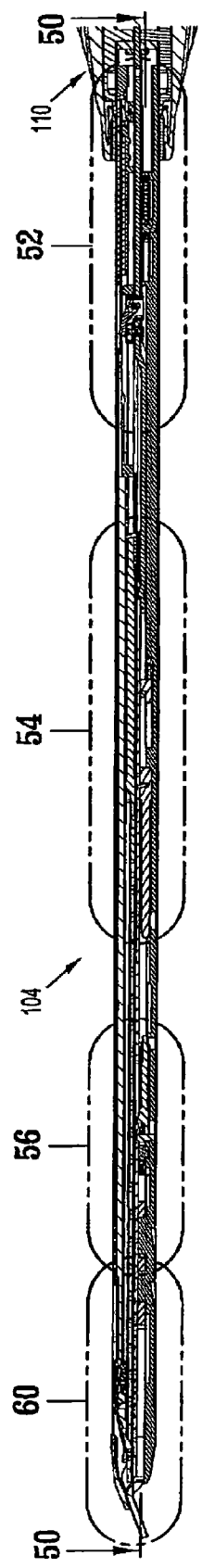
FIG. 49 is an enlarged, elevational, cross-sectional view of the indicated area of detail of FIG. 47.
Figure 50:
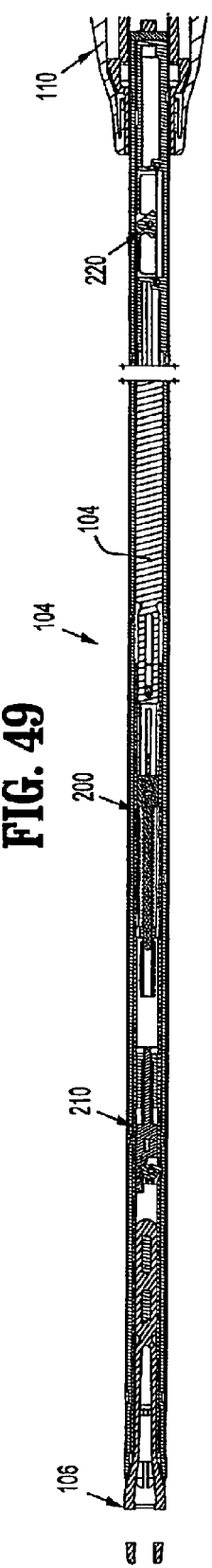
FIG. 50 is a longitudinal, cross-sectional view as taken through 50-50 of FIG. 49.

As seen in FIGS. 16 and 17, surgical clip applier 100 may include an extension joint housing 232 operatively interposed between upper and lower housings 152a, 152b of shaft assembly 104 and handle assembly 102. In this manner, surgical clip applier 100 may be modified to use in surgical procedures requiring a greater depth of insertion of jaws 106, such as, for example, in bariatric surgery.

It is contemplated for surgical clip applier 100 to operate with stacks of clips "C" of varying sizes. For example, the clips comprising the stack of clips "C" may have a relatively narrow dimension or a relatively wide dimension.

The operation of surgical clip applier 100, to crimp a surgical clip around a target tissue, such as, for example, a vessel, will now be described. With reference to FIGS. 47-61, trigger 108 is generally in an uncompressed or unactuated state. As such, yoke 124 of drive assembly 120 is in a retracted position and thus, plunger 134 and drive bar 140 are also in a retracted position.

As seen in FIG. 52, catch 196a of trip lever 196 of trip mechanism 192 is positioned within window 156e of pusher bar 156, and latch member 162 of latch lock-out 160 is maintained biased by a proximal end of pusher bar 156. Pusher bar 156 is biased to a proximal-most position by biasing member 158. Also, as seen in FIG. 53, tooth 224a of pawl 226 of pawl and rack assembly 220 is disposed within distal recess 222b of rack 222.

Figure 58:
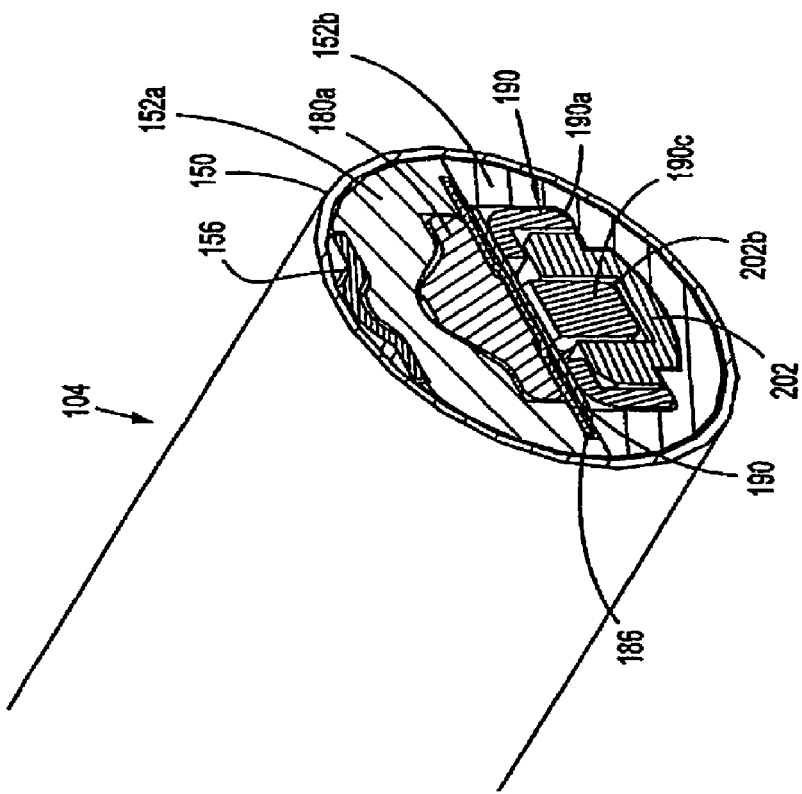
FIG. 58 is a transverse, cross-sectional view as taken through 58-58 of FIG. 54.

As seen in FIGS. 54, 55 and 58, tab 202a of body portion 202 of slider joint 200 is located at a distal-most end of elongate slot 140d of drive bar 140. The length of elongate slot 140d of drive bar 140 defines a dwell "d" of surgical clip applier 100.

Figure 59:
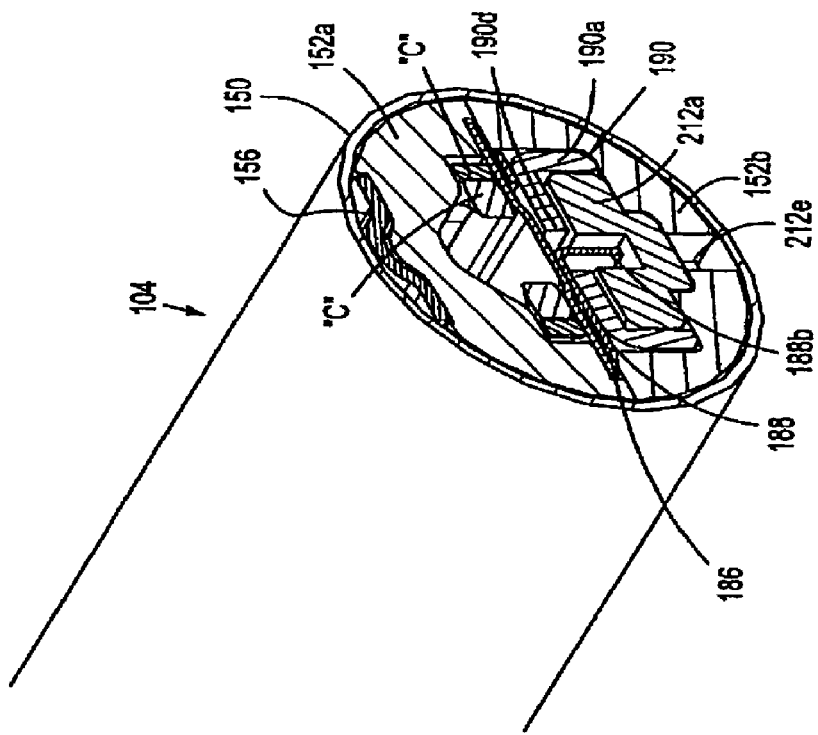
FIG. 59 is a transverse, cross-sectional view as taken through 59-59 of FIG. 56.

As seen in FIGS. 56, 57 and 59, wedge plate 188 is at a distal-most position, wedge plate rack 212 of wedge plate rack mechanism 210 is at a distal-most position, and tooth 216b of gear 216 of wedge plate rack mechanism 210 is disposed within cut-out 190e formed in one of side walls 190a of drive channel 190.

Figure 60:
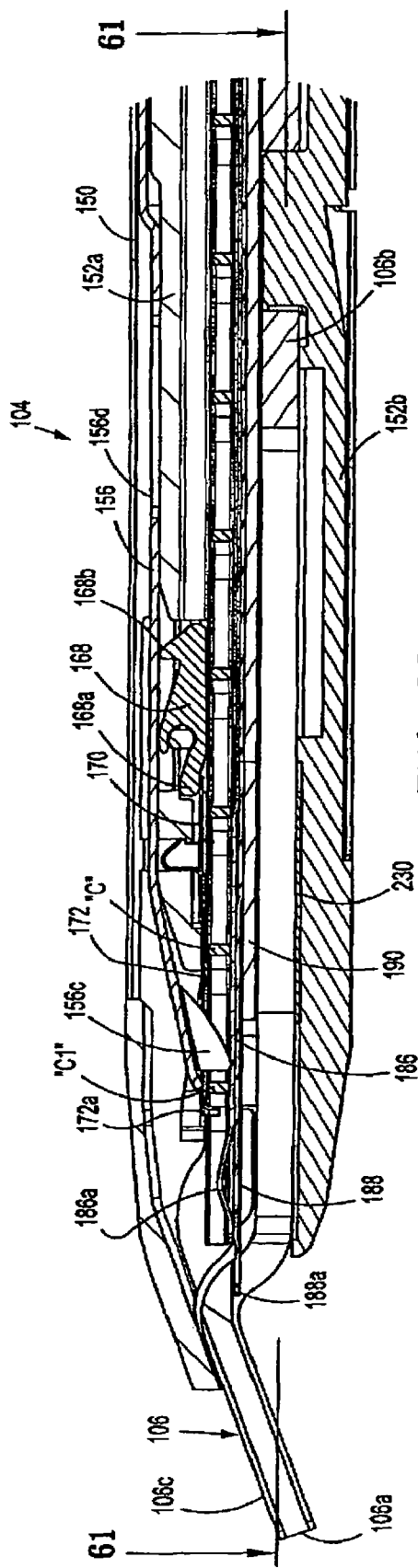
FIG. 60 is an enlarged, elevational, cross-sectional view of the indicated area of detail of FIG. 49.
Figure 61:
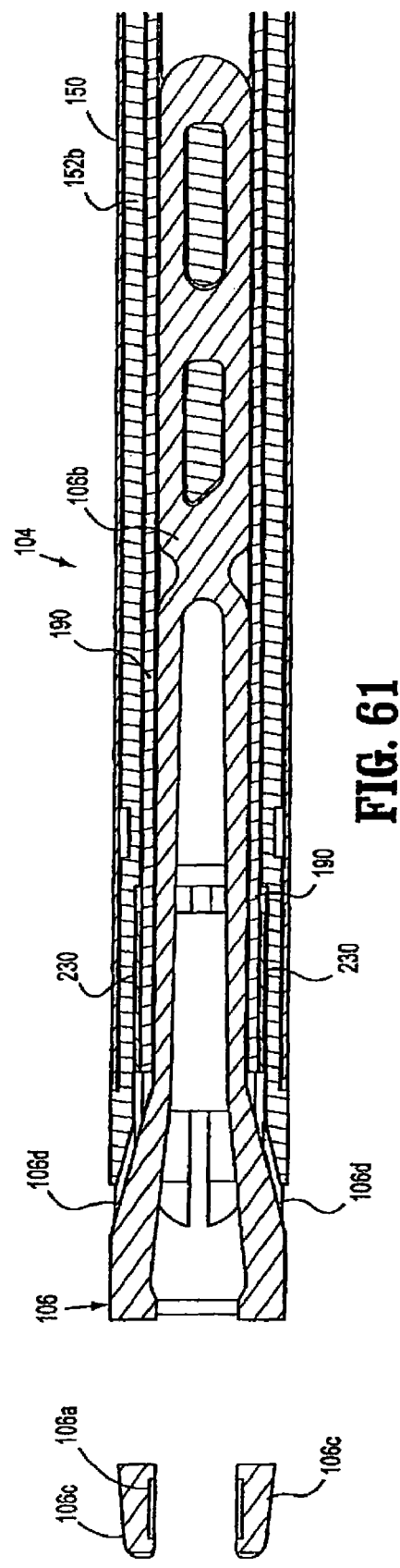
FIG. 61 is a longitudinal, cross-sectional view taken through 61-61 of FIG. 60.
Figure 62:
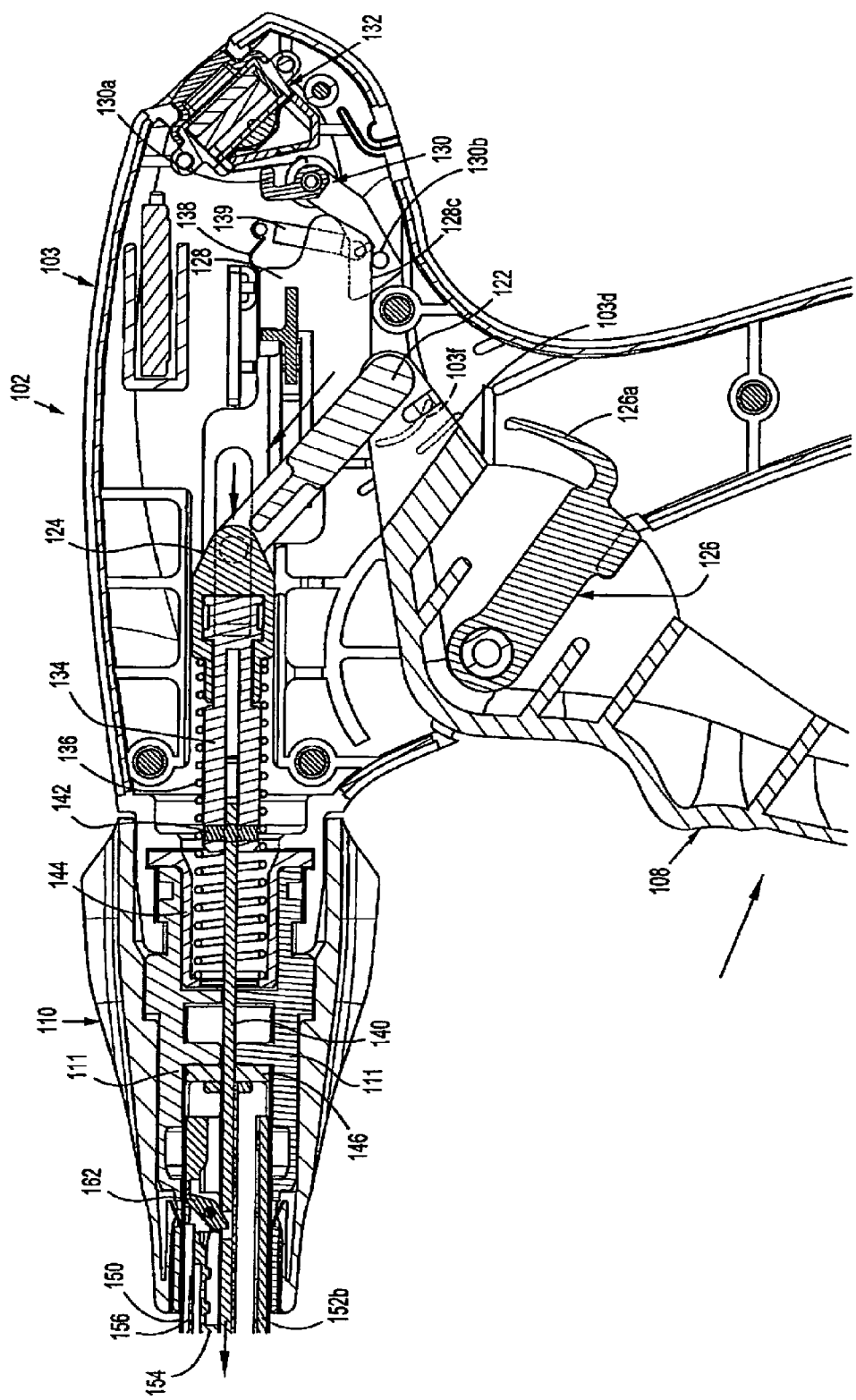
FIG. 62 is a longitudinal, elevational, cross-sectional view of the surgical clip applier of FIGS. 1-4, illustrating a first stage of an initial stroke of the trigger of the handle assembly.

As seen in FIGS. 60 and 61, distal end 188a of wedge plate 188 is interposed between jaw members 106c of jaws 106. Also, a distal-most clip "C1" of the stack of clips "C" is held in position by tangs 172a of retention plate 172. As seen in FIG. 60, proximal portion 168b of lock-out bar 168 of pusher-bar latch mechanism 166 is disposed beneath pusher bar 156 and is biased as such by biasing member 170.

Turning now to FIGS. 62-66, as trigger 108 is squeezed or actuated from the initial position, during a first stage of an initial stroke, as described above, trigger 108 causes wishbone link 122 to move yoke 124 in a distal direction which, in turn, causes plunger 134 to move distally and to move drive bar 140 distally, via shear pin 142. As seen in FIG. 63, as drive bar 140 is moved distally, since catch 196a of trip lever 196 of trip mechanism 192 is positioned within window 156e of pusher bar 156, pusher bar 156 is also moved distally. Simultaneously therewith, rack 222 is moved distally causing teeth 222a thereof to move over tooth 224a of pawl 226 and out of distal recess 222b thereof.

As seen in FIG. 63, distal portion 162a of latch member 162 of latch lock-out 160 is pivoted into a window 140g formed in drive bar 140 due to the urging of arm 164a of biasing member 164.

As seen in FIGS. 65 and 66, as pusher bar 156 is distally advanced, pusher 156c thereof engages a backspan of a distal-most clip "C1" and advances said distal-most clip "C1" over ramp 186a of clip retainer plate 186 and into channels 106a of jaw member 106c of jaws 106.

Turning now to FIGS. 67-80, as trigger 108 is further squeezed or actuated from the first stage of the initial stroke through a second stage of the initial stroke, as described above, trigger 108 causes wishbone link 122 to further move yoke 124 in a distal direction which, in turn, causes plunger 134 to further move distally and to further move drive bar 140 distally, via shear pin 142.

Figure 67:
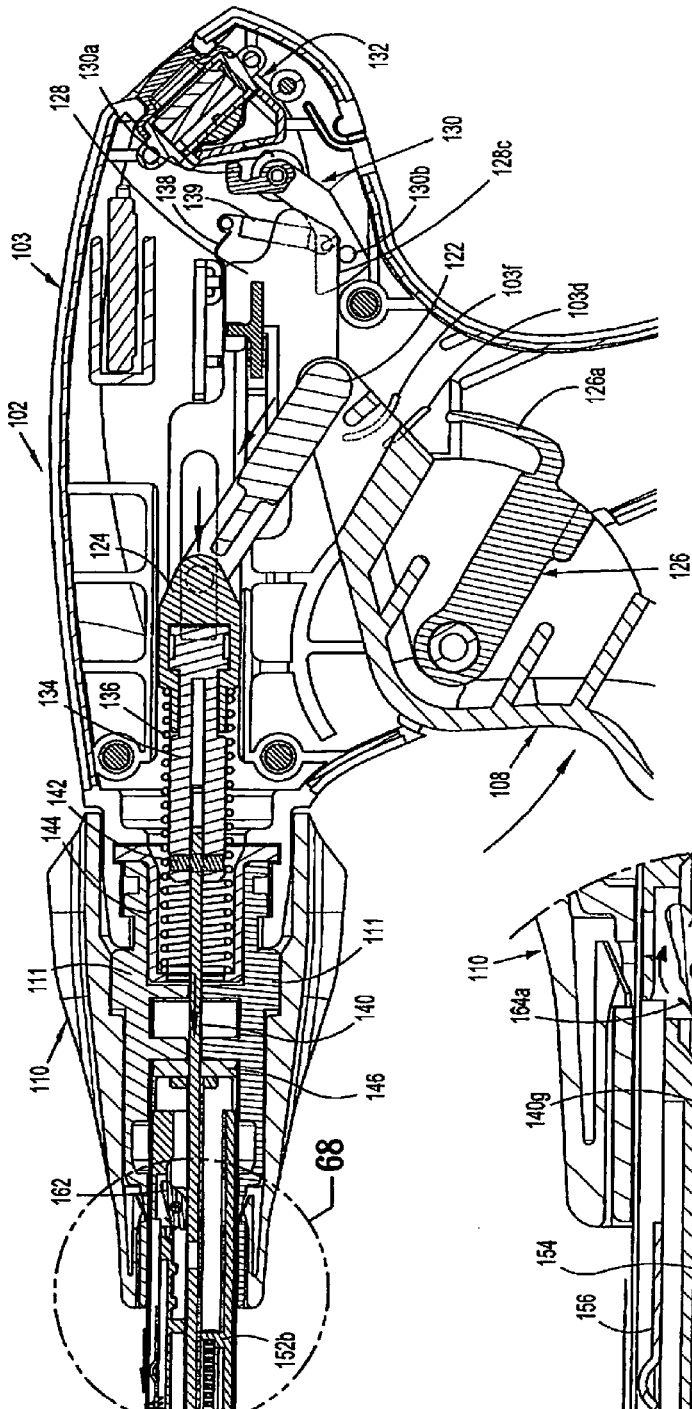
FIG. 67 is a longitudinal, elevational, cross-sectional view of the surgical clip applier of FIGS. 1-4, illustrating a second stage of an initial stroke of the trigger of the handle assembly.
Figure 68:
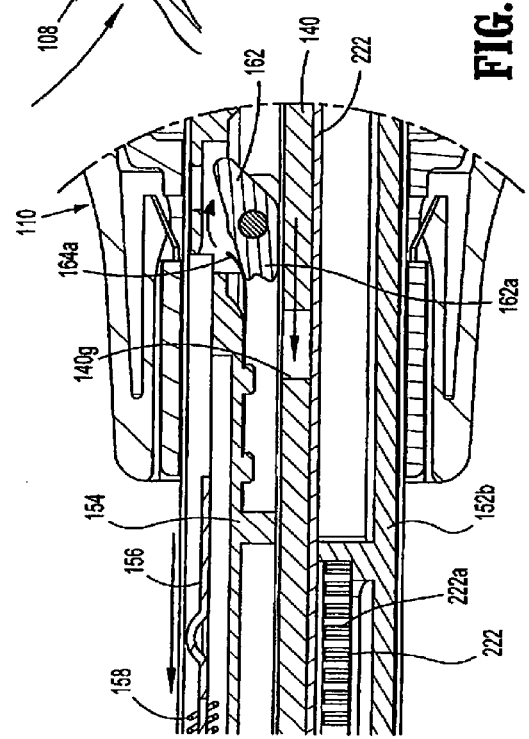
FIG. 68 is an enlarged, elevational, cross-sectional view of the indicated area of detail of FIG. 67, during the second stage of the initial stroke of the trigger of the handle assembly.

As seen in FIGS. 67 and 68, as drive bar 140 is further advanced distally, drive bar 140 cams against distal portion 162a of latch member 162 of latch lock-out 160 and thereby pivots distal portion 162a of latch member 162 out of window 140g formed in drive bar 140. As seen in FIGS. 69 and 70, with catch 196a of trip lever 196 of trip mechanism 192 still positioned within window 156e of pusher bar 156, pusher bar 156 is further moved distally. As seen in FIG. 69, as pusher bar 156 is further distally advanced, pusher 156c thereof further advances said distal-most clip "C1" into channels 106a of jaw member 106c of jaws 106.

As seen in FIG. 70, trip lever 196 of trip mechanism 192 is cammed down by camming surfaces 154b and 154c of trip block 154, against the bias of biasing member 198, such that catch 196a of trip lever 196 disengages window 156e of pusher bar 156.

As seen in FIGS. 69 and 71, as distal-most clip "C1" is advanced into jaw members 106c of jaws 106, the stack of clips "C" is distally advanced due to a distal force acting thereon by clip follower 180, which is being urged distally due to a biasing force exerted on head portion 180a of clip follower 180 by biasing member 182.

As seen in FIG. 72, as drive bar 140 is moved distally, tab 202a of body portion 202 of slider joint 200 is translated through elongate slot 140d of drive bar 140, thereby reducing the length and/or size of dwell "d". Drive bar 140 is advanced distally until, as seen in FIGS. 71 and 72, stop 140h of drive bar 140 abuts against a proximal-most end of drive channel 190, and until shoulders 140h abut against a proximal-most end of side walls 190a of drive channel 190.

As seen in FIGS. 73-75, once catch 196a of trip lever 196 is moved out of engagement with window 156e of pusher bar 156, pusher bar 156 is retracted in a proximal direction due to the biasing force exerted thereon by biasing member 158. Pusher bar 156 is retracted until pusher 156a thereof is positioned proximal of a backspan of a distal-most surgical clip of the stack of clips "C".

As seen in FIG. 76, as pusher bar 156 is biased to the retracted position, pusher bar 156 cams against latch member 162 of latch lock-out 160 and thereby pivots distal portion 162a of latch member 162 (e.g., clockwise as shown) out of window 140g formed in drive bar 140.

As seen in FIGS. 71, 72, 77 and 78, when stop 140h of drive bar 140 abuts against a proximal-most end of drive channel 190 and shoulders 140h abut against a proximal-most end of side walls 190a of drive channel 190, further distal advancement of drive bar 140 results in distal advancement of drive channel 190. As drive channel 190 is advanced distally, cut-out 190e formed in side wall 190a of drive channel 190 cams against tooth 216b of gear 216 of wedge plate rack mechanism 210 and urges gear 216 to rotate, i.e., clockwise as shown. Rotation of gear 216 results in proximal displacement of body portion 212a of wedge plate rack 212 of wedge plate rack mechanism 210 due to the inter-engagement of the set of teeth 216a of gear 216 with rack 212b of wedge plate rack 212.

Figure 79:
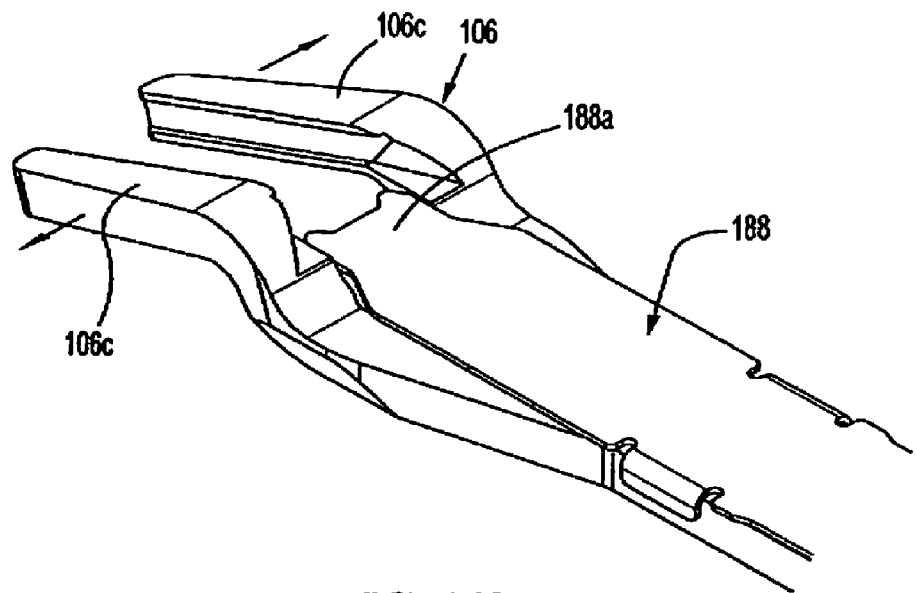
FIG. 79 is a front, perspective view of the jaws of the surgical clip applier having the wedge plate interposed therebetween.
Figure 80:
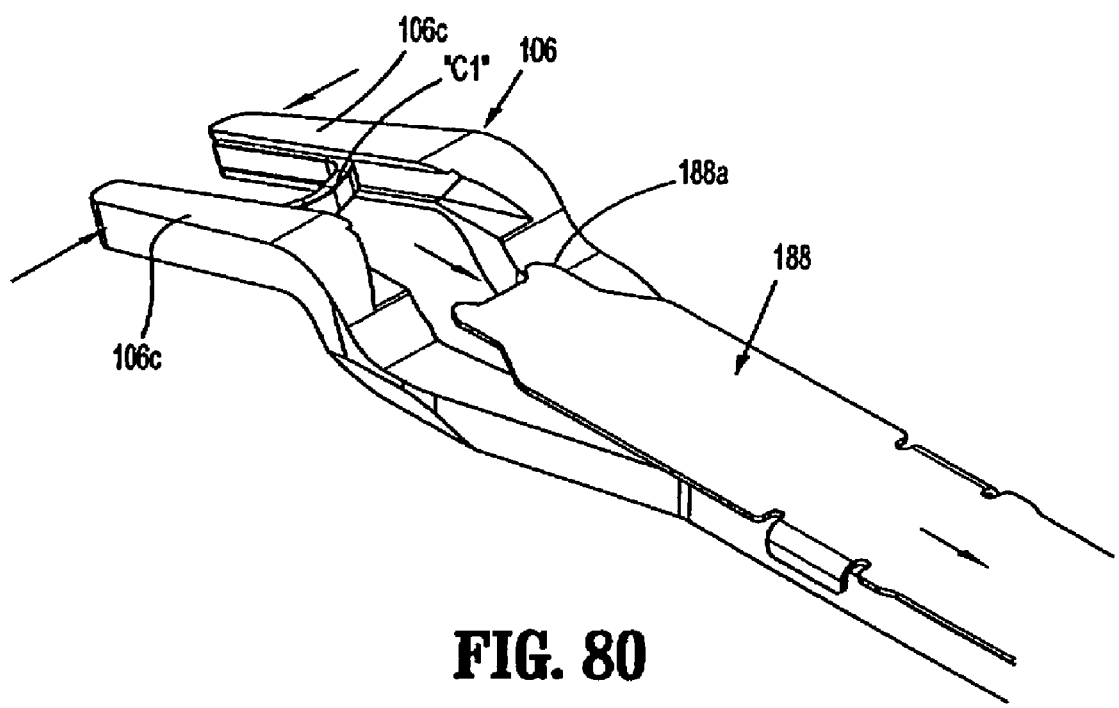
FIG. 80 is a front, perspective view of the jaws of the surgical clip applier illustrating the wedge plate being withdrawn from therebetween.
Figure 84:
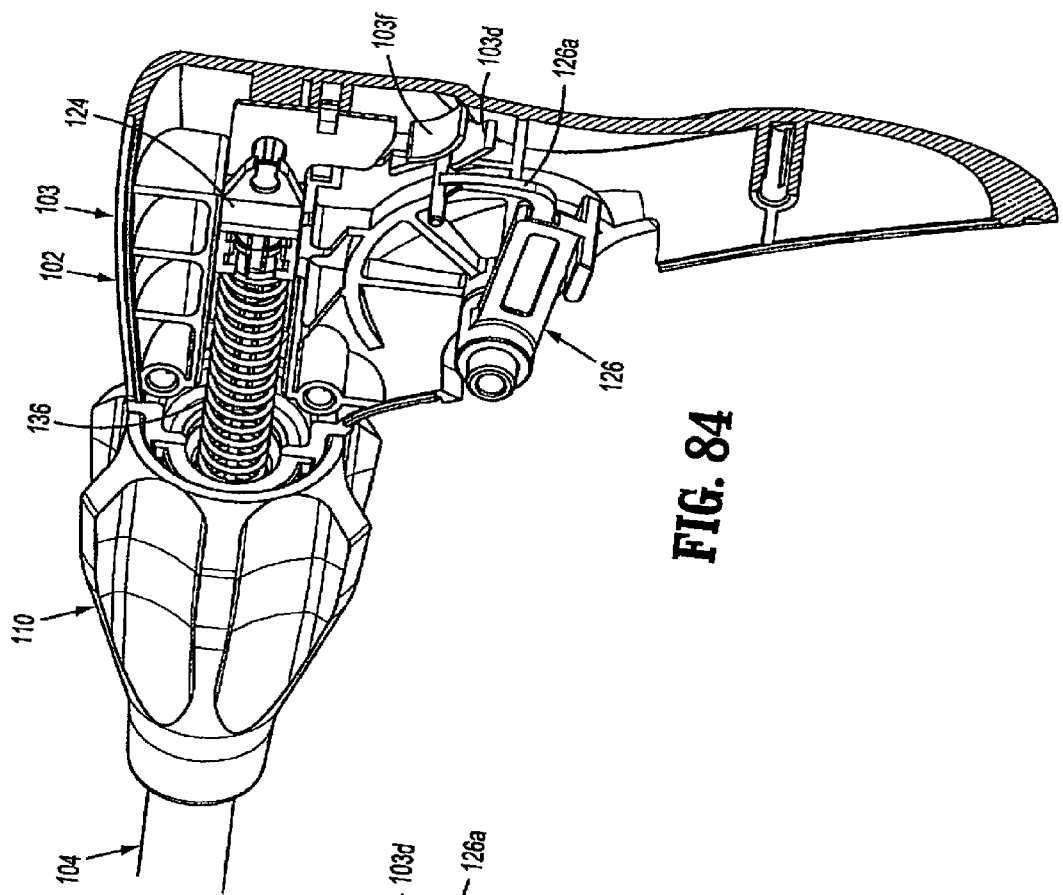
FIG. 84 is a rear, perspective, partial cross-sectional view of the handle assembly during the third stage of the initial stroke of the trigger of the handle assembly.
Figure 83:
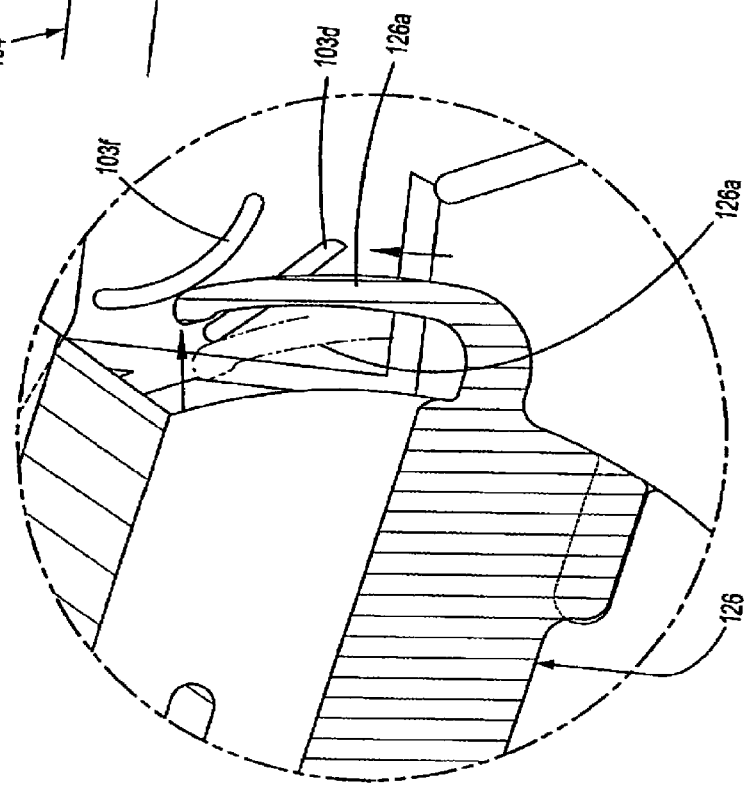
FIG. 83 is an enlarged, elevational, cross-sectional view of the indicated area of detail of FIG. 81.

As wedge plate rack 212 is moved proximally, biasing member 214 is compressed between body portion 212a of wedge plate rack 212 and stub 153e formed in and extending from channel 153c of lower housing 152b. Concomitantly therewith, body portion 212a also moves tab 188b of wedge plate 188 in a proximal direction, thus causing distal end 188a of wedge plate 188 to be withdrawn from between jaw members 106c of jaws 106, as seen in FIGS. 79 and 80. With reference to FIG. 79, when distal end 188a of wedge plate 188 is interposed between jaw members 106c, distal end 188a of wedge plate 188 functions to maintain jaw members 106c spaced apart from one another so as to receive a surgical clip "C1" (see FIG. 80) therebetween and prevent side-load pressure from impeding clip loading. With reference to FIG. 80, when distal end 188a of wedge plate 188 is withdrawn from between jaw members 106c, jaw members 106c are capable of being approximated toward one another to form a surgical clip "C1" disposed therebetween.

Turning now to FIGS. 81-94, as trigger 108 is further squeezed or actuated from the second stage of the initial stroke through a third stage of the initial stroke, as described above, trigger 108 causes wishbone link 122 to further move yoke 124 in a distal direction which, in turn, causes plunger 134 to further move distally and to further move drive bar 140 distally, via shear pin 142. As seen in FIG. 81, biasing member 136 is now fully compressed between yoke 124 and cap 144.

As seen in FIGS. 81 and 82, as trigger 108 is actuated through the third stage of the initial stroke, actuator plate 128 is distally advanced, in the manner described above, thereby causing stem 130b of actuation lever 130 to slidably cam around counter actuation surface 128c. In so doing, actuation lever 130 is rotated clockwise to come into contact with a lever or electrical contact 132d of processor 132b and thus cause processor 132b to change the image on display 132a. For example, the image on display 132a may indicate that a surgical clip "C" has been fired or expelled from surgical clip applier 100.

As seen in FIGS. 81-84, 92 and 93, as trigger 108 is actuated, audible/tactile feedback member 126 functions to create an audible click and/or a tactile vibration, thereby indicating to the user that trigger 108 of surgical clip applier 100 has gone through a complete stroke. In particular, as trigger 108 is actuated, arm 126a of tactile feedback member 126 rides over and/or along a rib 103d formed in at least one of right side half-section 103a and left side half-section 103b. As arm 126a reaches the end of rib 103d, arm 126a snaps over the end of rib 103d and comes into contact with surface 103f of right side half-section 103a and left side half-section 103b, thereby creating and audible sound and a tactile vibration as arm 126a comes into contact with surface 103f.

As seen in FIGS. 85-89, as trigger 108 is actuated through the third stage of the initial stroke, drive bar 140 is further advanced distally, thus causing drive channel 190 to be further advanced distally, in the manner described above. As drive channel 190 is further advanced distally, as seen in FIGS. 85 and 86, tab 190c of drive channel 190, extending into pocket 202b of body portion 202 of slider joint 200, drags or urges body portion 202 of slider joint 200 in a distal direction, thereby compressing biasing member 206 between body portion 202 and stub 153d of lower housing 152b.

Also, as drive channel 190 is further advanced distally, as seen in FIGS. 88 and 89, a distal edge of drive channel 190 engages against camming surfaces 106d of jaw members 106c thus causing jaw members 106c to approximate toward one another and to form surgical clip "C1" interposed therebetween. Since U-shaped channel 230 is fixed to drive channel 190 and moves therewith, U-shaped channel 230 functions to cap drive channel 190 so as to maintain jaw members 106c within drive channel 190 during the approximation of jaws members 106c. As seen in FIG. 90, surgical clip "C1" may be formed or crimped onto a vessel "V" or any other biological tissue.

Also, as drive channel 190 is further advanced distally, as seen in FIG. 91, rack 222 of pawl and rack assembly 220 is moved distally until pawl tooth 224a of pawl 224 is disposed within proximal recess 222c of rack 222.

Figure 94:
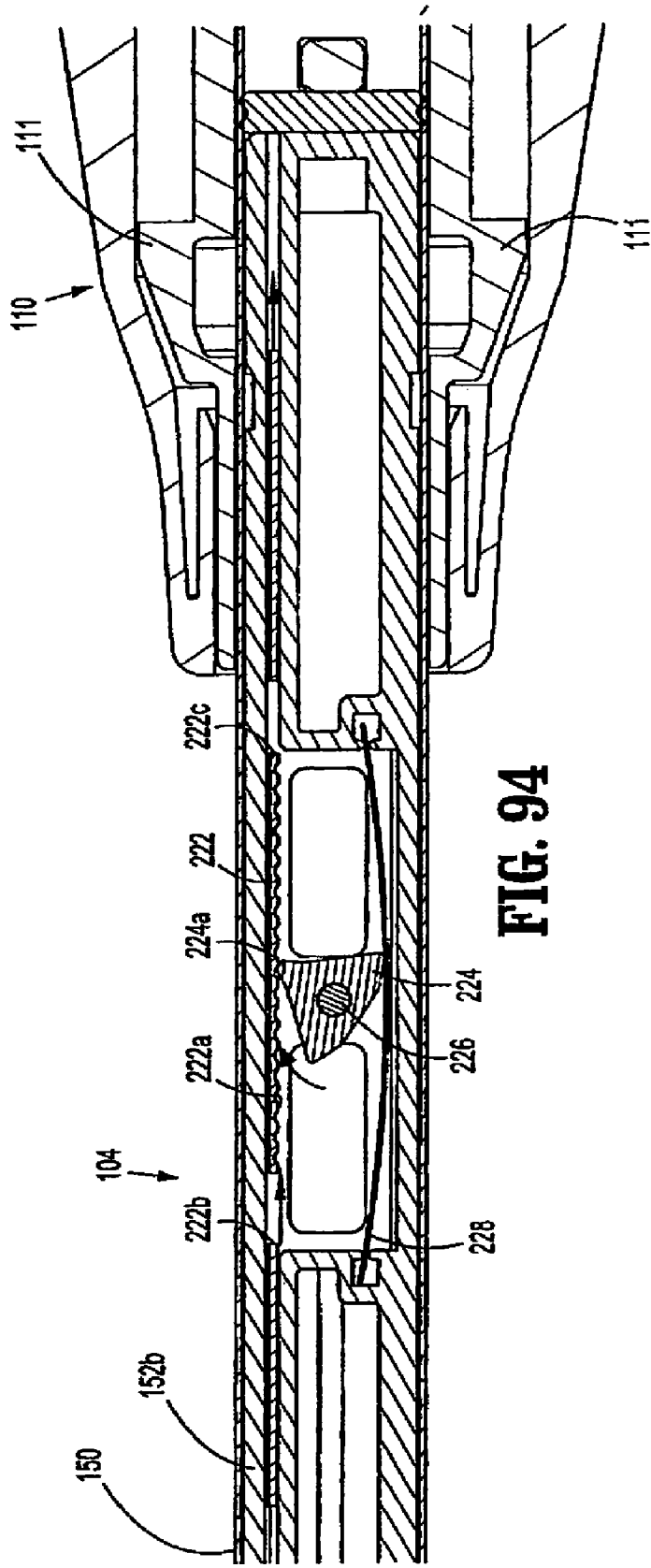
FIG. 94 is a longitudinal, cross-sectional view taken through 64-64 of FIG. 63, illustrating a further operation a pawl and rack assembly.

As seen in FIG. 94 and as will be described in greater detail below, as drive channel 190 is withdrawn in a proximal direction, rack 222 of pawl and rack assembly 220 is moved in a proximal direction such that pawl tooth 224a of pawl 224 is moved out of proximal recess 222c of rack 222 and into engagement with teeth 222a of rack 222. Also, pawl 224 is canted, rotated or rocked about pawl pin 226 causing biasing member 228 to deflect. Biasing member 228 functions to maintain tooth 224a of pawl 224 in engagement with teeth 222a of rack 222, as well as to maintain pawl 224 in a rotated or canted position.

Turning now to FIGS. 95-99, return of trigger 108 to an un-squeezed or unactuated position, is shown. Return of trigger 108 to an un-squeezed or unactuated position is facilitated by the biasing action and forces exerted on plunger 134 by biasing member 136.

Figures 95, 96:
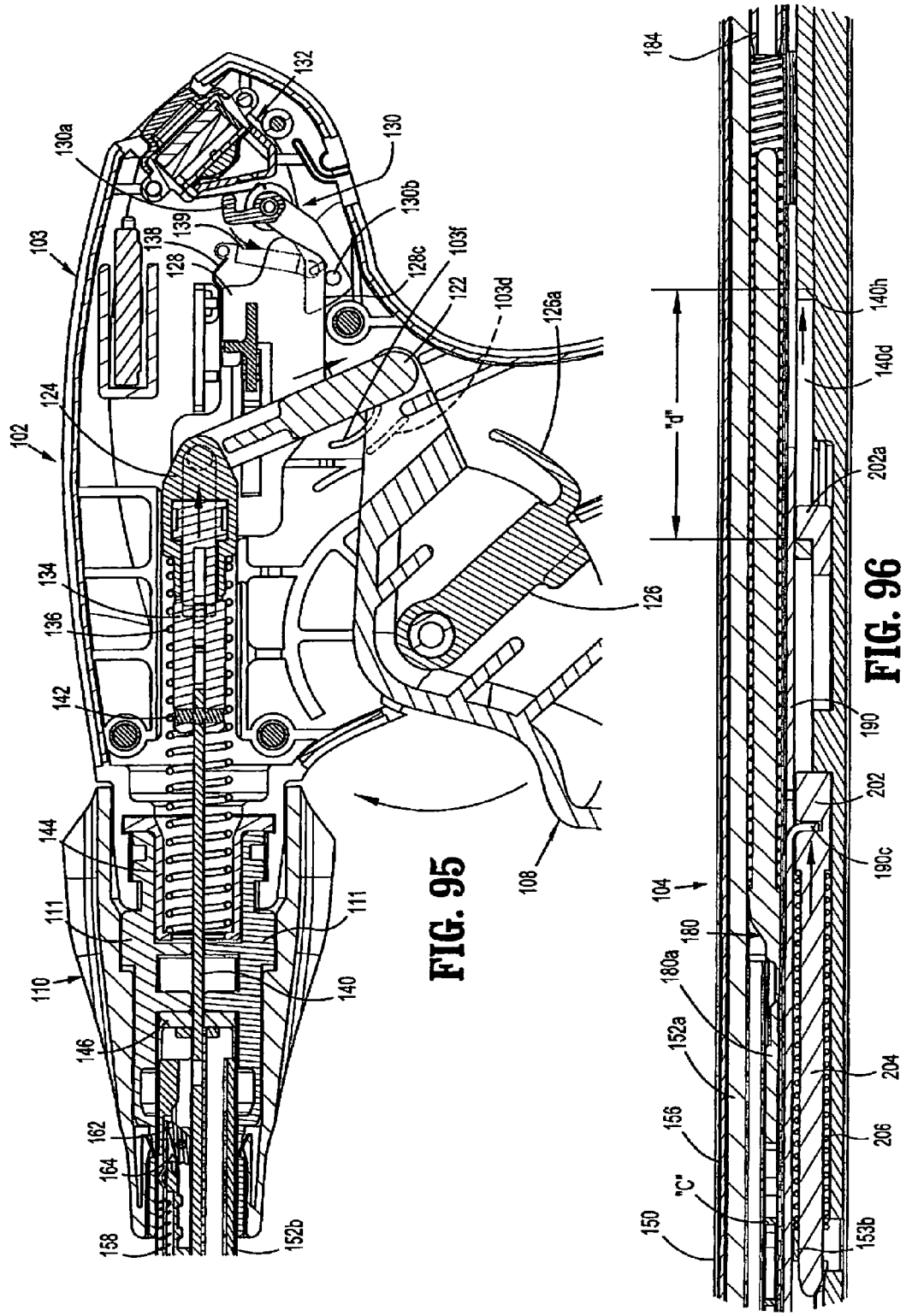
FIG. 95 is a longitudinal, elevational, cross-sectional view of the handle assembly of the surgical clip applier of FIGS. 1-4, illustrating a release stroke of the trigger of the handle assembly.
FIG. 96 is an enlarged, elevational, cross-sectional view of detail 54 of FIG. 49, during the release stoke of the trigger of the handle assembly.

As seen in FIG. 95, as trigger 108 is returned to the un-squeezed position, wishbone link 122 moves yoke 124 in a proximal direction which, in turn, causes plunger 134 to move proximally and to move drive bar 140 proximally, via shear pin 142. As seen in FIG. 95, as drive bar 140 is moved proximally, distal edge 140h and stop 140e of drive bar 140 are backed away from tab 202a of body portion 202 of slider joint 200 thus causing tab 202a to translate through elongate slot 140d of drive bar 140 and increase the length and/or size of dwell "d". As drive bar 140 is retracted proximally, biasing member 206 urges slider joint 200 in proximal direction thereby acting on tab 190c of drive channel 190 to urge drive channel 190 in a proximal direction.

As seen in FIG. 97, as drive channel 190 is moved in a proximal direction, jaw members 106c of jaws 106 return to their un-approximated condition due to the natural spring bias thereof. As seen in FIG. 98, as drive channel 190 is moved in a proximal direction, cut-out 190e formed in side wall 190a of drive channel 190 allows gear 216 to rotate, i.e., counter-clockwise as shown. Rotation of gear 216 results in distal displacement of body portion 212a of wedge plate rack 212 of wedge plate rack mechanism 210 due to the force of biasing member 214 and the inter-engagement of the set of teeth 216a of gear 216 with rack 212b of wedge plate rack 212. As wedge plate rack 212 is moved distally, body portion 212a also moves tab 188b of wedge plate 188 in a distal direction, thus causing distal end 188a of wedge plate 188 to be inserted or reintroduced between jaw members 106c of jaws 106, as seen in FIG. 99.

Figure 102:
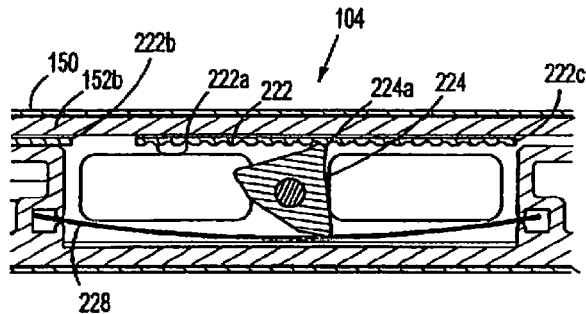
FIG. 102 is a longitudinal, cross-sectional view of FIG. 64, illustrating an operation a pawl and rack assembly during the lockout phase of the device.

Turning now to FIGS. 100-102, the configuration of surgical clip applier 100, following application of the last surgical clip "C", is shown. As seen in FIG. 100, when the last surgical clip "C" is advanced by pusher bar 156 into jaws 106, head portion 180a of clip follower 180 is at a distal-most position due to the urging of biasing member 182. When head portion 180a of clip follower 180 is at a distal-most position, ramp 180c of head portion 180a cams against and urges distal portion 168b of lock-out bar 168 of pusher-bar latch mechanism 166 in a direction counter-clockwise, as shown, toward pusher bar 156 and into distal window 156d of pusher bar 156. With distal portion 168b of lock-out bar 168 positioned in distal window 156d of pusher bar 156, when pusher bar 156 is retracted, pusher bar 156 is prevented from moving proximally to the fully retracted position.

As seen in FIG. 101, since pusher bar 156 is prevented from moving proximally to the fully retracted position by distal portion 168b of lock-out bar 168, as described above, distal portion 162a of latch member 162 is rotated counter-clockwise, as shown, into window 140g of drive bar 140 by arm 164a of biasing member 164. Latch member 162 is prevented from rotating fully by the abutment of proximal portion 162b against an inner surface of shaft assembly 104 and/or outer tube 150. Distal portion 162a of latch member 162 effectively blocks proximal movement of drive bar 140 and thus prevents drive bar 140 from returning to a fully proximal position.

With drive bar 140 prevented from returning to the fully proximal position, as seen in FIG. 102, rack 222 of pawl and rack assembly 220 is prevented from returning to a fully proximal position. As such, tooth 224a of pawl 224 fail to be received within distal recess 222b of rack 222 and thus fail to reset. Thus, tooth 224a of pawl 224 remains engaged with teeth 222a of rack 222, and pawl 224 remains canted with respect to rack 222. As such, rack 222 is prevented from moving in a distal direction because rack 222 is wedged by pawl 224 and can not reset itself.

With distal portion 168b of lock-out bar 168 positioned in distal window 156d of pusher bar 156, with distal portion 162a of latch member 162 rotated into window 140g of drive bar 140, and with tooth 224a of pawl 224 remaining engaged with teeth 222a of rack 222, trigger 108 of surgical clip applier 100 is prevented from moving distally and/or proximally and the mechanism is locked.

Figure 103:
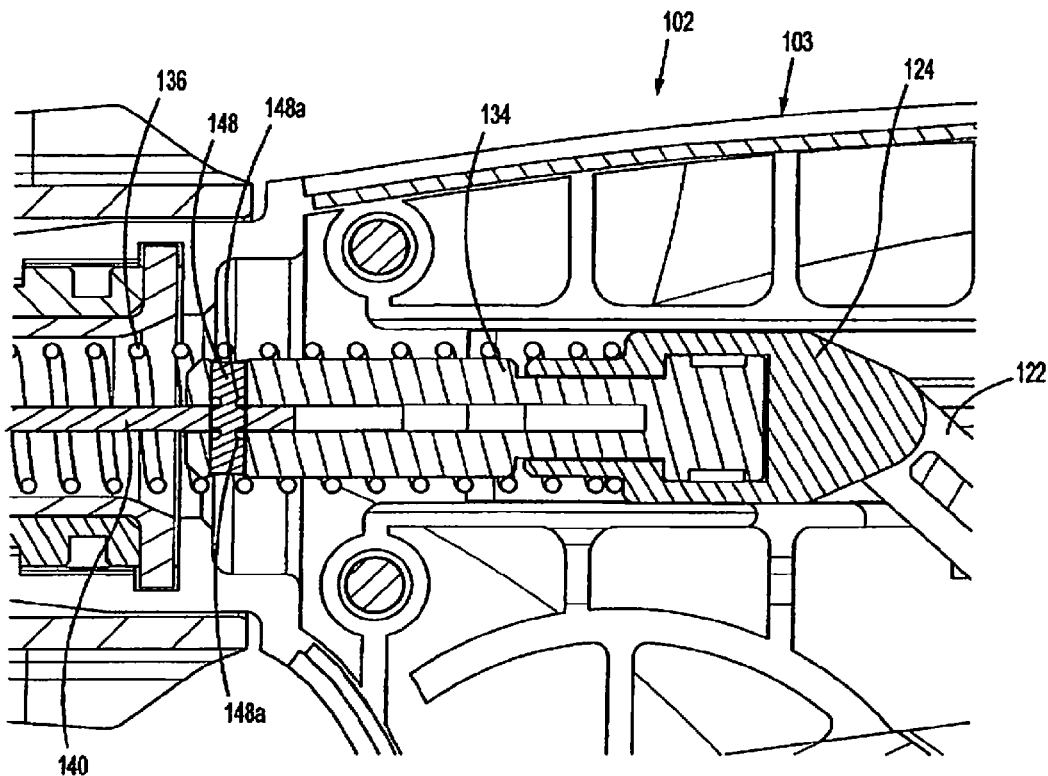
FIG. 103 is an enlarged, longitudinal, cross-sectional view of the handle assembly, illustrating the operation of a drive assembly after the lockout mechanism has been engaged.
Figure 104:
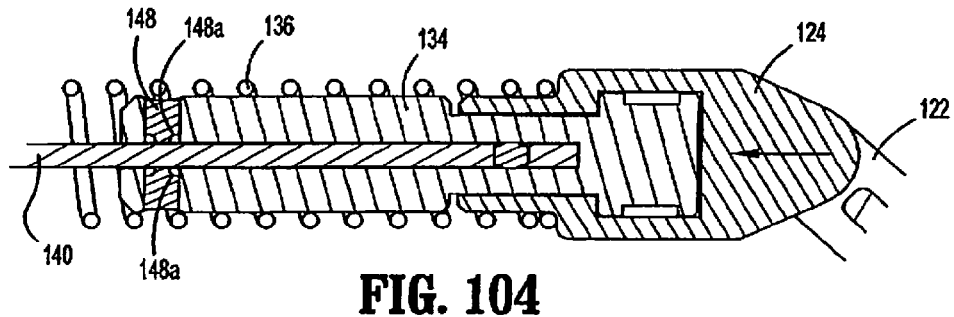
FIG. 104 is an enlarged, longitudinal, cross-sectional view of the handle assembly, illustrating the operation of a shear pin with the drive assembly breaking through the lockout mechanism.

As seen in FIGS. 103 and 104, if a user of surgical clip applier 100 attempts to exert an excessive force onto trigger 108, the excessive force will be transmitted to shear pin 148 via plunger 134. Since drive bar 140 is prevented from moving distally, the excessive force on plunger 134 is transmitted to shear pin 148, causing shear pin 148 to fail or break at annular recesses 148a thereof. Once shear pin 148 is broken, plunger 134 is capable of moving in a distal direction, however, no force is capable of being transmitted to drive bar 140 via shear pin 148.

As seen in FIGS. 6-8, surgical clip applier 100 includes a spring stop 138 disposed within handle assembly 102 which keeps actuator plate 128 from falling distally/proximally when surgical clip applier 100 is held in a vertical orientation. In particular, spring stop 138 is fixedly secured to actuator plate 128 and includes a resilient arm 138a that frictionally or snap-fit engages a surface within housing 103. In this manner, since actuator plate 128 is held in position by spring stop 138, actuator plate 128 does not freely move in a distal or proximal direction as surgical clip applier 100 is maneuvered to a vertical orientation.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. An apparatus for application of surgical clips to body tissue, the apparatus comprising:
 a) a handle assembly;
 b) a shaft assembly extending distally from the handle assembly and defining a longitudinal axis;
 c) a plurality of surgical clips disposed within the shaft assembly;
 d) jaws mounted adjacent a distal end portion of the shaft assembly, the jaws including a pair of jaw members movable between a spaced-apart and an approximated position;

e) a clip pusher bar configured to individually distally advance a surgical clip to the jaws while the jaw members are in the spaced apart position;

f) a drive bar at least partially disposed within the handle assembly and the shaft assembly, the drive bar being longitudinally movable in response to actuation of a trigger of the handle assembly;

g) a drive channel positioned adjacent the first and second jaw members to move the jaw members to the approximated position; and h) a lockout system at all times spaced a fixed distance from a distal end of the shaft assembly and configured to selectively engage and extend through a window formed in a distal region of the clip pusher bar to prevent the clip pusher bar from returning to a home position and to prevent the trigger from completing a full stroke when the plurality of clips are substantially exhausted.

2. The apparatus according to claim 1, wherein the lockout system includes a pusher-bar latch mechanism supported in the shaft assembly, wherein a lock-out bar of the latch mechanism is actuated to engage the clip pusher bar when a final clip is exhausted, whereby the lock-out bar prevents the clip pusher bar from returning to the home position.

3. The apparatus according to claim 2, further comprising a clip follower slidably disposed within the shaft assembly at a location proximal of the plurality of clips, wherein the clip follower urges the lock-out bar of the pusher-bar latch mechanism into engagement with the clip pusher bar when the final clip is exhausted.

4. The apparatus according to claim 2, wherein the lockout system includes:

a rack having a plurality of ratchet teeth and being secured to the drive channel; and a pawl having at least one tooth and being disposed at a location to selectively engage the rack, wherein the pawl is biased into engagement with the rack, wherein as the drive channel is longitudinally reciprocated, the plurality of teeth are passed over the pawl, and wherein the pawl prevents inadvertent return of the drive channel before full actuation of the apparatus.

5. The apparatus according to claim 4, wherein the lockout system includes:

a latch member operatively engageable by the clip pusher bar and the drive channel, wherein the latch member includes a position that is out of engagement with the drive channel when the clip pusher bar is in the home position, and a position that is engaged with the drive channel when the clip pusher bar is in a non-home position, wherein when the clip pusher bar is prevented from returning to the home position by the lock-out bar, the latch member is engaged with drive channel and prevents the drive channel from moving proximally, whereby the plurality of teeth of the rack are maintained in engagement with the pawl.

6. The apparatus according to claim 1, further comprising a wedge plate slidably supported in the shaft assembly, the wedge plate includes a distal end configured and dimensioned for placement between the jaw members when the jaw members are in the spaced-apart position, wherein the wedge plate is moved in a proximal direction to withdraw the distal end thereof from between the jaw members when the drive channel is moved in a distal direction.

7. The apparatus according to claim 6, further comprising a gear operatively disposed between the wedge plate and the drive channel, wherein the gear translates distal movement of the drive channel into proximal movement of the wedge plate and proximal movement of the drive channel into distal movement of the wedge plate.

8. The apparatus according to claim 6, wherein a delay is provided between the distal advancement of the drive bar and the distal advancement of the drive channel.

9. The apparatus according to claim 1, further comprising a trip mechanism supported on the drive bar, the trip mechanism includes a trip lever biased into contact with the clip pusher bar, wherein distal movement of the drive bar moves the trip mechanism until the trip lever thereof engages a lip of the clip pusher bar and in turn distally moves the clip pusher bar.

10. The apparatus according to claim 1, further comprising a shear pin operatively connected to the drive bar to transmit axial forces to the drive bar during movement of the trigger, wherein the shear pin includes at least one region of reduced strength.

11. The apparatus according to claim 10, wherein the shear pin will fail at the at least one region of reduced strength when a minimum predetermined shear force is exerted on the shear pin.

12. The apparatus according to claim 1, wherein the jaws are mounted adjacent a distal end portion of the shaft assembly in a manner capable of splaying in an outward direction in order to accommodate a clip between the pair of jaw members.

13. An apparatus for application of surgical clips to body tissue, the apparatus comprising:

a) a handle assembly;

b) a shaft assembly extending distally from the handle assembly and defining a longitudinal axis;

c) a plurality of surgical clips disposed within the shaft assembly;

d) jaws mounted adjacent a distal end portion of the shaft assembly, the jaws including a pair of jaw members movable between a spaced-apart and an approximated position;

e) a clip pusher bar configured to individually distally advance a surgical clip to the jaws while the jaw members are in the spaced apart position;

f) a drive bar at least partially disposed within the handle assembly and the shaft assembly, the drive bar being longitudinally movable in response to actuation of a trigger of the handle assembly;

g) a drive channel positioned adjacent the first and second jaw members to move the jaw members to the approximated position;

h) a lockout system at all times spaced a fixed distance from a distal end of the shaft assembly and configured to selectively engage and extend through a window formed in a distal region of the clip pusher bar to prevent the clip pusher bar from returning to a home position and to prevent the trigger from completing a full stroke when the plurality of clips are substantially exhausted; and i) a trip mechanism supported on the drive bar, the trip mechanism includes:

a trip block removably secured to the clip pusher bar;

a trip lever pivotally connected to the trip block and biased into contact with the clip pusher bar; and a compression spring interposed between the trip block and the trip lever, wherein distal movement of the drive bar moves the trip mechanism until the trip lever thereof engages a lip of the clip pusher bar and in turn distally moves the clip pusher bar.

14. The apparatus according to claim 13, wherein the lockout system includes a pusher-bar latch mechanism supported in the shaft assembly, wherein a lock-out bar of the latch mechanism is actuated to engage the clip pusher bar when a final clip is exhausted, whereby the lock-out bar prevents the clip pusher bar from returning to the home position.

15. The apparatus according to claim 14, wherein the lock-out system includes:
- a rack having a plurality of ratchet teeth and being secured to the drive channel; and
- a pawl having at least one tooth and being disposed at a location to selectively engage the rack, wherein the pawl is biased into engagement with the rack, wherein as the drive channel is longitudinally reciprocated, the plurality of teeth are passed over the pawl, and wherein the pawl prevents inadvertent return of the drive channel before full actuation of the apparatus.

16. The apparatus according to claim 15, wherein the lock-out system includes:
- a latch member operatively engageable by the clip pusher bar and the drive channel, wherein the latch member includes a position that is out of engagement with the drive channel when the clip pusher bar is in the home position, and a position that is engaged with the drive channel when the clip pusher bar is in a non-home position,
- wherein when the clip pusher bar is prevented from returning to the home position by the lock-out bar, the latch member is engaged with drive channel and prevents the drive channel from moving proximally, whereby the plurality of teeth of the rack are maintained in engagement with the pawl.

17. The apparatus according to claim 14, further comprising a clip follower slidably disposed within the shaft assembly at a location proximal of the plurality of clips, wherein the clip follower urges the lock-out bar of the pusher-bar latch mechanism into engagement with the clip pusher bar when the final clip is exhausted.

18. The apparatus according to claim 13, further comprising a wedge plate slidably supported in the shaft assembly, the wedge plate includes a distal end configured and dimensioned for placement between the jaw members when the jaw members are in the spaced-apart position, wherein the wedge plate is moved in a proximal direction to withdraw the distal end thereof from between the jaw members when the drive channel is moved in a distal direction.

19. The apparatus according to claim 15, further comprising a gear operatively disposed between the wedge plate and the drive channel, wherein the gear translates distal movement of the drive channel into proximal movement of the wedge plate and proximal movement of the drive channel into distal movement of the wedge plate.

20. The apparatus according to claim 13, wherein a delay is provided between the distal advancement of the drive bar and the distal advancement of the drive channel.

21. The apparatus according to claim 13, further comprising a shear pin operatively connected to the drive bar to transmit axial forces to the drive bar during movement of the trigger, wherein the shear pin includes at least one region of reduced strength.

22. The apparatus according to claim 21, wherein the shear pin will fail at the at least one region of reduced strength when a minimum predetermined shear force is exerted on the shear pin.

* * * * *